(12) United States Patent
Jackson et al.

(10) Patent No.: US 11,013,638 B2
(45) Date of Patent: May 25, 2021

(54) WOUND OR SKIN TREATMENT DEVICES AND METHODS

(71) Applicant: Neodyne Biosciences, Inc., Newark, CA (US)

(72) Inventors: Jasper Jackson, Newark, CA (US); John A. Zepeda, Los Altos, CA (US); Adam C. French, San Francisco, CA (US); Darren G. Doud, Los Altos, CA (US); Geoffrey C. Gurtner, Palo Alto, CA (US); Brett A. Follmer, Santa Clara, CA (US); William R. Beasley, Los Altos, CA (US); Paul Yock, Atherton, CA (US); Keiichiro Ichiryu, Campbell, CA (US); Manuel A. Cardona Pamplona, East Palo Alto, CA (US); Tor C. Krog, Seattle, WA (US); Kemal Levi, Mountain View, CA (US)

(73) Assignee: Neodyne Biosciences, Inc., Newark, CA (US)

( * ) Notice: Subject to any disclaimer, the term of this patent is extended or adjusted under 35 U.S.C. 154(b) by 667 days.

(21) Appl. No.: 15/842,794

(22) Filed: Dec. 14, 2017

(65) Prior Publication Data

US 2018/0104107 A1 Apr. 19, 2018

Related U.S. Application Data

(63) Continuation of application No. 13/789,264, filed on Mar. 7, 2013, now Pat. No. 9,844,470, which is a
(Continued)

(51) Int. Cl.
*A61F 13/00* (2006.01)
*A61F 13/02* (2006.01)
(Continued)

(52) U.S. Cl.
CPC ........ *A61F 13/00* (2013.01); *A61F 13/00076* (2013.01); *A61F 13/00085* (2013.01);
(Continued)

(58) Field of Classification Search
CPC . A61B 9/022; A61B 17/085; A61F 13/00038; A61F 13/00076;
(Continued)

(56) References Cited

U.S. PATENT DOCUMENTS

| 114,750 A | 5/1871 | Battersby |
| 363,538 A | 5/1887 | Penny |

(Continued)

FOREIGN PATENT DOCUMENTS

| CA | 2321491 A1 | 9/1999 |
| CA | 2621387 A1 | 3/2007 |

(Continued)

OTHER PUBLICATIONS

3M Healthcare (May 2004). "Tips for Trouble-Free Taping," 3M HealthCare: St. Paul, MN, four pages.
(Continued)

*Primary Examiner* — Kim M Lewis
(74) *Attorney, Agent, or Firm* — Dorsey & Whitney LLP

(57) ABSTRACT

Devices, kits and methods described herein may be for treatment to skin, including but not limited to wound healing, the treatment, amelioration, and/or prevention of scars or keloids. A book-like packaging, applicator and/or tensioning device may be used to apply a dressing to a subject. The packaging, applicator and/or tensioning device may apply and/or maintain a strain in an elastic dressing.

39 Claims, 31 Drawing Sheets

Related U.S. Application Data continuation of application No. 13/345,524, filed on Jan. 6, 2012, now Pat. No. 9,248,048, and a continuation-in-part of application No. 12/854,859, filed on Aug. 11, 2010, now Pat. No. 8,592,640.

(60) Provisional application No. 61/443,647, filed on Feb. 16, 2011, provisional application No. 61/430,908, filed on Jan. 7, 2011.

(51) Int. Cl.
*A61F 15/00* (2006.01)
*A61L 15/26* (2006.01)

(52) U.S. Cl.
CPC ............ *A61F 13/02* (2013.01); *A61F 13/023* (2013.01); *A61F 13/0236* (2013.01); *A61F 13/0259* (2013.01); *A61F 15/001* (2013.01); *A61F 15/005* (2013.01); *A61L 15/26* (2013.01)

(58) Field of Classification Search
CPC .............. A61F 13/00085; A61F 13/023; A61F 13/0236; A61F 13/0243; A61F 13/0253; A61F 13/0256; A61F 13/0266; A61F 15/001; A61F 15/005; A61F 15/26
See application file for complete search history.

(56) References Cited

U.S. PATENT DOCUMENTS

| | | |
|---|---|---|
| 633,050 A | 9/1899 | Spenard |
| 1,074,413 A | 9/1913 | Baun et al. |
| 1,774,489 A | 8/1930 | David |
| 1,969,188 A | 8/1934 | Spicer |
| 2,018,517 A | 10/1935 | Edward |
| 2,303,131 A | 11/1942 | Morgan |
| 2,371,978 A | 3/1945 | Perham |
| 2,421,193 A | 5/1947 | James |
| 2,472,009 A | 5/1949 | James |
| 2,714,382 A | 8/1955 | Solis |
| 2,722,220 A | 11/1955 | Mestrand |
| 2,762,371 A | 9/1956 | Guio |
| 3,103,218 A | 9/1963 | Ajemian |
| 3,402,716 A | 9/1968 | Baxter |
| 3,487,836 A | 1/1970 | Niebel et al. |
| 3,528,426 A | 9/1970 | Vukojevic |
| 3,575,782 A | 4/1971 | Hansen |
| 3,613,679 A | 10/1971 | Bijou |
| 3,645,835 A | 2/1972 | Hodgson |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,983,878 A | 10/1976 | Kawchitch |
| 4,038,989 A | 8/1977 | Romero-sierra et al. |
| 4,073,298 A | 2/1978 | Le Roy |
| 4,114,624 A | 9/1978 | Haverstock |
| 4,141,363 A | 2/1979 | James et al. |
| 4,173,131 A | 11/1979 | Melton et al. |
| 4,222,383 A | 9/1980 | Schossow |
| 4,282,005 A | 8/1981 | Sato et al. |
| 4,346,700 A | 8/1982 | Dunshee et al. |
| 4,370,981 A | 2/1983 | Sanderson |
| 4,413,621 A | 11/1983 | Mccracken et al. |
| 4,423,731 A | 1/1984 | Roomi |
| 4,425,176 A | 1/1984 | Shibano et al. |
| 4,447,482 A | 5/1984 | Heinzelman et al. |
| 4,496,535 A | 1/1985 | Gould et al. |
| 4,531,521 A | 7/1985 | Haverstock |
| 4,535,772 A | 8/1985 | Sheehan |
| 4,539,990 A | 9/1985 | Stivala |
| 4,549,653 A | 10/1985 | Lauritzen |
| 4,598,004 A | 7/1986 | Heinecke |
| 4,605,005 A | 8/1986 | Sheehan |
| 4,646,731 A | 3/1987 | Brower |
| 4,653,492 A | 3/1987 | Parsons |
| 4,696,301 A | 9/1987 | Barabe |
| 4,699,133 A | 10/1987 | Schafer et al. |
| 4,702,251 A | 10/1987 | Sheehan |
| 4,706,661 A | 11/1987 | Barrett |
| 4,732,146 A | 3/1988 | Fasline et al. |
| 4,742,826 A | 5/1988 | Mclorg |
| 4,753,232 A | 6/1988 | Ward |
| 4,780,168 A | 10/1988 | Beisang et al. |
| 4,787,381 A | 11/1988 | Hubbard et al. |
| 4,807,613 A | 2/1989 | Koehnke et al. |
| 4,815,457 A | 3/1989 | Mazars et al. |
| 4,815,468 A | 3/1989 | Annand |
| 4,825,866 A | 5/1989 | Pierce |
| 4,881,546 A | 11/1989 | Kaessmann |
| 4,915,102 A | 4/1990 | Kwiatek et al. |
| 4,917,929 A | 4/1990 | Heinecke |
| 4,924,866 A | 5/1990 | Yoon |
| 4,950,282 A | 8/1990 | Beisang et al. |
| RE33,353 E | 9/1990 | Heinecke |
| 4,984,584 A | 1/1991 | Hansen et al. |
| 5,011,492 A | 4/1991 | Heimerl et al. |
| 5,026,389 A | 6/1991 | Thieler |
| 5,047,047 A | 9/1991 | Yoon |
| 5,058,579 A | 10/1991 | Terry et al. |
| 5,066,299 A | 11/1991 | Bellingham |
| 5,106,629 A | 4/1992 | Cartmell et al. |
| 5,127,412 A | 7/1992 | Cosmetto et al. |
| 5,176,703 A | 1/1993 | Peterson |
| 5,234,462 A | 8/1993 | Pavletic |
| 5,259,835 A | 11/1993 | Clark et al. |
| 5,263,970 A | 11/1993 | Preller |
| 5,333,753 A | 8/1994 | Etheredge |
| 5,383,900 A | 1/1995 | Krantz |
| 5,507,775 A | 4/1996 | Ger et al. |
| 5,520,762 A | 5/1996 | Rasmussen et al. |
| 5,522,879 A | 6/1996 | Scopelianos |
| 5,545,713 A | 8/1996 | Krejci et al. |
| 5,549,713 A | 8/1996 | Kim |
| 5,552,162 A | 9/1996 | Lee |
| 5,562,705 A | 10/1996 | Whiteford |
| 5,628,724 A | 5/1997 | Debusk et al. |
| 5,649,960 A | 7/1997 | Pavletic |
| 5,662,624 A | 9/1997 | Sundstroem et al. |
| 5,662,714 A | 9/1997 | Charvin et al. |
| 5,662,717 A | 9/1997 | Burns |
| 5,713,842 A | 2/1998 | Kay |
| 5,723,009 A * | 3/1998 | Frechet ................. A61B 90/02 128/898 |
| 5,758,662 A | 6/1998 | Hall |
| 5,759,560 A | 6/1998 | Dillon |
| 5,779,659 A | 7/1998 | Allen |
| 5,885,254 A | 3/1999 | Matyas |
| 5,891,076 A | 4/1999 | Fabo |
| 5,919,476 A | 7/1999 | Fischer et al. |
| 5,931,800 A | 8/1999 | Rasmussen et al. |
| 5,947,998 A | 9/1999 | Cartmell et al. |
| 5,998,694 A | 12/1999 | Jensen et al. |
| 6,007,564 A | 12/1999 | Haverstock |
| 6,043,406 A | 3/2000 | Sessions et al. |
| 6,093,465 A | 7/2000 | Gilchrist et al. |
| 6,120,525 A | 9/2000 | Westcott |
| 6,255,552 B1 | 7/2001 | Cummings et al. |
| 6,264,976 B1 | 7/2001 | Heinecke et al. |
| 6,284,941 B1 | 9/2001 | Cox et al. |
| 6,297,420 B1 | 10/2001 | Heincke |
| 6,297,423 B1 | 10/2001 | Schoenfeldt et al. |
| 6,343,224 B1 | 1/2002 | Parker |
| 6,346,653 B1 | 2/2002 | Sessions et al. |
| 6,410,818 B1 | 6/2002 | Oyaski |
| 6,469,066 B1 | 10/2002 | Dosch et al. |
| 6,472,581 B1 | 10/2002 | Muramatsu et al. |
| 6,485,503 B2 | 11/2002 | Jacobs et al. |
| 6,495,230 B1 | 12/2002 | Do Canto |
| 6,570,051 B1 | 5/2003 | Beaudry |
| 6,572,878 B1 | 6/2003 | Blaine |
| 6,573,419 B2 | 6/2003 | Naimer |

(56) References Cited

U.S. PATENT DOCUMENTS

| | | |
|---|---|---|
| 6,634,653 B2 | 10/2003 | Chatterjea |
| 6,726,696 B1 | 4/2004 | Houser et al. |
| 6,759,481 B2 | 7/2004 | Tong |
| 6,822,133 B2 | 11/2004 | Lebner |
| 6,831,205 B2 | 12/2004 | Lebner |
| 6,870,074 B2 | 3/2005 | Gilman |
| 6,986,855 B1 | 1/2006 | Hood et al. |
| 7,066,182 B1 | 6/2006 | Dunshee |
| 7,066,934 B2 | 6/2006 | Kirsch |
| 7,122,712 B2 | 10/2006 | Lutri et al. |
| 7,135,606 B1 | 11/2006 | Dozier et al. |
| 7,227,050 B2 | 6/2007 | Sigurjonsson et al. |
| 7,332,641 B2 | 2/2008 | Lebner et al. |
| 7,354,446 B2 | 4/2008 | Lebner |
| 7,414,168 B2 | 8/2008 | Lebner |
| 7,456,332 B2 | 11/2008 | Beaudry |
| 7,511,185 B2 | 3/2009 | Lebner |
| 7,563,941 B2 | 7/2009 | Lebner et al. |
| 7,683,234 B2 * | 3/2010 | Gurtner .................. A61L 15/42 602/50 |
| 7,834,232 B2 | 11/2010 | Rastegar et al. |
| RE42,126 E | 2/2011 | Ye et al. |
| 8,063,263 B2 | 11/2011 | Gurtner et al. |
| 8,168,850 B2 * | 5/2012 | Gurtner .................. A61L 15/42 602/50 |
| 8,183,428 B2 | 5/2012 | Gurtner et al. |
| 8,389,791 B2 | 3/2013 | Gurtner et al. |
| 8,395,011 B2 | 3/2013 | Zepeda et al. |
| 8,592,640 B2 * | 11/2013 | Zepeda .............. A61F 13/0266 602/58 |
| 8,674,164 B2 | 3/2014 | Zepeda et al. |
| 9,248,048 B2 * | 2/2016 | Jackson .................. A61F 13/02 |
| 9,248,049 B2 | 2/2016 | Gurtner et al. |
| 9,248,051 B2 | 2/2016 | Gurtner et al. |
| 9,358,009 B2 | 6/2016 | Yock et al. |
| 9,492,329 B2 | 11/2016 | Zepeda et al. |
| 9,844,470 B2 * | 12/2017 | Jackson .................. A61F 13/02 |
| 10,420,557 B2 | 9/2019 | Yock et al. |
| 10,517,768 B2 | 12/2019 | Zepeda et al. |
| 2002/0013300 A1 | 1/2002 | Capelli-schellpfeffer |
| 2002/0193723 A1 | 12/2002 | Girardin et al. |
| 2003/0014053 A1 | 1/2003 | Nguyen et al. |
| 2003/0040687 A1 | 2/2003 | Boynton et al. |
| 2003/0092969 A1 | 5/2003 | Omalley et al. |
| 2003/0220700 A1 | 11/2003 | Hammer et al. |
| 2004/0059280 A1 | 3/2004 | Makower et al. |
| 2004/0236360 A1 | 11/2004 | Cohn et al. |
| 2005/0033215 A1 | 2/2005 | Lebner |
| 2005/0034731 A1 * | 2/2005 | Rousseau ............. A61F 13/023 128/849 |
| 2005/0070956 A1 * | 3/2005 | Rousseau ............. A61B 17/085 606/213 |
| 2005/0080453 A1 | 4/2005 | Lebner et al. |
| 2005/0095275 A1 | 5/2005 | Zhu et al. |
| 2005/0095276 A1 | 5/2005 | Kartheus et al. |
| 2005/0125051 A1 | 6/2005 | Eidenschink et al. |
| 2005/0245966 A1 | 11/2005 | Hammerslag et al. |
| 2005/0274453 A1 | 12/2005 | Anvar |
| 2006/0009099 A1 | 1/2006 | Jonn et al. |
| 2006/0020235 A1 | 1/2006 | Siniaguine |
| 2006/0037091 A1 | 2/2006 | Gurtner et al. |
| 2006/0246802 A1 | 11/2006 | Hughes et al. |
| 2006/0282135 A1 | 12/2006 | Tankovich |
| 2007/0093161 A1 | 4/2007 | Eede et al. |
| 2007/0129776 A1 | 6/2007 | Robins et al. |
| 2007/0142761 A1 | 6/2007 | Aali |
| 2007/0191752 A1 | 8/2007 | Lebner |
| 2007/0282235 A1 | 12/2007 | Beaudry |
| 2007/0282374 A1 | 12/2007 | Sogard et al. |
| 2008/0033334 A1 * | 2/2008 | Gurtner .................. A61L 15/58 602/50 |
| 2008/0051687 A1 | 2/2008 | Rogers |
| 2008/0208098 A1 | 8/2008 | Rennix |
| 2008/0228220 A1 | 9/2008 | Weiser |
| 2009/0131845 A1 | 5/2009 | Gurtner et al. |
| 2009/0163844 A1 * | 6/2009 | Gurtner ............... A61F 13/0233 602/53 |
| 2009/0177136 A1 | 7/2009 | Liedtke et al. |
| 2010/0056873 A1 | 3/2010 | Allen et al. |
| 2010/0191253 A1 | 7/2010 | Oostman, Jr. et al. |
| 2010/0280428 A1 | 11/2010 | Widgerow et al. |
| 2011/0152738 A1 * | 6/2011 | Zepeda ............... A61F 13/0243 602/53 |
| 2011/0319798 A1 | 12/2011 | Digrazia |
| 2012/0035521 A1 | 2/2012 | Zepeda et al. |
| 2012/0046586 A1 | 2/2012 | Gurtner et al. |
| 2012/0046590 A1 | 2/2012 | Yock et al. |
| 2012/0046591 A1 | 2/2012 | Gurtner et al. |
| 2012/0203273 A1 | 8/2012 | Riskin et al. |
| 2012/0209377 A1 | 8/2012 | Machold et al. |
| 2012/0221044 A1 * | 8/2012 | Archibald ............ A61B 17/085 606/214 |
| 2012/0226214 A1 | 9/2012 | Gurtner et al. |
| 2012/0226306 A1 | 9/2012 | Jackson et al. |
| 2013/0012858 A1 | 1/2013 | Jackson et al. |
| 2013/0184629 A1 | 7/2013 | Gurtner et al. |
| 2013/0190673 A1 | 7/2013 | Gurtner et al. |
| 2013/0281904 A1 | 10/2013 | Jackson et al. |
| 2014/0088481 A1 | 3/2014 | Jackson et al. |
| 2014/0135677 A1 | 5/2014 | Zepeda et al. |
| 2014/0135678 A1 | 5/2014 | Zepeda et al. |
| 2015/0141836 A1 | 5/2015 | Naumann et al. |
| 2016/0213522 A1 | 7/2016 | Gurtner et al. |
| 2017/0020522 A1 | 1/2017 | Yock et al. |
| 2017/0112673 A1 | 4/2017 | Jackson et al. |

FOREIGN PATENT DOCUMENTS

| | | |
|---|---|---|
| CN | 1414842 A | 4/2003 |
| CN | 1608604 A | 4/2005 |
| CN | 102665623 A | 9/2012 |
| EP | 2161011 A1 | 3/2010 |
| EP | 2464322 A2 | 6/2012 |
| JP | 2004515256 A | 5/2004 |
| JP | 2004223087 A | 8/2004 |
| JP | 2004536898 A | 12/2004 |
| JP | 2006513748 A | 4/2006 |
| JP | 2007537781 A | 12/2007 |
| JP | 2009545382 A | 12/2009 |
| JP | 2013501591 A | 1/2013 |
| RU | 2019138 C1 | 9/1994 |
| WO | 9717919 A1 | 5/1997 |
| WO | 9730700 A2 | 8/1997 |
| WO | 9730700 A3 | 10/1997 |
| WO | 0053139 A1 | 9/2000 |
| WO | 0139693 A2 | 6/2001 |
| WO | 0139693 A3 | 12/2001 |
| WO | 0215816 A2 | 2/2002 |
| WO | 0245698 A2 | 6/2002 |
| WO | 0245698 A3 | 7/2002 |
| WO | 02092783 A2 | 11/2002 |
| WO | 2002087645 A1 | 11/2002 |
| WO | 0215816 A3 | 10/2003 |
| WO | 2004060413 A1 | 7/2004 |
| WO | 02092783 A3 | 7/2005 |
| WO | 2005079674 A1 | 9/2005 |
| WO | 2005096981 A2 | 10/2005 |
| WO | 2005096981 A3 | 3/2006 |
| WO | 2006124671 A2 | 11/2006 |
| WO | 2006124671 A3 | 4/2007 |
| WO | 2008019051 A2 | 2/2008 |
| WO | 2008019051 A3 | 4/2008 |
| WO | 2011019859 A2 | 2/2011 |
| WO | 2011019859 A3 | 4/2011 |
| WO | 2012094648 A1 | 7/2012 |
| WO | 2012119131 A1 | 9/2012 |

OTHER PUBLICATIONS

3M Healthcare. (2001). "Reducing the Risk of Superficial Skin Damage Related to Adhesive Use," 3M HealthCare: St Paul, MN, two pages.

(56) References Cited

OTHER PUBLICATIONS

3M Healthcare. (2003). "Steri-Strip: Skin Closures," Product Insert, 3M HealthCare: St. Paul, MN, one page.
3M Healthcare. (2006). "3MTM Steri-StripTM S Surgical Skin Closure. The Simple, Non-Invase Alternative to Staples and Sutures from the Steri-Strip Family," HealthCare: St. Paul, MN, two pages.
3M Healthcare. (Date Unknown). "3M™ Steri-Strip™ S Surgical Skin Closure," 3M HealthCare: St. Paul, MN, one page.
3M Healthcare. (Date unknown). 3M™ Steri-Strip™ S Surgical Skin Closure. Poster of Available Sizes, 3M HealthCare: St Paul, Mn, three pages.
3M Healthcare. (Jun. 27, 2002). "3M™ Steri-Strip™ Adhesive Skin Closures (reinforced): Commonly Asked Questions," 3M HealthCare: St Paul, MN, pp. 1-4.
3M Healthcare. (Oct. 19, 2006). "3M™ Steri-Strip™ S Surgical Skin Closure: Commonly Asked Questions," 3M Healthcare: St. Paul, MN, pp. 1-8.
3M Medical. (2006). "3MTM Steri-StripTM S Surgical Skin Closure. Patient Care Information," 3M HealthCare: St. Paul, MN, two pages.
3M Medical. (2007). "3MTM Steri-StripTM S Surgical Skin Closure. Application Examples, Comparisons and Results," 3M HealthCare: St. Paul, MN, four pages.
Anonymous (2003). "3MTM Steri-StripTM Adhesive Skin Closures," 3M HealthCare Brochure, twelve pages.
Anonymous. (2005). "3MTM TegadermTM Family of Transparent Dressings," 3M HealthCare Brochure, six pages.
Anonymous. (2006). "Avocet Polymer Technologies," located at <http://www.avocetcorp.com/index.html>, last visited on Nov. 5, 2007, one page.
Anonymous. (2006). "Avogel Scar Hydrogel," located at <http://www.avocetcorp.com/avogel_scar_hydrogel.html>, last visited on Nov. 5, 2007, two pages.
Anonymous. (2006). "Avosil Ointment," located at <http://www.avocetcorp.com/avosil.html>, last visited on Nov. 5, 2007, three pages.
Anonymous. (Date Unknown). "Mepiform Instructions of Use," Tendra Corporation Brochure, two pages.
Anonymous. (Date Unknown). "Silicone Scar Bandage: Standard Wound Healing Application," located at <http://www.thejamushop.com/silicon_sheet_for_keloids.htm>, last visited on Mar. 18, 2009, four pages.
Brace, "Definition of Brace", Merriam Webster, Available Online at <www.merriam-webster.com>, 2015, 4 pages.
Canica Design Inc. (Date Unknown). "ABRA® Abdominal Wall Closure Set," located at < http://www.canica.com/instructions/1D1544RA%20-%20ABRA%20CWK08%20IFU.pdf>, last visited on Sep. 10, 2009, pp. 1-11.
Canica Design Inc. (Date Unknown). "ABRA® Surgical Skin Closure Set," located at <http://www.canica.com/instructions/1D0830RH.pdf>, last visited on Sep. 10, 2009, pp. 1-4.
English translation of in OA for Application No. 6583/DELNP/2013, dated May 12, 2019.
Extended European Search Report dated Aug. 19, 2013 for European Patent Application No. 10 808 724.8, filed on Aug. 11, 2010, 8 pages.
Mask, "Definition of Mask", Merriam Webster, Available Online at <www.merriam-webster.com>, 2015, 4 pages.
Nahabedian, M.Y. (Dec. 2005). "Scar Wars: Optimizing Outcomes with Reduction Mammaplasty," Plastic and Reconstructive Surgery, 116(7):2026-2029.
NHSSB Wound Management Manual, Northern Health and Social Services Board, 2005, pp. 1-97.
Office Action (no EN translation) for CR Application No. 2013-0356, dated Jun. 24, 2019.
Office Action (no Eng. translation) for Br Application No. 1120130175060, dated Aug. 11, 2020.
Office Action for BR Application No. 1120130175060, dated Sep. 19, 2019.
Shanghai Dongyue Medical Health Product Co., Ltd. (2005). Silicon-gel Membrane—Scar Bandage, located at <http://www.shdongyue.com/cp/shaos/shaos02b.asp>, last visited on Nov. 6, 2008, two pages.
Smith & Nephew. (Date Unknown). "CICA-CARE. Silicone Gel Sheeting," located at <http://wound.smith-nepehew.com/za/Product/asp?NodeId=569&Tab=5&hide=True>, last visited on Jun. 9, 2009, one page.
U.S. Appl. No. 16/728,454 titled "Skin Treatment Devices" filed Dec. 27, 2019.
Wound Care Technologies. (2008). "DERMACloseTM RC: Continuous External Tissue Expander, Brochure No. PL-0020-F," located at < http://www.woundcaretech.com/sell-sheet.pdf>, last visited on Sep. 10, 2009, two pages.
Wound Care Technologies. (2008). "Instructions for Use. DERMACloseTM RC, Brochure No. DR-0079-A," located at < http://www.dermaclose.com/instructions.pdf>, last visited on Sep. 10, 2009, two pages.
3M Medical, 3M Medical. (2006). "They Say Every Scar Tells a Story," 3M HealthCare: St. Paul, MN, one page.
Aarabi, et al., Aarabi, S. et al. (Oct. 2007). "Mechanical Load Initiates Hypertrophic Scar Formation Through Decreased Cellular Apoptosis," The FASEB Journal 21(12):3250-3261.
Al-Attar, et al., Al-Attar, A. et al. (Jan. 2006). "Keloid Pathogenesis and Treatment," Plastic and Reconstructive Surgery 117(1): 286-300.
Angelini, et al., Angelini, G.D. et al. (1984). "Comparative Study of Leg Wound Skin Closure in Coronary Artery Bypass Graft Operations," Thorax 39:942-945.
Atkinson, et al., (Nov. 2005). "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery 116(6)., 1648-1656.
Bachert, et al., Bachert, B. et al. (2003). "Probing Elastic Modulus and Depth of a Two Layer Human Skin Model with Piezoelectric Cantilevers," Biomedical Engineering Senior Design Team, Drexel University, 27 pages.
Berman, et al., Berman, B. et al. (Mar. 3, 2005). "Keloid and Hypertrophic Scar," located at <http://www.emedicine.com/DERM/topic205.htm>, last visited on Nov. 19, 2007, 23 pages.
Bunker, Bunker, T.D. (1983). "Problems with the Use of Op-Site Sutureless Skin Closures in Orthopaedic Procedures," Annals of the Royal College of Surgeons of England 65:260-262.
Burd, et al., Burd, A. et al. (Dec. 2005). "Hypertrophic Response and Keloid Diathesis: Two Very Different Forms of Scar," Plastic and Reconstructive Surgery 116(7):150-157.
Chen, et al., Chen, H-H. et al. (Jul. 2001). "Prospective Study Comparing Wounds Closed With Tape With Sutured Wounds in Colorectal Surgery," Arch. Surg. 136:801-803.
Davison, et al., Davison, S.P. et al. (Jan. 2006). "Ineffective Treatment of Keloids with Interferon Alpha-2b," Plastic and Reconstructive Surgery 117(1):247-252.
Escoffier, et al., Escoffier, C. et al. (Sep. 1989). "Age-Related Mechanical Properties of Human Skin: An In Vivo Study," J. Invest. Dermatol, 9(3)3:353-357.
Evans, et al., Evans, S.L. et al. (2009). "Measuring the Mechanical Properties of Human Skin in vivo Using Digital Correlation and Finite Element Modeling," J. Strain Analysis 44:337-345.
Fairclough, et al., Fairclough, J.A. et al. (1987). "The Use of Sterile Adhesive Tape in the Closure of Arthroscopic Puncture Wounds: A Comparison with a Single Layer Nylon Closure," Annals of the Royal College of Surgeons of England 69:140-141.
Gorney, Gorney, M. (Mar. 2006). "Scar: The Trigger to the Claim," Plastic and Reconstructive Surgery 117(3):1036-1037.
Hof, et al., Hof, M. et al. (Jul. 2006). "Comparing Silicone Pressure-Sensitive Adhesives to Silicone Gels for Transdermal Drug Delivery," presented at 33 Annual Meeting and Exposition of the Controlled Release Society, Vienna, Austria, Jul. 22-26, 2006, seven pages.
Koval, et al., Koval, K.J. et al. (Oct. 2003). "Tape Blisters Following Hip Surgery. A Prospective Randomized Study of Two Types of Tape," The Journal of Bone and Joint Surgery, 85-5(10):1884-1887.

(56) References Cited

OTHER PUBLICATIONS

Kuo, et al., Kuo, F. et al. (May 2006). "Prospective Randomized, Blinded Study of a New Wound Closure Film Versus Cutaneous Suture for Surgical Wound Closure," Dermatological Surgery 32(5):676-681.

Mustoe, et al., Mustoe, T.A.,et al. (Nov. 2005). "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery 116.6, 1657-1658.

O'Brien, et al., O'Brien, L. et al. (2009). "Silicon Gel Sheeting for Preventing and Treating Hypertrophic and Keloid Scars," The Cochrane Collaboration, pp. 1-47.

Pitcher, Pitcher, D. (Feb. 1983). "Sutureless Skin Closure for Pacemaker Implantation: Comparison with Subcuticular Suture," Postgraduate Medical Journal 59:83-85.

Shirado, et al., "Realization of Human Skin-Like Texture by Emulating Surface Shape Pattern and Elastic Structure," presented at Symposium on Haptic Interfaces for Virtual Environment and Teleoperator Systems 2006, Mar. 25-26, 2006, Alexandria, VA, pp. 295-296.

Sullivan, et al., Sullivan, S.R. et al. (2007). "Acute Wound Care," Chapter 7 in ACS Surgery: Principles and Practice, 24 pages.

Teot, Téot, L. (2005). "Scar Control" European Tissue Repair Society, located at <http://www.etrs.org/bulletin12_1/section11.php>, last visited on Nov. 30, 2007, 13 pages.

Vaughan, et al., Vaughan, P. et al. (2006). "Optimal Closure of Surgical Wounds in Forefoot Surgery: Are Adhesive Strips Beneficial?" Acta Orthop. Belg. 72(6):731-733.

Vowden, Vowden, K. (Mar. 2003). "Wound Management. Policy and Resource Pack," Bradford Teaching Hospitals NHS Foundation Trust, pp. 1-70.

Watson, Watson, G.M. (1983). "Op-Site Skin Closure: A Comparison with Subcuticular and Interrupted Sutures," Annals of the Royal College of Surgeons of England 65:83-84.

Webster, et al., Webster, D.J.T. et al. (Sep. 1975). "Closure of Abdominal Wounds by Adhesive Strips: A Clinical Trial," British Medical Journal 20:696-698.

Westaby, Westaby, S. (1980). "Evaluation of a New Product for Sutureless Skin Closure," Annals of the Royal College of Surgeons of England 62:129-132.

\* cited by examiner

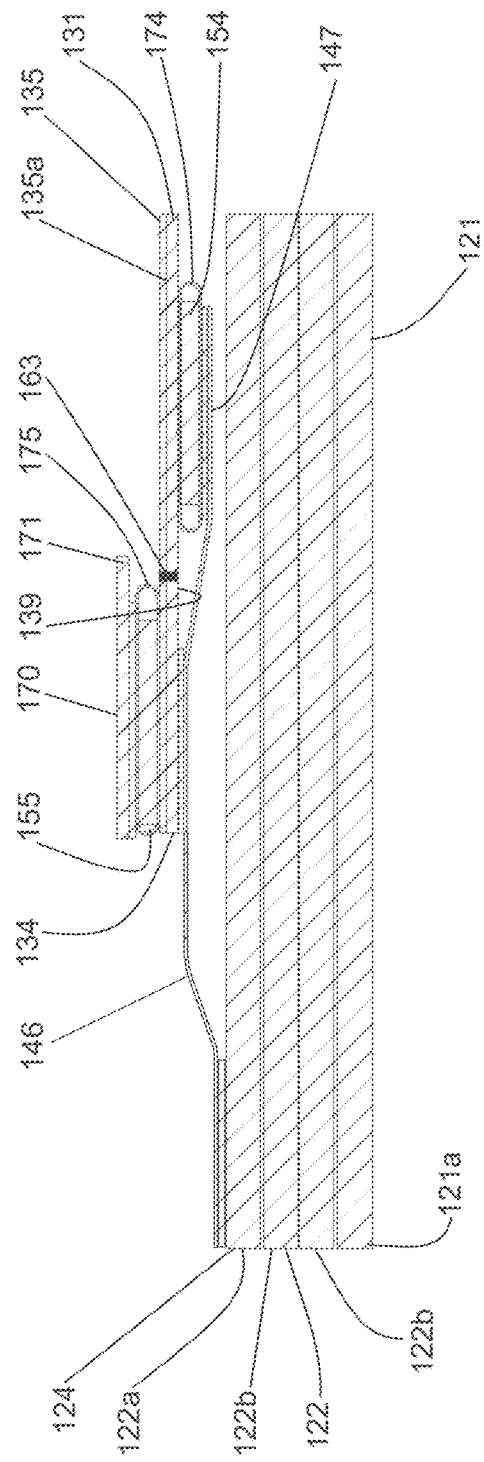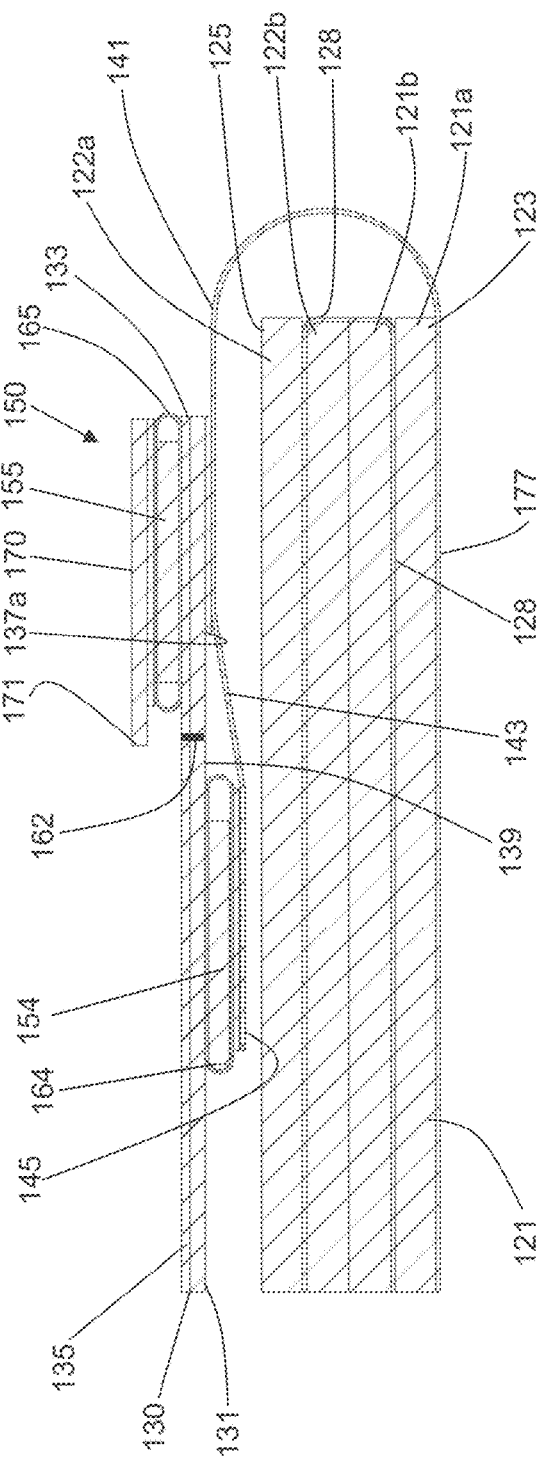

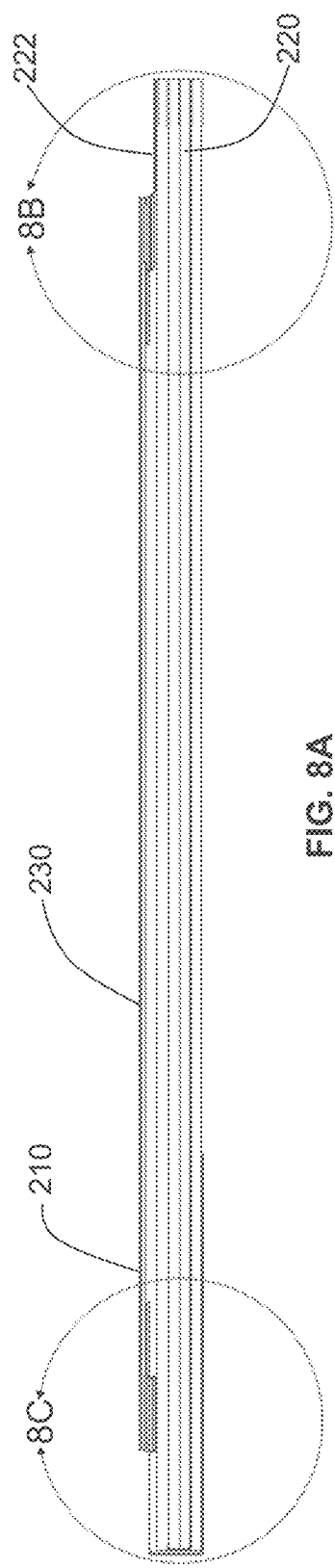
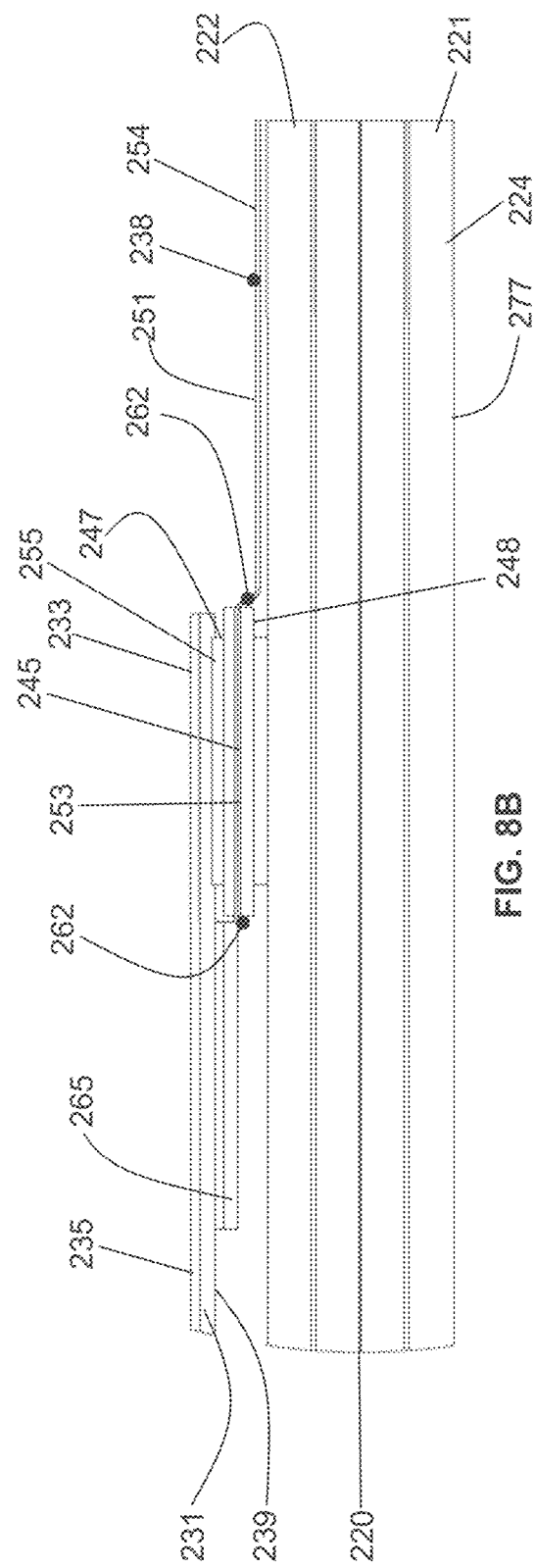
FIG. 8A
FIG. 8B

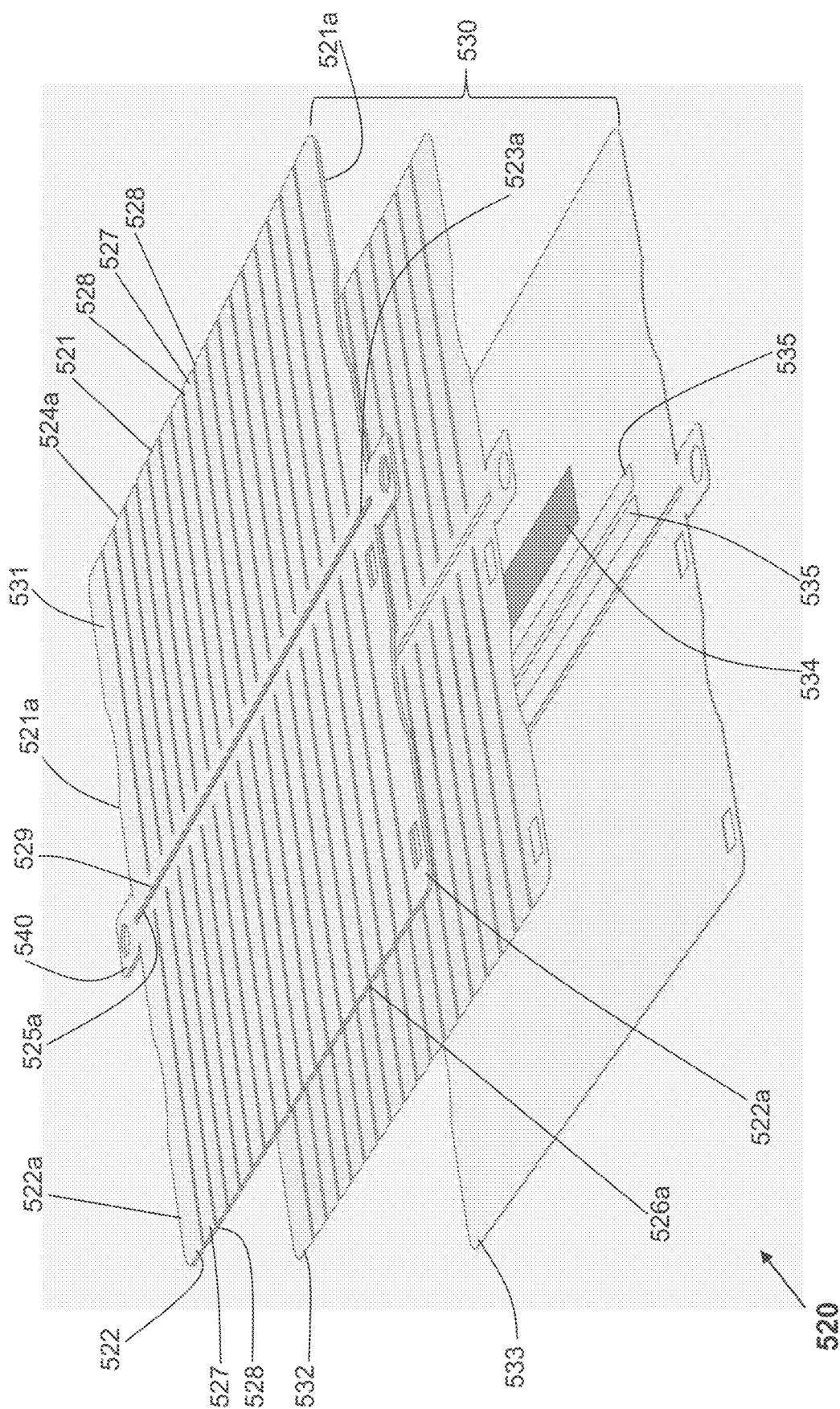

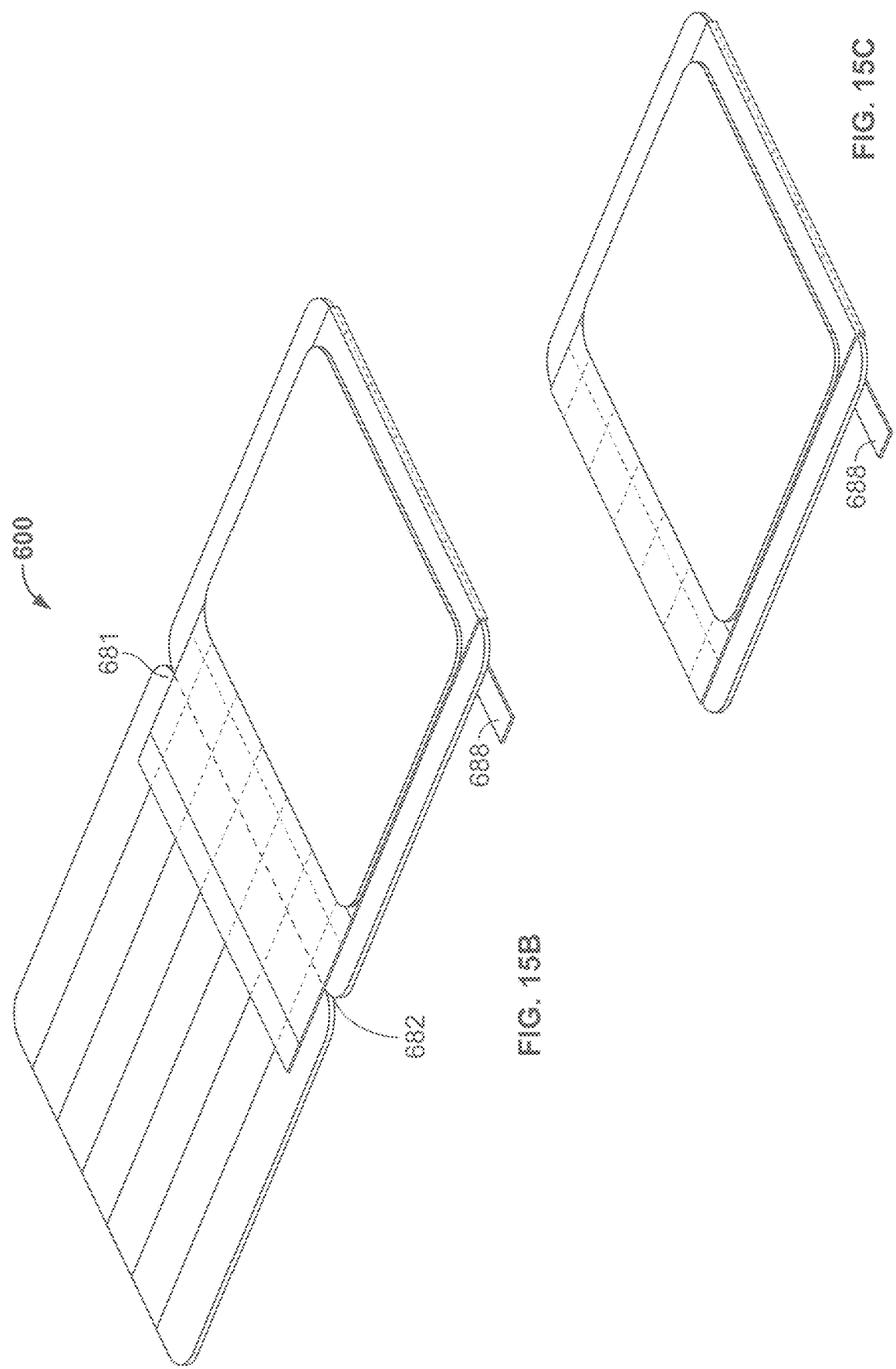

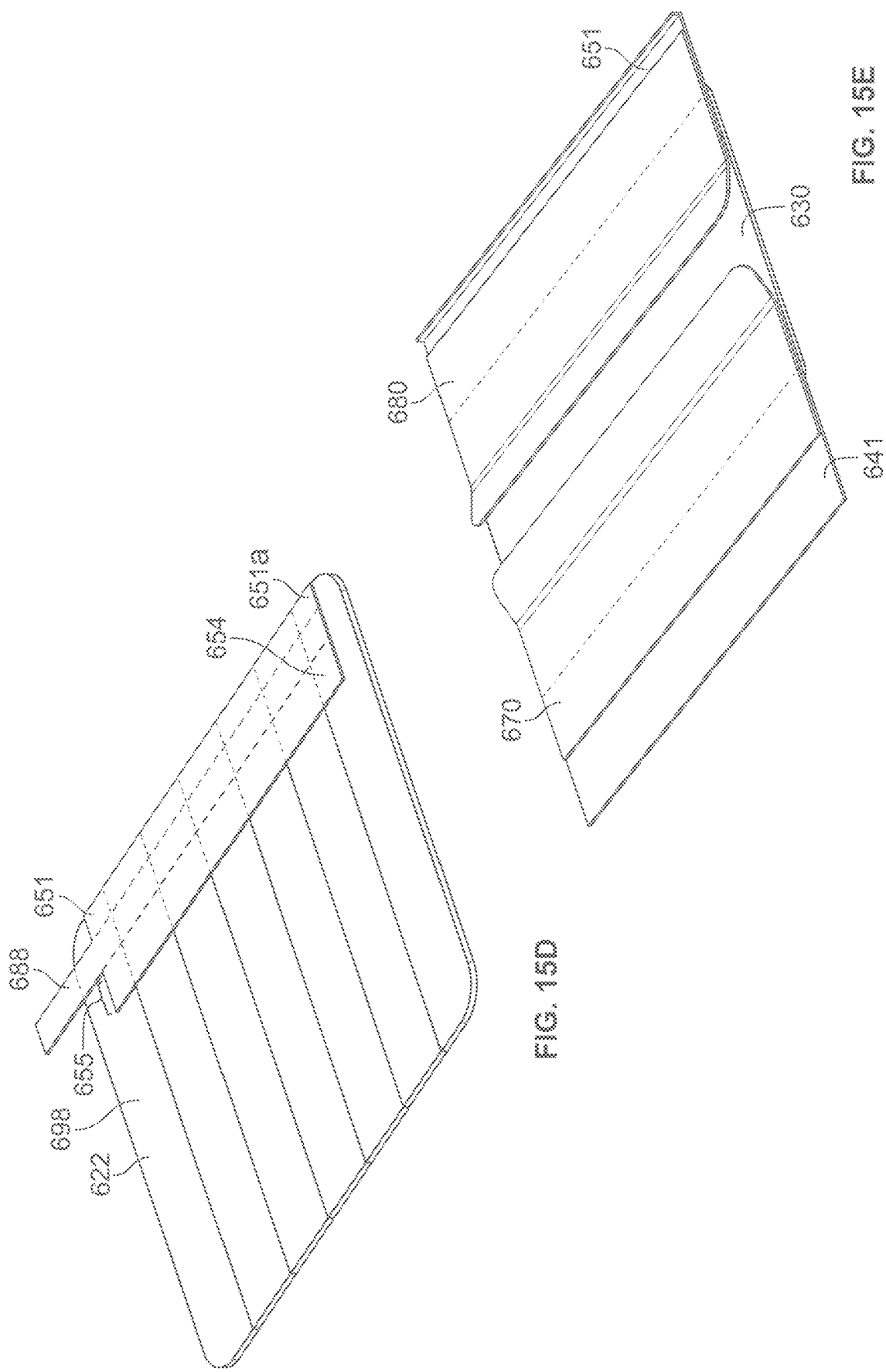

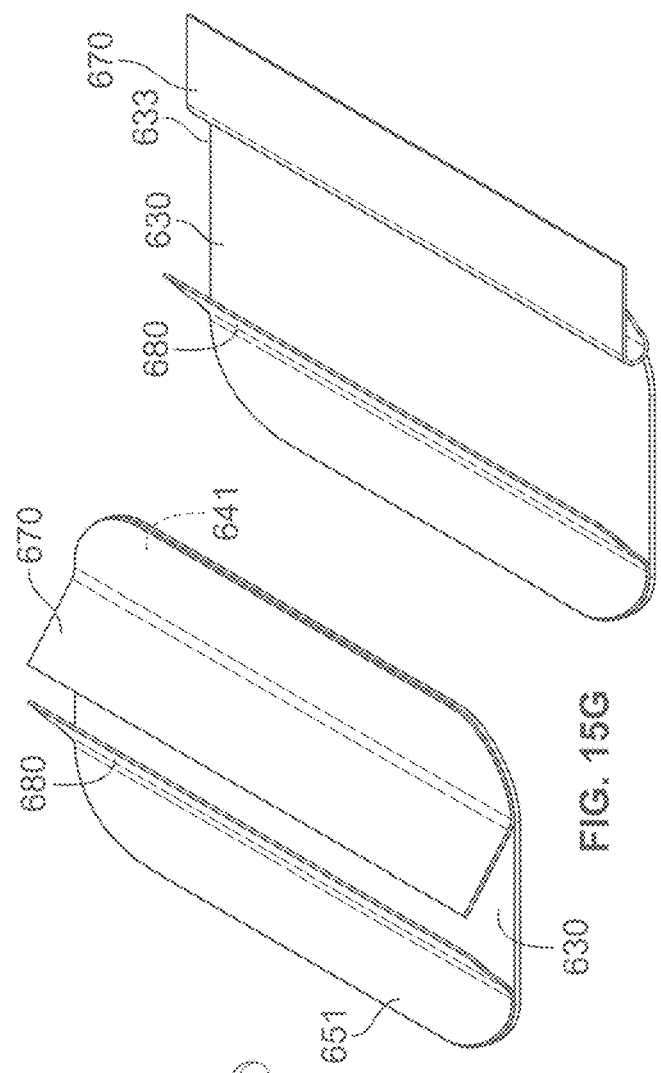
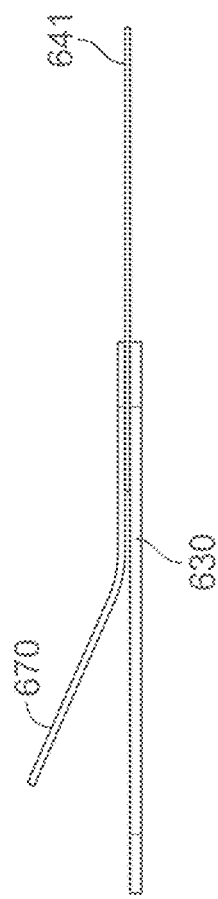
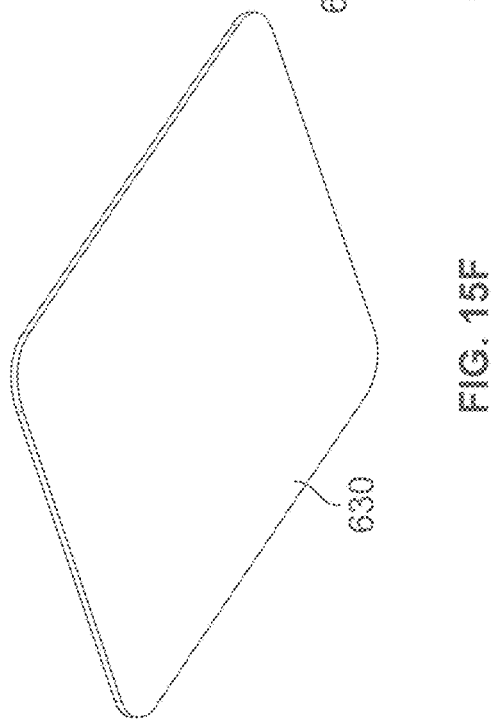
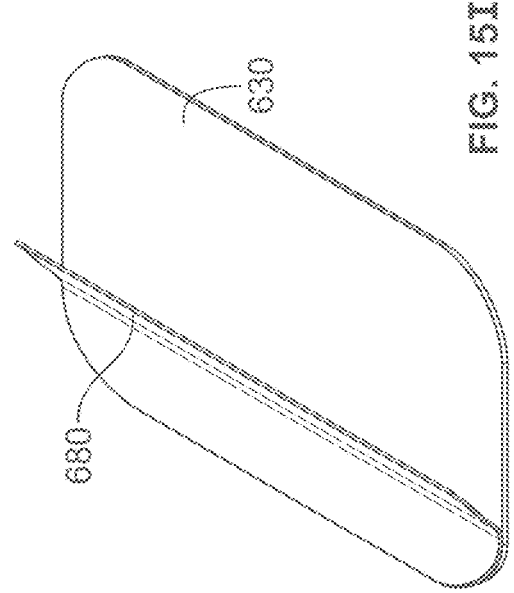

WOUND OR SKIN TREATMENT DEVICES AND METHODS

CROSS-REFERENCE TO RELATED APPLICATIONS

This application is a continuation of U.S. application Ser. No. 13/789,264, filed on Mar. 7, 2013, now issued as U.S. Pat. No. 9,844,470, which is a continuation of U.S. application Ser. No. 13/345,524, filed on Jan. 6, 1012, now issued as U.S. Pat. No. 9,248,048 which claims benefit under 35 U.S.C. § 119(e) to U.S. Provisional Application Ser. No. 61/430,908, filed on Jan. 7, 2011 and to U.S. Provisional Application Ser. No. 61/443,647, filed on Feb. 16, 2011, and U.S. application Ser. No. 13/789,264 is a continuation-in-part of U.S. application Ser. No. 12/854,859, filed on Aug. 11, 2010, now issued as U.S. Pat. No. 8,592,640 all of which are hereby incorporated by reference in their entirety. This application is also related to U.S. application Ser. No. 11/888,978, filed on Aug. 3, 2007, now issued as U.S. Pat. No. 7,683,234 which is hereby incorporated by reference in its entirety.

BACKGROUND

Scar formation in response to cutaneous injury is part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage, the previously constructed and randomly organized matrix is remodeled into an organized structure that is highly cross-linked and aligned to increase mechanical strength.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Typically, these scars are raised and are characterized by the random distribution of tissue bundles. The appearance (i.e., size, shape, and color) of these scars varies depending on the part of the body in which they form, and the underlying ethnicity of the person affected. Hypertrophic scars are very common, and may occur following any full thickness injury to the skin. Recently, it has been shown in U.S. Patent Application Publication 2006/0037091 (U.S. patent application Ser. No. 11/135,992 entitled "Method for Producing Hypertrophic Scarring Animal Model for Identification of Agents for Prevention and Treatment of Human Hypertrophic Scarring," filed May 24, 2005) which is hereby incorporated by reference in its entirety, that mechanical stress may increase hypertrophic scarring in a murine model.

Keloids are typically characterized as tumors consisting of highly hyperplastic masses that occur in the dermis and adjacent subcutaneous tissue in susceptible individuals, most commonly following trauma. Keloids are often more severe than hypertrophic scars, since they tend to invade normal adjacent tissue, while hypertrophic scars tend to remain confined within the original scar border.

BRIEF SUMMARY

Devices, kits and methods described herein may be for treatment of a subject at a skin site including without limitation for wound treatment or the treatment, amelioration, or prevention of scars and/or keloids, by manipulating mechanical or physical properties of skin or by shielding skin from stresses, and/or by controllably stressing or straining the epidermis and layers of dermal tissue at or near a skin site, i.e., at or adjacent a wound or a treatment site of a subject's skin. According to variations, manipulating mechanical or physical properties may thereby modulate tensile or compressive stress at the skin site. The stress at the skin site may be reduced to levels below that experienced by normal skin and tissue. The stress at the skin site may be increased to levels above that experienced by normal skin and tissue. The stress or strain may be applied to surrounding tissue in one, two, or more directions to manipulate endogenous or exogenous stress at the skin site in one, two or more directions. According to variations, devices and methods described herein may reduce or otherwise manipulate the stress experienced by skin and/or a wound and surrounding tissues in order to treat a subject. The devices may also assist in preventing or reducing the incidence of wound dehiscence.

According to the devices, kits and methods described herein, a skin treatment device, skin device, wound treatment device, scar or keloid treatment device, scar or keloid amelioration or prevention device, bandage, or dressing may be provided that may be applied, attached to or coupled to one or more layers of the skin or tissue of a subject (hereinafter referred to as "dressing", "skin device" or "skin treatment device").

In addition to amelioration of scar formation, other uses for such skin treatment device may or may not include without limitation, for example, treating skin related conditions such as acne, blemishes, rosacea, warts, rashes (including but not limited to erythematous, macular, papular and/or bullous conditions), psoriasis, skin irritation/sensitivity, allodynia, telangiectasia, port wine stains and other arteriovenous malformations, and ectopic dermatitis; treating or improving existing scars, wrinkles, stretch marks, loose or sagging skin or other skin irregularities; lifting, pinning, holding, moving skin for various purposes such as during pre-operative preparation, during surgical procedures for example as a low-profile tissue retractor, to stabilize blood vessels during needle or catheter insertion, postoperatively, pre or post operatively for pre-treating or preconditioning skin for example, prior to scar revision, wound incision, body contouring, in mastectomy skin expansion, aesthetic skin treatment or resurfacing whether topical or subdermal, whether or not using an energy modality such as, for example, microwave, radio-frequency ablation, high-intensity focused ultrasound, laser, Infrared, incoherent light, during weight loss, or for aesthetic purposes; hair removal or hair loss; treating and/or closing skin injuries for example, incisions, wounds, chronic wounds, bed sores, ulcers (including venous stasis ulcers), preventing or reducing the incidence of wound dehiscence, diabetic skin or wound conditions, burn healing and/or relief; acting as an occlusive or negative-pressure wound dressing; protecting incisions or wounds, e.g. prevention of splitting or opening, protecting newborn belly buttons after cutting umbilical cord. Such treatments may include use of a drug or other therapeutic agent that may be applied to the skin with such device. The agents may include but are not limited to antibiotics, antifungals, immune modulators including corticosteroids and non-steroidal immune modulators. The agents may be provided in any of a variety of formulations, including but not limited powders, gels, lotions, creams, pastes, suspensions, etc. The devices may also be used for purposes of delivering a drug to the skin or through the skin, for example by stretching the skin and applying a drug thereto. Different configurations of the device may be amenable to the size or geometry of different body regions. The treatments may be applied to regions of any shape (e.g. linear, curved, stellate), size or depth, and to one or more regions of the body, including but not limited to the scalp, forehead, face (e.g. nose, eyelid, cheeks, lips, chin), ears, neck, shoulder, upper arm, lower arm, palm, dorsum of the hand, fingers, nailbed, axilla, chest, nipple, areola, back, abdomen, inguinal region, buttocks, perineal region, labia, penis, scrotum, thigh, lower leg, plantar surface of the foot, dorsal surface of the foot, and/or toes. Such devices may also be referred to herein as a "dressing", "skin device" or "skin treatment device".

In some situations, an immediate, quick or simple application of a dressing may be desired. Devices, kits and methods described herein may be for the preparation and/or application of a dressing to the skin and the separation of the applicator, tensioning device or dressing carrier, support or base from the skin device.

The devices, kits or methods described herein may include a packaging, carrier, support, base, applicator or tensioning device, each of which may: contain, hold, carry or support a dressing at least temporarily; may be used to prepare a dressing for application; may be used to deliver, orient or apply a dressing; may be used to maintain a dressing in a stressed or strained configuration; may be used to stress or strain a dressing; may be used to separate the dressing from the packaging, carrier, support, base, applicator or tensioning device and/or may be used during or after application of a dressing to provide additional treatment to a wound, incision or other treatment location; and/or may be used to apply pressure to a wound, incision or other treatment location. According to some variations, a packaging and/or applicator may provide structural support for a dressing while or after an adhesive liner is released. According to some variations, the assembly may be constructed to avoid folding or bending of the dressing to the extent that the adhesive on the dressing sticks to itself. For example, when some variations of the dressing are held or supported at one point or along one edge of the dressing in a cantilever configuration, the dressings will not bow, laterally deform, or otherwise deform out of plane, under their own mass or configuration.

In some other variations of the devices and methods herein, a device with a substantially rigid support structure or that provides structural support to a dressing and that provides a particular resistance to bending or column strength when two opposing edges of the device and support structure are placed under a compressive load that causes axial compression or lateral deformation, e.g. a force similar to a hand grasping force is applied to an edge of the device, before the device buckles or folds. For example, a resistance to bending may be characterized as the peak force that is achieve as the device and support structure are compressed without compressed by 25% of its original dimension. This column strength or rigidity may vary, depending upon the direction along the device and support structure being measured. In some further variations, the peak force may be at least about 0.02 Newtons per millimeter (N/mm), about 0.03 N/mm, about 0.05 N/mm, about 0.1 N/mm, about 0.15 N/mm, about 0.2 N/mm, about 0.3 N/mm, about 0.4 N/mm or about 0.5 N/mm. In some variations of devices comprising generally flat or planar devices and support structures having a thickness, the peak force may be measured by applying a compressive force along the shortest dimension of the device/support structure that is transverse to the thickness of the device/support structure. According to such variations, the device may have an aspect ratio of length to width that is greater than 1:1, 2:1 or 3:1, for example.

A resistance to bending in the direction of dressing strain may also be measured by three-point bending, applying a transverse force to the midpoint of the applicator simply supported on two outer points at a given distance apart or support span. For example, the distance between the two points of a sample may be approximately 0.75 inches and a force that ranges from about 1 to 1.25 pounds may be applied to a sample approximately 0.35 inches in width resulting in a deflection of approximately 0.05 inches. A resistance to bending may also be measured by characterizing the force at which buckling occurs on a simply supported beam. For example, a force of approximately 0.45 pounds may be applied to a simply supported sample approximately 0.35 inches in width and may result in a deflection of approximately 0.004 inches. The resistance to bending may also be characterized by the strain of the outer surface before fracture or permanent deformation. By taking measurements of the support structure and the deflections during the test procedure, a load deflection curve may be generated and the flexural modulus of the support structure may also be calculated. In some variations, the support structure may comprise a flexural modulus of at least about 0.9 GPa, while in other embodiments, the flexural modulus is at least about 1 GPa, at least about 1.1 GPa, at least about 1.2 GPa, at least about 1.3 GPa, or at least about 1.4 GPa.

In another example, a device of 7 cm wide by 19 cm long may be configured with a support structure comprising a paperboard, support sheet or support structure. The support structure may have an average thickness in the range of about 0.008" to about 0.028" or greater. In some specific variations, the support structure may have a thickness of about 0.012", about 0.016", about 0.018", about 0.024", about 0.28" or about 0.032", about 0.036", about 0.04", about 0.05" or greater. Upon the application of force along the lengthwise edge of the 19 centimeter length, i.e. across the 7 cm width of the device, the support structure may provide sufficient rigidity or column strength to achieve peak forces of about 3 pound or more, 4 pounds or more, or of about 10 pounds or more, while being compressed, collapsed, bowed, buckled or otherwise deformed by 25% along its 7 cm width (i.e. about 1.75 cm). In some variations, the support structure may comprise scoring or regions of reduced thickness to permit some bending it at least one direction or in both directions.

According to some variations, a device that provides structural support may have a plurality or supporting cross elements or segments extending from one edge of the length to an opposing edge or the length (or from one edge of a width to an opposing edge of a width); According to some variations there may be three or more cross elements, e.g., a cross element extending along two opposing edges and transversely across a width (or a length) and one or more cross elements extending across the width (or length) and between the cross elements along the two opposing edges.

Such cross elements may or may not be coupled or connected to each other, for example, with a relatively flexible material. Such cross elements may have a total aggregate width with respect to the length of an opposing edge of about 20% or more, about 25% or more, about 30% or more, or about 35% or more. According to some variations, one or more cross elements may be provided that have a total aggregate width, relative to the length of the opposing side, between about 20% to 100%. Such cross elements may be segmented and may provide flexibility when bending in a direction and rigidity relative to the flexibility, in another direction.

The packaging and/or applicator may also provide structural support or stability of the dressing as it is oriented and/or applied to the skin of a subject. According to some variations, the dressing and packaging is configured to be pre-oriented in a position facing a wound before or after the wound device is prepared for application, e.g., the adhesive liner is removed. According to some variations, the packaging or applicator is configured to be used with one hand to orient and/or apply the device to the skin of a subject. For example, in some situations, particularly where a longer or larger dressing is used, a packaging or applicator provides structural support for a dressing such that a user can effectively hold onto, manipulate and/or apply a prepared dressing with one-hand. According to some variations, the assembly comprises a support structure. A dressing support structure is defined herein to mean a structure that is coupled whether directly or indirectly, to a back surface of a dressing that is to be applied to a subject. The support structure may further comprise at least in part, a material or structure that is more rigid than the dressing to be applied to a subject. The support structure may comprise one or more elements or segments. It may be constructed of a single substrate, a laminate or a plurality of elements coupled together and/or to the dressing. According to some variations at least 20%, 25%, 30%, 35%, or 40% of a length or width of the dressing is supported by one or more support structures extending from a first opposing side to an opposite side along a length or width of the dressing. In some further variations, the percentage of a length or width that is supported by the support structure(s) is a minimum average of support across the entire length or entire width of the device, e.g. at least a 20%, 25%, 30%, 35% or 40% average support across an entire dimension of the device, e.g. length or width. According to some variations, an entire area of a dressing is supported by a support structure. According to some variations, a base, carrier or support of a dressing may comprise at least three support structures extending transversely between opposing sides of the dressing. According to some variations, a support structure comprises interconnected members or elements. According to some variations, a base, carrier or support remains coupled to the dressing as it is applied. According to some variations, greater structural support is provided to a dressing carrier, support or base in a first direction while greater flexibility is provided in a second direction, while lesser flexibility is in the first direction and lesser structural support is provided in the second direction. According to some variations, one or more support structures may extend beyond an edge of the first opposing side. According to some variations, one or more support structures, at least in part, may extend beyond at least a portion of an edge of a first opposing side and at least in part beyond at least a portion of an edge of an opposite side. According to some variations, a support structure may extend at least 3 mm from at least a portion of an edge of the dressing. According to some variations, the packaging or applicator is configured to improve a sterile transfer of a dressing to a wound of a subject. According to variations, the packaging or applicator may be sufficiently wider or longer, or have a sufficiently larger area than a dressing providing the ability to maneuver or manipulate the support or applicator so that it provides sterile application and/or one-handed application without the need to touch the dressing. According to some variations, a margin of distance is provided from the outer edges of the dressing carrier, support or base to the dressing supported on the base or adhesive on the dressing. Such margins may be selected to prevent or resist a user from touching the dressing or dressing adhesive when grasping the edges to manipulate the dressing carrier, support, applicator or base.

Devices, kits and methods described herein may be for the treatment, amelioration, or prevention of scars and/or keloids by creating and/or maintaining a predetermined strain in an elastic skin treatment device that is then affixed to the skin surface using skin adhesives to transfer a generally planar (e.g. compressive) force from the bandage to the skin surface.

In some variations, a dressing is provided, comprising an elastic sheet structure (e.g., a comprising a silicone polyurethane, TPE (thermoplastic elastomers), synthetic rubber or co-polyester material) comprising an upper surface, a lower surface, a first edge and a second edge opposite the first edge, and one or more adhesive regions. The dressing may further comprise a first release liner releasably attached to the adhesive region or regions. The adhesive region(s) may comprise a pressure sensitive adhesive. The dressing may be tapered or otherwise shaped to reduce skin tension at the edges. The dressing may have modified, reduced or no adhesive near its edges to reduce skin tension at the edges. Portions of the dressing may be unstrained and may thereby reduce strain in certain areas of the skin where the dressing is applied. In some specific examples, the unstrained area or areas are found between the edges of the dressing and the strained area(s). In some further examples, the unstrained areas are limited to this area and are not found, during application or use, between the strained areas of a single dressing, in use. In still further examples, the unstrained areas are limited to areas along the edges of a dressing that intersect the strain axis of the strained area(s), but not to areas along the edges of the dressing that are generally parallel to the strain axis.

A packaging device, dressing carrier, dressing support, dressing base, applicator and/or tensioning device may be provided. The packaging device, dressing carrier, dressing support, dressing base, applicator and/or tensioning device may be configured to stress and/or strain a dressing prior to application to a subject. A device may be used to strain and/or maintain a strain on a dressing. In one variation, a dressing is provided, comprising a first device attachment structure, zone or region, a second device attachment structure, zone or region, and a structure or mechanism configured to exert a separation force between the first and second device attachment structures, zones or regions. The device may further comprise a releasable locking mechanism, attachment mechanism or adhesive, configured to maintain the member or mechanism in a strained configuration.

In some situations, application of a compressive force to a wound is desirable to reduce bleeding. According to some variations, the packaging, carrier, support, base, applicator or tensioning device described herein may be further used to help reduce bleeding, e.g., by allowing application of a compressive force using the device while or after the dressing is applied. A coagulative additive may also be provided on a dressing.

According to one aspect, the packaging, carrier, support, base, applicator and/or tensioning device may be sufficiently rigid or supportive in at least one direction, to hold a dressing's form so that it is easy to manipulate.

According to some variations, the packaging is also sufficiently flexible in at least one direction to permit curving or shaping of the dressing to conform to the curvature or shape of the location on the body or skin where the dressing is applied. Generally, the flexibility of the packaging used to conform the dressing to the treatment site may be configured so that the treatment site is not substantially deformed during the application of the dressing; so that the application of the dressing is relatively smooth or uniform on the skin; and/or provides a uniform, predetermined, or relatively predictable strain or force to an area of skin. The packaging or applicator may have flexibility in a first direction and greater rigidity in another direction. The packaging or applicator may include elements or segments that permit flexibility with respect to adjacent elements or segments.

According to some variations, the packaging is also sufficiently flexible in at least one direction to permit curving or shaping of the dressing to conform to the curvature or shape of the location on the body or skin where the dressing is applied. Generally, the flexibility of the packaging used to conform the dressing to the treatment site may be configured so that the treatment site is not substantially deformed during the application of the dressing; and/or so that the application of the dressing is relatively smooth or uniform on the skin; and/or provides a uniform, predetermined, or relatively predictable strain and/or force to an area of skin. The packaging or applicator may have flexibility in a first direction and greater rigidity in a second direction. The first direction may be transverse to the direction of straining or have a component that is transverse to the direction of straining. The second direction may by the direction of straining or have a component that is in the direction of straining. The first direction may or may not be transverse with respect to the second direction. The packaging or applicator may include elements or segments that permit flexibility with respect to adjacent elements or segments.

According to some variations a desired flexibility, for example having at least one component transverse to the direction of straining, may be characterized by a modified cantilevered beam bending model, i.e. applying a force to the free end of a beam, simply supported from the other end, while wrapping it around a cylindrical object with a known radius of curvature or curvature, defined as the reciprocal of the radius of the curvature. According to one variation, the force to bend the packaging or applicator around an object with a predetermined curvature may be no greater than about 3 pounds. According to one variation, the force may be no greater than about 0.3 pounds. According to one variation, the force to bend around a predetermined curvature of about a 2.5 inch radius may be no greater than about 3 pounds. In another variation, the force to bend around a predetermined curvature of about a 2.5 inch radius may be no greater than about 0.3 pounds.

According to some variations, a packaging, applicator or tensioning device is provided comprising a base having an inner surface to which a dressing is removably attached, and a cover or lid having an inner surface interfacing the inner surface of the base when in an initial closed configuration. According to some variations, the base and cover are coupled at corresponding edges along their corresponding lengths to form a book-like structure whereby the cover may be rotated with respect to the base to open the device. Alternatively the cover may be lifted off of the base. According to variations, a liner is attached to the cover and will expose an adhesive side of a dressing when the cover is lifted or opened.

In some variations, the book-like structure, in the closed configuration, comprises a layered structure comprising a cover/lid, a treatment device and a base, in that relative order, while in the open configuration, the relative order of the layered structure changes to a cover/lid, a base, and a treatment device. The treatment device may also comprise one or more release layers. In one variation, in the closed configuration, a first face of the cover/lid is in contact with a first face of the treatment device, and a first face of the base is in contact with the second surface of the treatment device opposite the first surface, while in the open configuration, a second face of the cover/lid (opposite the first face of the cover/lid) is in contact with a second face of the base (opposite the first face of the base) but not with the first face of the treatment device. In some variations, the cover/lid may be separated from the base during or after tensioning of the treatment device. In some variations, the treatment device may be attached asymmetrically to the book-like structure, relative to the bending region of the book-like structure. In some instances, the asymmetric attachment may provide the user with a mechanical advantage when tensioning the dressing, and/or may reduce manufacturing costs by optimizing the amount of elastic material used in the dressing. In other variations, the dressing or skin treatment device may be attached symmetrically to the book-like structure, relative to the bending region of the book-like structure.

In another embodiment, a method of applying a dressing to a surface is provided. According to some variations the method may comprise providing a dressing packaging comprising: an applicator comprising a base structure having an inner surface and a manipulation portion; a dressing comprising a first surface configured to be applied to a skin or wound of a subject; and a back surface, wherein the back surface of the dressing is removably coupled or anchored to the inner surface of the base structure, and wherein the first surface faces away from the inner surface of the base structure; and a cover configured to removably cover the first surface of the dressing. A method may further comprise removing the cover to expose a first surface of a dressing; and using the manipulation portion of the base structure to apply the first surface of the dressing to a wound or skin of a subject. In another variation, a method for treating a wound is provided, comprising straining an inner region of an elastic bandage between a first unstrained region and a second unstrained region, and attaching at least the strained inner region of the dressing to a skin site or both strained and unstrained regions.

According to some variations, a dressing packaging assembly comprises: a base structure having an inner surface; a cover structure having an opposing surface, wherein the base structure is movably coupled to the cover structure; and a dressing comprising a first surface configured to be applied to a wound or skin of a subject, and a back surface, wherein at least a portion of the back surface is removably coupled to the inner surface of the base structure; and wherein the cover structure is configured to move from a first position where the opposing surface interfaces with and is substantially parallel to the first surface to the dressing to a second position where the opposing surface is separated from the first surface of the dressing. According to variations, the first surface of the dressing comprises an adhesive region. According to variations the first surface of the dressing comprises an adhesive backing interfacing an adhesive region on the dressing. According to variations, the opposing surface of the cover structure comprises an adhesive backing covering the adhesive region when the cover structure is in the first position and separated from the adhesive region when the cover structure is in the second position. According to variations, the dressing comprises an elastic material. According to variations, the dressing comprises a first attachment region coupled to the inner surface of the base structure and a second attachment region coupled to the opposing surface of the cover structure, wherein the cover and base are configured to exert a straining force to strain the dressing when the cover is moved from the first position to the second position. According to variations, a tensioning structure is configured to exert the straining force on the dressing. According to variations, the tensioning structure comprises: a first structure configured to couple the dressing at the first attachment region to the inner surface of the base structure; and a second structure configured to couple the dressing at the second attachment region to the opposing surface of the cover; wherein the tensioning structure is configured to exert the straining force to the dressing between the first attachment region and the second attachment region when the cover structure is moved with respect to the base structure from the first position to the second position. According to some variations, the dressing has a first width when the cover is in the first position and a second width when the cover is in the second position, wherein the second width is greater than the first width. According to variations, the second width is at least 20% greater than the first width. According to variations, the second width is at least 40% great than the first width. According to variations, the base structure comprise at least one relatively rigid element and at least one relatively flexible element, wherein the relatively rigid element is sufficiently rigid to support the dressing when the straining force is applied in a first direction; and wherein the relatively flexible element permits the base structure to flex in a second direction. According to variations, the at least one relatively rigid element comprises a plurality of flexible coupled, relatively rigid elements. According to variations, the cover structure comprises at least one relatively rigid element and at least one relatively flexible element. According to variations, a release device is configured to release the dressing from the base structure after the dressing is applied to a wound or skin of a subject. According to some variations, base structure is pivotably coupled to the cover structure.

According to variations, a dressing packaging assembly comprises: a base structure having an inner surface and comprising at least one support element and at least one flexible element; and a dressing comprising a first surface configured to be applied to a wound or skin of a subject, and a back surface, wherein at least a portion of the back surface is removably coupled to the inner surface of the base structure. According to variations, the at least one rigid element comprises a plurality of rigid elements coupled to each other with the at least one flexible element. According to variations, a cover structure comprises an opposing surface configured to interface with the first surface of the dressing, wherein the cover structure is moveably coupled to the base structure to move from a first position where the opposing surface interfaces with the first surface of the dressing, to a second position where the cover is separated from the first surface of the dressing. According to variations, the cover structure is pivotably coupled to the base structure. According to variations, the cover structure comprises at least one support element and at least one flexible element sufficiently flexible to permit shaping of the cover structure. According to variations, the first surface of the dressing comprises an adhesive region. According to variations, the first surface of the dressing comprises an adhesive backing interfacing an adhesive region on the dressing. According to variations, the opposing surface of the cover structure comprises an adhesive backing covering the adhesive region in the first position and separated from the adhesive region in the second position. According to variations, the dressing comprises and elastic material. According to variations, the dressing comprises a first attachment region coupled to the inner surface of the base structure and a second attachment region coupled to the opposing surface of the cover structure, wherein the cover and base are configured to exert a straining force to strain the dressing when the cover is moved from the first position to the second position. According to variations, the assembly further comprises a tensioning structure configured to exert the straining force on the dressing. According to variations, the tensioning structure comprises: a first structure configured to couple the dressing at the first attachment region to the inner surface of the base structure; and a second structure configured to couple the dressing at the second attachment region to the opposing surface of the cover; wherein the tensioning structure is configured to exert the straining force to the dressing between the first attachment region and the second attachment region when the cover structure is moved with respect to the base structure from the first position to the second position. According to variations, the dressing between the first and second attachment regions has a first width when the cover is in the first position and a second width when the cover is in the second position, wherein the second width is greater than the first width. According to variations, the second width is at least 4% greater than the first width. According to variations, the second width is at least 20% greater than the first width. According to variations, the second width is at least 40% great than the first width.

According to variation, a method of applying a dressing to a wound or skin of a subject comprises: providing a dressing packaging assembly comprising: a base structure having an inner surface; a cover structure having an opposing surface, wherein the base structure is movably coupled to the cover structure; and a dressing comprising a first surface including an adhesive region, and a back surface, wherein at least a portion of the back surface is removably coupled to the inner surface of the base structure, and wherein the opposing surface of the cover structure comprises an adhesive backing covering the adhesive region when the cover structure is in the first position; pivoting the cover structure with respect to the base structure to a second position to separate the opposing surface from the first surface of the dressing and to separate the adhesive backing from the adhesive region;

applying the first surface of the dressing to a wound or skin of a subject, then subsequently releasing the dressing from the base structure. According to variations of the method, at least a portion of the back surface of the dressing is coupled to the cover structure and further comprising pivoting the cover structure with respect to the base structure to strain the dressing.

According to variations, a dressing applicator comprises a first dressing attachment region and a second dressing attachment region comprising a variable separation distance between the first dressing attachment region and the second dressing attachment region, and a bending region between the first dressing attachment region and the second dressing attachment region that alters the variable separation distance, and wherein a first distance from a center of the bending region to the first dressing attachment area is different from a second distance from the center of the bending region to the second dressing attachment area.

According to variations, a dressing tensioning device comprises: a dressing carrier comprising a first carrier edge and a second opposing carrier edge defining a carrier width therebetween; a tensioning element configured to move with respect to the dressing carrier from a first position to a second dressing tensioning position; and a dressing assembly comprising a dressing including a first dressing edge coupled to the carrier adjacent the first carrier edge; a second dressing edge coupled to an attachment element wherein the attachment element coupled to the tensioning element; wherein in the first position of the tensioning element, the second dressing edge is a first distance from the second carrier edge within the width of the carrier, and in the second position of the tensioning element, the second dressing edge is a second distance from the second carrier edge within the width of the carrier, wherein the first distance is greater than the second distance. According to variations, the first dressing edge is relatively fixed with respect to the second dressing edge when the tensioning element is moved between the first and second positions.

According to variations, a dressing packaging assembly comprises: a base structure having an inner surface; a cover structure having an opposing surface, wherein the base structure is movably coupled to the cover structure; and a dressing comprising a first surface configured to be applied to a wound or skin of a subject, and a back surface, wherein at least a portion of the back surface is removably coupled to the inner surface of the base structure; wherein the cover structure is configured to move from a first position where the opposing surface interfaces with the first surface to the dressing to a second position where the opposing surface is separated from the first surface of the dressing where the second position is at least about 180 degrees rotated with respect to the first position. According to variations, the first surface of the dressing comprises an adhesive region. According to variations, the first surface of the dressing comprises an adhesive backing interfacing an adhesive region on the dressing. According to variations, the opposing surface of the cover structure comprises an adhesive backing covering the adhesive region when the cover structure is in the first position and separated from the adhesive region when the cover structure is in the second position. According to variations, the dressing comprises an elastic material. According to variations, the dressing comprises a first attachment region coupled to the inner surface of the base structure and a second attachment region coupled to the opposing surface of the cover structure, wherein the cover and base are configured to exert a straining force to strain the dressing when the cover is moved from the first position to the second position. According to variations, the assembly further comprises a tensioning structure configured to exert the straining force on the dressing. According to variations, the tensioning structure comprises: a first structure configured to couple the dressing at the first attachment region to the inner surface of the base structure; and a second structure configured to couple the dressing at the second attachment region to the opposing surface of the cover; wherein the tensioning structure is configured to exert the straining force to the dressing between the first attachment region and the second attachment region when the cover structure is moved with respect to the base structure from the first position to the second position. According to variations, the dressing has a first width when the cover is in the first position and a second width when the cover is in the second position, wherein the second width is greater than the first width. According to variations, the second width is at least 20% greater than the first width. According to variations, the second width is at least 40% great than the first width. According to variations, the base structure comprises at least one relatively rigid element and at least one relatively flexible element, wherein the relatively rigid element is sufficiently rigid to support the dressing when the straining force is applied in a first direction; and wherein the relatively flexible element permits the base structure to flex in a second direction.

According to variations, a dressing packaging comprises: a dressing carrier comprising a first carrier edge, a second carrier edge opposing the first carrier edge, and a support structure extending between the first edge and the second edge, configured to support a dressing during application of the dressing to a subject; and a dressing comprising a first dressing edge, a second dressing edge opposing the first dressing edge, a back surface and an opposing skin interfacing surface, wherein at least a portion of the back surface is removably coupled to the dressing carrier wherein the first dressing edge and the second dressing edge are positioned between the first carrier edge and the second carrier edge, and wherein the first dressing edge defines a first margin between the first dressing edge and the first carrier edge and the second dressing edge defines a second margin between the second dressing edge and the second carrier edge, wherein each of the first and second margins have a width of at least three millimeters.

In one variation, a dressing system is provided, comprising a first support, a second support, and a primary bending region therebetween, the primary bending region comprising a primary bending axis, and a treatment device comprising a first attachment region attached to the first support and a second attachment region attached to the second support, a first separation region configured to separate from first attachment region and a second separation region configured to separate from the second attachment region. The first and second separation regions may comprise perforations. The dressing system may further comprise a pull element located along the perforations. The treatment device may be asymmetrically attached to the first and second supports, relative the primary bending region. A first distance between the first support and the primary bending axis may be different from a second distance between the second support and the primary bending axis. The dressing system may further comprise a closed configuration wherein the treatment device is located between the first support and the second support, and a closed configuration wherein the second support is located between the first support and the treatment device. The second support may comprise at least one secondary bend region comprising a secondary bending axis that is not parallel to the primary bending axis. The secondary bending axis may be orthogonal to the primary bending axis. The first support may comprise at least one secondary bend region comprising a secondary bending axis that is not parallel to the primary bending axis. The at least one secondary bend region of the first support may be aligned with the at least one secondary bend region of the second support. The treatment device may further comprise a release liner coupled to an adhesive surface of the treatment device. The treatment device may comprise a perforation region. The dressing system may further comprise an elongate element attached adjacent to the perforation region. The elongate element may protrude beyond the perforation region of the treatment device. In some variations, at least a portion of the elongate element may be folded, and the fold may be along a substantial length of the treatment device. At least one of the first and second supports may comprise indicia identifying a center region of the treatment device. The indicia may comprise a recessed edge, ink mark, embossing, or window. The primary bending region may also perforated. The first support may be configured to detach from the second support and the treatment device, and may or may not do so while maintaining the treatment device in a strained configuration. The second support may comprise an adhesive element configured to adhere to the treatment device when the dressing system is in the open configuration but not in the closed configuration. The first support may comprise an attached release liner. The release liner may be attached to the first support between an outer edge of the first support and the attached treatment device. An inner surface of the first and/or second support facing the treatment device may include an adhesive, such as an adhesive coating or adhesive tape, which is configured to maintain the treatment device either in a tensioned state as it is stretched and contacts the adhesive, and/or to maintain the treatment device against the first and/or second supports.

In another variation, a dressing system is provided, comprising a first tensioning member, a second tensioning member, and a primary bending region therebetween, the primary bending region comprising a primary bending axis, and a treatment device asymmetrically attached to the first and second tensioning members, relative the primary bending region. The treatment device may comprises a first end attached to the first tensioning member and a second end attached to a second tensioning member, wherein a first distance between the first tensioning member and the primary bending axis is different from a second distance between the second tensioning member and the primary bending axis. The dressing system may further comprise a closed configuration wherein the treatment device is located between the first tensioning member and the second tensioning member, and an open configuration wherein the second tensioning member is located between the first tensioning member and the treatment device. The second tensioning member may comprise at least one secondary bend region comprising a secondary bending axis that is not parallel to the primary bending axis. The secondary bending axis may be orthogonal to the primary bending axis. The first tensioning member may comprise at least one secondary bend region comprising a secondary bending axis that is not parallel to the primary bending axis. The at least one secondary bend region of the first tensioning member may be aligned with the at least one secondary bend region of the second tensioning member. The treatment device may further comprise a release liner coupled to an adhesive surface of the treatment device. The treatment device may comprise a perforation region. The dressing system may further comprise an elongate element attached adjacent to the perforation region. The elongate element may protrude beyond the perforation region of the treatment device. In some variations, at least a portion of the elongate element may be folded, and the fold may be along a substantial length of the treatment device. At least one of the first and second tensioning members may comprise indicia identifying a center region of the treatment device. The indicia may comprise a recessed edge, ink mark, embossing, or window. The primary bending region may be perforated. The first tensioning member may be configured to detach from the second tensioning member and the treatment device. The first tensioning member may be configured to detach from the second tensioning member and the treatment device while maintaining the treatment device in a strained configuration. The second tensioning member may comprise an adhesive element configured to adhere to the treatment device when the dressing system is in the open configuration but not in the closed configuration. The first tensioning member may comprise an attached release liner. The release liner may be attached to the first tensioning member between an outer edge of the first tensioning member and the attached treatment device.

In another variation, a dressing system is provided, comprising a first applicator member, a second applicator member, and a primary bending region therebetween, the primary bending region comprising a primary bending axis, and a treatment device attached to the first and second applicator members, wherein the dressing system comprises a closed configuration wherein the treatment device is located between the first applicator member and the second applicator member, and a closed configuration wherein the second applicator member is located between the first applicator member and the treatment device. The second applicator member may comprise at least one secondary bend region comprising a secondary bending axis that is not parallel to the primary bending axis. The secondary bending axis may be orthogonal to the primary bending axis. The first applicator member may comprise at least one secondary bend region comprising a secondary bending axis that is not parallel to the primary bending axis. The at least one secondary bend region of the first applicator member may be aligned with the at least one secondary bend region of the second applicator member. The treatment device may further comprise a release liner coupled to an adhesive surface of the treatment device. The treatment device may comprise a perforation region. The dressing system may further comprise an elongate element attached adjacent to the perforation region. The elongate element may protrude beyond the perforation region of the treatment device. At least a portion of the elongate element may be folded, and the fold may be along a substantial length of the treatment device. At least one of the first and second applicator members may comprise indicia identifying a center region of the treatment device. The indicia may comprise a recessed edge, ink mark, embossing, or window. The primary bending region may be perforated. The first applicator member is configured to detach from the second applicator member and the treatment device. The first applicator member may be configured to detach from the second applicator member and the treatment device while maintaining the treatment device in a strained configuration. The second applicator member may comprise an adhesive element configured to adhere to the treatment device when the dressing system is in the open configuration but not in the closed configuration. The first applicator member may comprise an attached release liner. The release liner may be attached to the first applicator member between an outer edge of the first applicator member and the attached treatment device.

BRIEF DESCRIPTION OF THE DRAWINGS

FIG. 5B is a cross section of FIG. 5A along the lines C-C.

FIG. 5C is a cross section of FIG. 5A along the lines D-D.

FIG. 8A is a schematic end view of the dressing and packaging assembly of FIG. 7 in a strained configuration with the cover open at about 360 degrees from a closed configuration.

FIG. 8B is an expanded view of section 8B of FIG. 8A.

FIG. 14 is an exploded perspective view of a packaging device in an open configuration.

FIG. 15B is a bottom 15F perspective view of the dressing and packaging assembly of FIG. 15A in a strained configuration.

FIG. 15C is a bottom perspective view of the dressing and packaging assembly of FIG. 15 A after removing the cover of the carrier, support or base.

FIG. 15D is a top perspective view of the device of FIG. 15A after removing the cover of the carrier, support or base.

FIG. 15E is a top perspective view of the device of FIG. 15A after removing the carrier, support or base.

FIG. 15F is a perspective view of a strained dressing after it is separated from the attachment sheets.

FIG. 15G is a perspective view of a dressing assembly with attachment sheets.

FIG. 15H is a perspective view of the dressing assembly of FIG. 15G with an attachment sheet peeled back.

FIG. 15I is a perspective view of the dressing assembly of FIG. 15G with an attachment sheet removed.

FIG. 15J is a cross section of the dressing assembly with attachment sheets of FIG. 15G.

DETAILED DESCRIPTION

Figure 1:
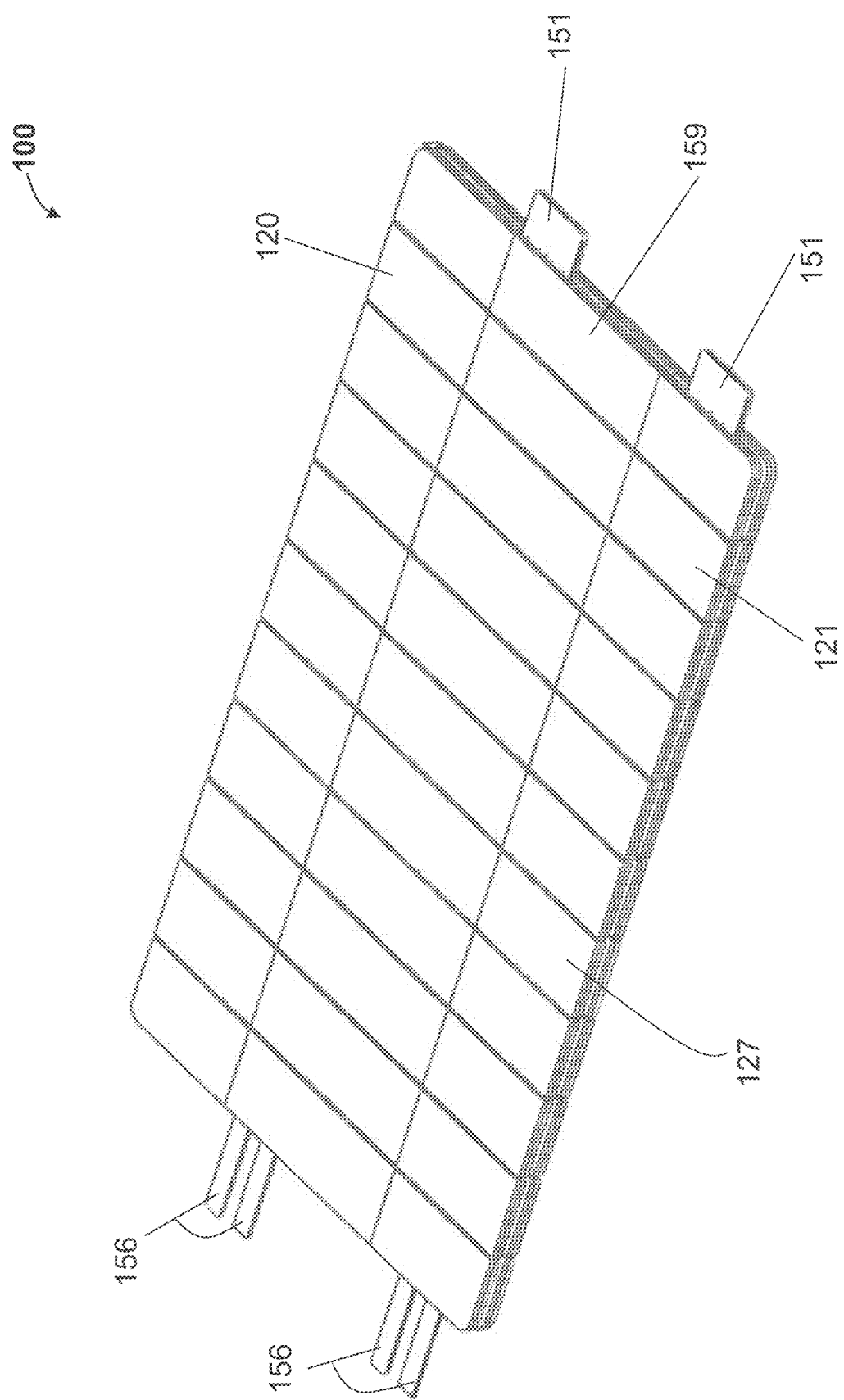
FIG. 1 is a perspective view of a variation of a dressing and packaging assembly in a closed configuration.

Previous attempts to treat scars and keloids have included surgery, silicone dressings, steroids, x-ray irradiation, and cryotherapy. Each of these techniques has disadvantages. Perhaps the biggest disadvantage is that none of them effectively prevent or ameliorate the formation of scars or keloids in the first instance. That is, these techniques have primarily been used to treat scars after they are already well established.

Unloading of exogenous and/or endogenous stress in the vicinity of the wound may ameliorate the formation of scars, hypertrophic scars, or keloids. The mechanical environment of an injury may be an important factor in tissue response to that injury. The mechanical environment includes exogenous stress (i.e., physiological stress which includes stress transferred to the wound via muscle action or physical body movement) and endogenous stress (i.e., dermal stress originating from the physical properties of the skin itself, including stress induced at the wound site due to swelling or contraction of the skin). The devices, dressings, kits and methods described herein may control or regulate the mechanical environment of a skin including but not limited to the mechanical environment of a wound. The devices, dressings, kits and methods described herein may also control or regulate the mechanical environment to ameliorate scar and/or keloid formation. The mechanical environment of skin may include stress, strain, or any combination of stress and strain. The control of a wound's mechanical environment may be active or passive, dynamic (e.g., by applying an oscillating stress) or static. The stresses and strains acting on the wound may involve the layers of the skin, such as the outer stratum corneum, the epidermis and dermis, as well as the underlying connective tissue layers, such as the subcutaneous fat. Devices and methods described here may shield a wound from its mechanical environment. The term "shield" is meant to encompass the unloading of stress experienced by the wound as well as providing a physical barrier against contact, contaminants, and the like. The devices and methods described here may shield a wound by unloading the wound and surrounding tissues from endogenous stress and/or exogenous stress. Thus, devices and methods described here may reduce the stress experienced by a wound and surrounding tissues to a lower level than that experienced by normal skin and tissue. Unloading of exogenous and/or endogenous stress in the vicinity of the wound may ameliorate the formation of scars, hypertrophic scars, or keloids.

A cell's external mechanical environment may trigger biological responses inside the cells and change cell behavior. Cells can sense and respond to changes in their mechanical environment using integrin, an integral membrane protein in the plasma membrane of cells, and intracellular pathways. The intracellular pathways are initiated by receptors attached to cell membranes and the cell membrane that can sense mechanical forces. For example, mechanical forces can induce secretion of cytokines, chemokines, growth factors, and other biologically active compounds that can increase or trigger the inflammatory response. Such secretions can act in the cells that secrete them (intracrine), on the cells that secrete them (autocrine), on cells surrounding the cells that secrete them (paracrine), or act at a distance from the point of secretion (endocrine). Intracrine interference can alter cell signaling, which can in turn alter cell behavior and biology including the recruitment of cells to the wound, proliferation of cells at the wound, and cell death in the wound. In addition, the extracellular matrix may be affected.

As noted above, the wound healing process may be characterized in three stages: early inflammatory phase, the proliferative phase, and remodeling. The inflammatory phase occurs immediately after injury and typically lasts about two days to one week. Blood clotting takes place to halt blood loss and factors are released to attract cells that can remove debris, bacteria and damaged tissue from the wound. In addition, factors are released to initiate the proliferative phase of wound healing. In the proliferative phase, which lasts about four days to several weeks, fibroblasts grow and build a new extracellular matrix by secreting collagen and proteoglycans. At the end of the proliferative phase, fibroblasts can act to contract the wound further. In the remodeling phase, randomly oriented collagen is organized and crosslinked along skin tension lines. Cells that are no longer needed can undergo apoptosis. The remodeling phase may continue for many weeks or months, or indefinitely after injury. Scars typically reach about 75-80% of normal skin breaking strength about 6-8 weeks after injury. In general, scars typically have a triangular cross-section. That is, a scar is usually smallest in volume near the skin surface (i.e., stratum corneum and epidermis) and increases in volume as it progresses into the deeper layers of the dermis.

There are three common possible outcomes to a wound healing process. First, a normal scar can result. Second, a pathologic increase in scar formation can result, such as formation of a hypertrophic scar or a keloid. Third, the wound may not heal completely and become a chronic wound or ulcer. The devices, kits and methods described herein can ameliorate the formation of any type of scar. In addition, the devices, kits and methods described here can be adapted for a variety of wound sizes, and for different thicknesses of skin, e.g., the devices may be configured for use in different areas of the body. In addition, the devices, kits and methods described here can be adapted to ameliorate scar formation in any type of skin, e.g., body location, age, race, or condition.

Without wishing to be bound by any particular theory, we believe that mechanical strain acting on a wound or incision early in the proliferative phase of the wound healing process may inhibit cellular apoptosis, leading to a significant accumulation of cells and matrix, and hence increased scarring or the production of hypertrophic scars. Given the underlying similarities between hypertrophic scars and keloids with respect to excessive matrix formation, we believe that the devices and methods described herein may also be useful in preventing and treating keloids by offloading or neutralizing at least some of the strain that may be acting on the wound or incision. This tensile strain may be exogenous and/or endogenous strain, and may include but is not limited to the strain from the intrinsic tensile forces found in normal intact skin tissue.

A number of wound dressings have backings, adhesive liners and/or packaging that are removed prior to application of a wound dressing. Many existing dressings can be clumsy to orient and apply and can have a tendency to fold and adhere to themselves.

Devices, kits and methods described herein may treat skin at a skin site ("skin treatment device"), including without limitation, to ameliorate the formation of scars at wound sites by controllably stressing or straining the epidermis and deeper layers of dermal tissue at or near a skin site, i.e., at or adjacent a wound or treatment site of a subject's skin, thereby reducing tensile or compressive stress at the skin site. The stress at the skin site may be reduced to levels below that experienced by normal skin and tissue. The stress or strain may be applied to surrounding tissue in one, two, or more directions to reduce endogenous or exogenous stress at the skin site in one, two or more directions. Thus, devices and methods described herein may reduce the stress experienced by skin and/or a wound and surrounding tissues in order to treat a subject. The device may also assist in preventing or reducing the incidence of wound dehiscence.

Devices, kits and methods described herein may provide a packaging and/or applicator for a dressing. According to one variation, the packaging and/or applicator is configured to provide quick or easy preparation and/or application of a dressing. While some examples herein specifically refer to a packaging that also acts as a tensioning device to pre-strain a dressing, other dressings that are not pre-strained and/or strained prior to application may be provided in accordance with one or more variations or embodiments. The packaging may also operate as an applicator where one or more elements of the packaging may be used to position and/or apply the dressing to the skin of a subject.

Devices kits and methods described herein may be for the preparation and/or application of a dressing. Such preparation may include but is not limited to, for example, removal of an adhesive liner, straining or tensioning a dressing, orienting a dressing for application and/or applying a medicament or other material to a portion of the dressing prior to application.

Backings, adhesive liners or release layers, and/or other packaging may provide some structural stability to a flexible wound dressing. However, when removed, the flexible wound dressing can be somewhat clumsy to use because it may fold and adhere to itself or the user, or otherwise provide for difficult positioning over the wound. Also the act of pulling or removing the liner and reorienting the dressing to the patient may increase the tendency to fold or flop. Furthermore, because of the folding or floppiness of the dressing, during adhesive removal and subsequent reorientation, the user has a significant possibility of compromising the sterility of a portion of the device to be applied to a wound site.

According to another variation, a packaging or applicator is configured to provide support for the dressing after the dressing is prepared and while the dressing is applied to a subject. According to some variations, a backing provides structural support or stability of the dressing as and/or after an adhesive liner is released. According to some variations, a dressing and packaging is configured to be pre-oriented in a position facing a wound. i.e., for immediate application when and after the wound device is prepared for application. According to some variations, the packaging applicator is configured to be used with one hand to orient and/or apply the device to the skin of a subject.

According to some variations, the packaging dressing carrier, support, base tensioning device or applicator tensioning device and/or applicator provide a release mechanism to separate the applied dressing from the packaging and/or applicator after the dressing is applied to the skin. According to a variation, a dressing may be prestrained and coupled to a dressing carrier, support, base tensioning device or applicator, for example as set forth in U.S. Provisional Application Ser. No. 61/512,340 filed on Jul. 17, 2011 and incorporated in its entirety herein by reference. One or more dressing releases described herein may be used with a dressing carrier, support, base tensioning device or applicator.

In some further variations, the dressing or one or more adhesive regions of the dressing may be released, i.e., separated, from the liner by opening a packaging or applicator. According to some variations, a book-like packaging is provided with a cover, and a base to which a dressing is removably attached. When or as the cover is opened, the liner may be manually or automatically released from the adhesive of the dressing. According to variations, a liner is attached to the cover and will expose an adhesive side of a dressing when the cover is lifted or opened. The base may be configured to provide structural support to the dressing while the liner is removed and/or while the dressing is applied to the skin of a subject.

According to some variations, the packaging, tensioning device, dressing carrier, support, base or applicator may further comprise an opening, a window, or a clear or semi-opaque portion through which a wound, incision or other location may be visualized as the dressing is applied to the skin. According to some variations, the window guides the application of a dressing so that there is an optimal or desired distance between the wound and the edges of the dressing and/or so that the dressing is in an optimal location for unloading skin stresses.

According to some variations the applicator, tensioning device, packaging or carrier, support, or base may provide varied or variable flexibility to allow the dressing to be shaped when applied to various body locations or contours.

According to some variations, a packaging or applicator is more rigid or provides sufficient column strength in at least a first direction to be supportive of a dressing, while being relatively more flexible and less rigid in at least second direction to provide for a more conforming application to a curved or shaped skin surface of a subject or to permit curvature or shaping of the dressing where it is applied. The first and second directions may or may not be orthogonal to each other. According to some variations, a packaging applicator, tensioning device or dressing carrier, support or base is sufficiently rigid or supportive of a dressing while permitting shaping of the dressing, According to some variations, the carrier or support which may include a base and/or a cover may comprise segments of relatively more rigid material flexibly coupled to adjacent segments to provide flexibility to permit shaping of packaging/applicator and/or dressing while providing sufficient support of the dressing during application. According to some variations, segments are coupled to adjacent segments by way of a flexible material, such as a low-density polyethylene (LDPE) material, or a composite of adhesive and a thinner more flexible substrate. Alternatively, segments may be formed as a structure by manufacturing a substrate with cut-outs, slots, grooves, scoring or other openings or variations in thickness of the substrate at different locations.

The packaging, applicator, tensioning device, or dressing carrier may have elements or features the provide flexibility in one direction orthogonal to the plane of the support while limiting flexibility in another direction orthogonal to the plane of the support. According to some variations, the flexible elements may limit flexibility when the device is being strained and permit flexibility when the device is being applied to the skin. Each of the elements may permit flexing in a different direction than one or more of the other elements. Flexible elements may be straight, or shaped according to a desired application or location of placement.

According to variations, flexible elements are provided in combination with support elements that provide sufficient support to allow a user to maintain the dressing in a strained configuration. According to variations, one or more elements may be provided to maintain a strained dressing in a strained configuration, for example a securing element that secures the dressing in a strained configuration until it is applied to a subject and is released from the carrier, support, base tensioning device or applicator. For example, after straining the dressing, the dressing may be adhered or attached to one or more elements of a dressing, support, base tensioning device or applicator or dressing assembly until it is released from the carrier, support, base tensioning device or applicator or assembly.

According to some variations, the applicator may be further used to help reduce bleeding, e.g., by allowing application of a compressive force using a support structure while or after the device is applied. One or more hemostatic or coagulative agents may be applied to, or otherwise integrated with dressing to help reduce bleeding. Potential agents include chitosan, calcium-loaded zeolite, microfibrillar collagen, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g. II, VII, VII, X, XIII, Von Willebrand factor), procoagulants (e.g. propyl gallate), antifibrinolytics (e.g. epsilon aminocaproic acid), and the like. In some variations, the agents may be freeze-dried and integrated into the dressing and activated upon contact with blood or other fluid. In some further variations, an activating agent may be applied to the dressing or the treatment site before the dressing is used on the subject. In still other examples, the hemostatic agent may be applied separately and directly to the wound before application of the dressing, or after application to the dressing via a catheter or tube. The devices may also comprise one or more other active agents that may be useful in aiding in some aspect of the wound healing process. For example, the active agent may be a pharmaceutical compound, a protein (e.g., a growth factor), a vitamin (e.g., vitamin E), or combinations thereof. A further example of such medicament may include, but is not limited to various antibiotics (including but not limited to cephalosporins, bactitracin, polyxyxin B sulfate, neomycin, polysporin), antiseptics (such as iodine solutions, silver sulfadiazine, chlorhexidine), antifungals (such as nystatin), antiproliferative agents (sirolimus, tacrolimus, zotarolimus, biolimus, paclitaxel), grow factors (such as VEGF) and other treatments (e.g. botulism toxin. Of course, the devices may comprise more than one medicament or agent, and the devices may deliver one or more medicaments or agents.

According to one variation, the applicator and or packaging may be sufficiently supportive or rigid to hold a dressing's form so that it is easy to manipulate. According to a variation, the applicator may be sufficiently wider and/or longer or have a sufficiently larger area than a dressing so that it may provide sterile application and/or one-handed application. According to variations, a support structure is provided for a dressing. According to a variation, a margin is provided as a support structure between the dressing or dressing adhesive and one or more edge portions of the support structure. Such margins provide a supported edge or area to grasp or manipulate the dressing or its carrier, base or support, without necessitating or creating a greater likelihood of inadvertent user contact with the adhesive.

According to some variations, the packaging or applicator may also be used to strain a dressing prior to application to provide a dressing configured to ameliorate scar or keloid formation.

Devices are described here that may be used for ameliorating the formation of scars and/or keloids at a skin or wound site. The scars may be any type of scar, e.g., a normal scar, a hypertrophic scar, etc. In general, the devices may be configured to be removably secured to a skin surface near a wound. The devices may shield the skin or wound from endogenous stress and/or exogenous stress. In some variations, the devices may shield the skin or wound from endogenous stress without affecting exogenous stress on the skin or wound, e.g., devices that modify the elastic properties of the skin, etc. In other variations, the devices may shield the skin or wound from exogenous stress without affecting endogenous stress on the wound. Such variations may include situations where the musculature and surrounding skin or wound tissue has been paralyzed, e.g., through the use of botulinum toxin or the like. In still other variations, the devices shield the skin or wound from both endogenous and exogenous stress.

The devices or dressings described herein may treat skin at a skin site including without limitation to ameliorate the formation of scars at wound sites by controllably stressing or straining the epidermis and deeper layers of dermal tissue at or near a skin site, thereby reducing tensile or compressive stress at the skin site itself. The stress at the skin site may be reduced to levels below that experienced by normal skin and tissue. The stress or strain may be applied to surrounding tissue in one, two, or three directions to reduce endogenous or exogenous stress at the skin site in one, two or three directions. The physical characteristics of the dressing and/or the method of applying the dressing may also be further configured to resist or reduce the rate of skin stripping or tension blistering from the application of strain to the incision site. For example, the stretching of the adhesive regions when applied to the skin surface may result in an increased tissue density under the adhesive region. This may be the result of generally planar, tangential or parallel compression of skin tissue that is directly attached to that adhesive region, resulting from the relaxation of the adhesive region. In some examples, this tissue compression may reduce the risk of tissue stripping and/or blistering of skin in direct contact with the adhesive, in contrast to bandage "strapping" where one end of a bandage is adhered to the skin and then tensioned or pulled across a wound before the other end is attached to the skin on the opposite side of the wound. Bandage "strapping", while generating tension in the bandage during the application, may simultaneously generate a relatively high tissue strain at the first adhesion site. This high tissue strain then decreases when the bandage is attached to the skin at a second adhesion site as the high peak stresses are redistributed along the skin under the bandage. In contrast, when a pre-strained bandage is applied to the skin, little if any strain may be transferred or generated in the skin as the adhesive regions are applied to the desired locations. When the pre-strained bandage is permitted to relax, however, the strain (or peak strain) in the skin may be increased. Thus, with a pre-strained bandage, temporary high tissue strain may be avoided or otherwise reduced during the application procedure. In other variations, however, the dressing may also be applied to the skin by strapping, or by a combination of pre-straining and strapping.

The dressing may comprise an elastic member, such as a sheet of elastic material. The elastic material of the dressing may comprise a single layer of material or multiple layers of the same or different materials. The material may have any of a variety of configurations, including a solid, foam, lattice, or woven configuration. The elastic material may be a biocompatible polymer, e.g., silicone, polyurethane, TPE (thermoplastic elastomers), synthetic rubber or co-polyester material. The thickness of polymer sheets may be selected to provide the dressings with sufficient load carrying capacity to achieve desired recoverable strains, and to prevent undesired amounts of creep deformation of the dressings over time. In some variations, the thickness across dressings is not uniform, e.g., the thickness across the dressing may be varied to change the stiffness, the load carrying capacity, or recovery strains in selected orientations and/or locations. The elastic material of the exemplary dressing may have a thickness in the range of about 50 microns to 1 mm or more, about 100 microns to about 500 microns, about 120 microns to about 300 microns, or in some variations about 200 microns to about 260 microns. The exemplary dressings have an edge thickness of about 500 microns or less, 400 microns or less, or about 300 microns or less may exhibit less risk of skin separation from inadvertent lifting when inadvertently brushed against clothing or objects. In some variations, the dressings are tapered near the edges to reduce thickness. A tapered edge may also ameliorate peak tensile forces acting on skin tissue adjacent to the adhesive edges of the dressing. This may or may not reduce the risk of skin blistering or other tension-related skin trauma. In other variations, the edges of the dressing may be thicker than the middle of the dressing. It is hypothesized that in some configurations, a thicker dressing edge may provide a relative inward shift of the location of the peak tensile forces acting near the dressing edge, compared to dressings of uniform thickness. The elastic material may have a load per width of at least 0.35 Newtons per mm at an engineering strain of 60% or a load per width of at least 0.25 Newtons per mm at an engineering strain of 45%. The elastic material may have a load per width of no greater than about 2 Newtons per mm at the engineering strain of about 45% to 60%, about 1 Newtons per mm at the engineering strain of about 45% to 60%, about 0.7 Newtons per mm at the engineering strain of about 45% to 60%, or no greater than about 0.5 Newtons per mm at the engineering strain of about 45% to 60%. The system elastic material may have a load per width that does not decrease from an engineering strain of 0% to 60%, a load per width plot that increases linearly from an engineering strain of 0% to 60%, or a load per width plot that is not convex from an engineering strain of 0% to 60%. The elastic material may comprise an adhesive configured to maintain a substantially constant stress in the range of 200 kPa to about 500 kPa for at least 8 hours when strained to an engineering strain of about 20% to 30% and attached to a surface. The elastic material may comprise an adhesive configured to maintain a substantially constant stress in the range of 200 kPa to about 400 kPa for at least 8 hours when strained to an engineering strain of about 20% to 30% and attached to a surface. The substantially constant stress may vary by less than 10% over at least 8 hours, or by less than 5% over at least 8 hours.

Although the depicted dressings may have a generally rectangular configuration with a length and/or width of about 160 mm to about 60 mm, in other variations the dressing may have any of a variety of lengths and widths, and may comprise any of a variety of other shapes. Also, the corners of the dressing may be squared or rounded, for example. The lengths and/or widths of an exemplary dressing may be in the range of about 5 mm to about 1 meter or more, in some variations about 20 mm to about 500 mm, and in other variations about 30 mm to about 50 mm, and in still other variations about 50 mm to about 100 mm. In some variations, the ratio of the maximum dimension of the dressing (e.g. its length) to an orthogonal dimension to the maximum dimension (e.g. width), excluding the minimum dimension of the dressing (e.g. the thickness), may be in the range of about 1:3, about 1:2, about 1:1, about 2:1, about 3:1, about 4:1 about 5:1, about 6:1, about 7:1, about 8:1, about 9:1 or about 10:1 or greater. In some variations, the strain axis of the dressing in use may be oriented with respect to the maximum dimension or to the orthogonal dimension to the maximum dimension. In some variations, the final compressive stress and strain imposed onto the skin by the elastic material may be the result of the dynamic equilibrium between the tensile stress in the skin and the elastic material of the dressing. The skin at the skin site typically comprises an inherent tension that stretches incision site, whether or not any tissue was excised from the skin site. The elastic material and the adhesive region may be configured to be applied to a skin location so that when the dressing is stretched to a particular tension and then adhered to the incision site, tensile stress in the dressing is transferred to the incision site to compress the tissue directly under the dressing along a tangential axis to the skin surface, the stress and strain imposed onto the skin location has a net or resultant orientation or axis is also generally tangential or planar to the elastic material and/or the outer surface of the skin location, with a similar axis to the orientation or axis of the tensile stress in the dressing. The tension in the dressing will relax to a tension level that maintains equilibrium with increased tension in the skin adjacent to the dressing. The application of the dressing to the skin location may involve the placement of the dressing without overlapping or being wrapped onto itself, e.g. wherein only adjacent regions of the dressing are interconnected and wherein non-adjacent regions of the dressing are not interconnected. The actual amount of stress and strain imposed on the skin may vary, depending upon the particular person, skin location, the thickness or various mechanical characteristics of the skin layers (e.g. epidermis, dermis, or underlying connective tissues), and/or the degree of pre-existing scarring, for example. In some further variations, the wound treatment dressing may be selected or configured for use at a specific body location, such as the scalp, forehead, cheek, neck, upper back, lower back, abdominal region, upper torso (including but not limited to the breast folds), shoulder, upper arm, lower arm, palm regions, the dorsum of the hand, finger, thigh, lower leg, the dorsum or plantar surface of the foot, and/or toe. Where applicable, some body regions may be further delineated into anterior, posterior, medial, lateral, proximal and/or distal regions, e.g. the arms and legs.

The dressing may be configured to impose a skin strain in the range of about 10% to about 60% or more, in other configurations about 15% to about 50%, and in still other configurations, about 20% to about 30% or about 40%. To achieve the desired degree of skin strain, the dressing may be configured to undergo elastic tensile strain in the range of about 20% to about 80% or more, sometimes about 30% to about 60%, and other times about 40% to about 50% or about 60%. The dressing may comprise any of a variety of elastic materials, including but not limited to silicones, styrenic block copolymers, natural rubbers, fluoroelastomers, perfluoroelastomers, polyether block amides, thermoplastic elastomers, thermoplastic polyurethane, polyisoprene, polybutadiene, and the like. The material of the exemplary dressing may have a Shore A durometer in the range of about 20 to about 90, about 30 to about 80, about 50 to about 80. The exemplary dressing was constructed of MED 82-5010-05 by NUSIL TECHNOLOGY LLC (Carpinteria, Calif.). Other examples of suitable materials are described in U.S. application Ser. No. 11/888,978, which was previously incorporated by reference in its entirety.

When the dressing is applied to a skin location and allowed to at least partially recover to its base configuration, the recovery level or equilibrium level of strain in the dressing may be in the range of about 4% to about 60% or more, in other configurations about 15% to about 50%, and in still other configurations, about 20% to about 30% or about 40%. The ratio between the initial engineering tensile strain placed onto the dressing before recovery and the resulting engineering compressive strain in the skin may vary depending upon the skin type and location, but in some examples, may be about 2:1. In other examples, the ratio may be in the range of about 4:1 to about 5:4, about 3:1 to about 5:3, or about 5:2 to about 2:1. These skin strain characteristics may be determined with respect to a reference position of the body or body part, e.g. anatomical position, to facilitate reproducible measurements. The particular degree of strain may be characterized as either an engineering strain or a true strain, but may or may not be calculated based upon or converted from the other type of strain (e.g. the strain may be based upon a 45% engineering strain that is converted to a true strain).

In some further variations, one or more characteristics of the elastic material may correspond to various features on the stress/strain curve of the material. For example, the engineering and true stress/strain curves for one specific example of the dressing comprises a material that exhibits an engineering stress of about 1.2 MPa at about 60% engineering strain, but in other examples, the engineering stress may be in the range of about 900 KPa to about 3.5 MPa, about 1 MPa to about 2.2 MPa, about 1 MPa to about 2 MPa, about 1.1 MPa to about 1.8 MPa, about 1.1 MPa to about 1.5 MPa, about 1.2 MPa to about 1.4 MPa. When unloading or relieving stress from the dressing, the material may be configured with an engineering stress of about 380 KPa at about 40% engineering strain, but in other examples, the engineering stress during unloading of the material to about a 40% strain may be in the range of about 300 KPa to about 700 KPa, about 325 KPa to about 600 KPa, about 350 KPa to about 500 KPa, or about 375 KPA to about 425 KPa. When unloading the material to an engineering strain of about 30%, the material exhibits an engineering stress of about 300 KPa, but in other examples, the engineering stress when unloading the material to about 30% strain may be in the range of about 250 KPa to about 500 KPa, about 275 KPa to about 450 KPa, about 300 KPa to about 400 KPa, or about 325 KPA to about 375 KPa. When unloading to an engineering strain of about 20%, the material may have an engineering stress of about 100 KPa, but in other examples, the unloading engineering stress at about 20% may be in the range of about 50 KPa to about 200 KPa, about 75 KPa to about 150 KPa, or about 100 KPa to about 125 KPa. In some examples, the material may be configured to at least achieve a specific range or level of engineering stress at each of the specified engineering strain levels described above, but in other examples, the material may be configured for lower levels of maximum engineering strain, e.g. up to about 30% or about 40%.

In some examples, certain portions of the stress/strain curve may have a particular morphology. For example, for a particular level of maximum strain the loading curve may be generally linear on the corresponding true stress/strain curve. In an example using a dressing described herein, up to a true strain of about 45%, the loading curve had a generally linear configuration. In other examples, the configuration may only be linear along a portion of the loading curve or may be curved along the entire loading curve. Where the loading curve is non-linear, the loading curve may be convex, concave or both. Also, in some examples, the tangent line of the loading curve (i.e. the line between the two triangles) may also be generally co-linear.

In some variations, the elastic material comprises a material having an elastic modulus E of at least about 1 MPa, about 1.5 MPa, about 2 MPa, about 2.5 MPa, about 3 MPa, about 3.5 MPa, about 4 MPa, about 5 MPa, about 6 MPa, about 7 MPa, about 8 MPa, about 9 MPa or at least about 10 MPa or greater. The material elastic modulus E may be no greater than about 10 MPa, about 9 MPa, about 8 MPA, about 7 MPa, about 6 MPa, or about 5 MPa, or about 4 MPa.

In addition to the absolute stress levels at certain strain levels described above, the material may also be characterized with respect to the ratio between a) the stress to achieve a particular strain during loading, and b) the stress at the same strain during unloading. For example, the material may have a ratio of at least 4:1 to about 3:2 at each of the 20%, 30% and 40% strain levels, but in other examples, the material may exhibit these ratios only at 20%, at 30%, or at 40% strain levels, or at both 20% and 30% but not 40%, or at both 30% and 40% but not 20%. In other examples, the ratio at one, some or all of the strain levels may be in the range of about 3:1 to about 2:1, or about 5:2 to about 2:1.

In some examples, the elastic material of the dressing may be configured under testing conditions to achieve a stable level of stress at a constant strain, e.g. the material exhibits a limited amount of stress relaxation over a particular period of time and at a particular level of strain. The period of time may be at least about 8 hours, about 12 hours, about 18 hours, about 24 hours, about 36 hours, about 48 hours, about 72 hours, about 4 days, about 5 days, about 6 days, or about a week or more. The level of strain may be about 10%, about 20%, about 30%, about 40%, about 50%, about 60%, about 70%, or about 80% or more. The stress of the exemplary dressing over various time curves may be configured to maintain an engineering stress of about 300 KPa at an engineering strain of about 30% without noticeable deviation over a period of about 1 hour, about 2 hours, about 3 hours, about 4 hours, about 5 hours, about 6 hours, about 7 hours, or about 8 hours or more. The stresses at 10% strain, 20% strain, and at 40% may be lower or higher.

In some variations, the elastic material or the dressing may be configured under testing conditions to maintain a particular minimum level of stress when held at a constant strain over a particular time period. In an example to assess the ability of a backing material to maintain a stress and strain on skin over time, engineering strains were measured while each backing material was tensile strained to 60% at a rate of 100 microns per second and held for 10 minutes, and then dropped to a strain of 30% at a rate of 100 microns per second and held for 9 hours. For example, the exemplary dressing is able to maintain an engineering stress level of about 350 KPa at an engineering strain of 30%. In some other examples, the minimum level of stress may be about 100 KPa, about 120 KPa, about 140 KPa, about 160 KPa, about 180 KPa, about 200 KPa, about 220 KPa, about 240 KPa, about 260 KPa, about 280 KPa, about 300 KPa, about 320 KPa, about 340 KPa, about 360 KPa, about 380 KPa, about 400 KPa, about 420 KPa, about 440 KPa, about 460 KPa, about 480 KPa, about 500 KPa, about 600 KPa, about 700 KPa, about 800 KPa, about 900 KPa or about 1000 KPa or greater. The level of constant strain may be different in other configuration, with a level of about 15%, about 20%, about 25%, about 30%, about 35%, about 40%, about 45%, about 50%, about 55%, about 60%, about 65%, about 70%, about 75%, or about 80%. The time period over which the dressing is able to maintain a stress level may be at least about 2000 seconds, about 3000 seconds, about 4000 seconds, about 5000 seconds, about 6000 seconds, about 7000 seconds, about 8000 seconds, about 9000 seconds, about 10000 seconds, about 20000 seconds, about 30000 seconds, about 40000 seconds, about 50000 seconds, about 60000 seconds, about 70000 seconds, about 24 hours, about 36 hours, about 48 hours, about 72 hours, about 4 days, about 5 days, about 6 days, about 7 days, about 10 days, about 2 weeks, about 1 month or more. In some variations, the dressing, the elastic material and/or the adhesive material is configured to exhibit less than about a 15% change in stress or strain level over the particular period when applied to a skin surface or test surface. In other examples, the degree of change may be about 12%, about 10%, about 8%, about 6%, about 5%, about 4%, about 3%, or about 2% or less. The stress or strain may be an engineering stress or strain, and/or a true stress or strain.

The adhesive used may be, for example, a pressure activated adhesive (PSA), as a silicone, acrylic, styrene block copolymer, vinyl ether, nitrile or other PSA. In other variations, a non-pressure sensitive adhesive may be used, including but not limited a heat or light-cured adhesive. The pressure sensitive adhesive may be made from, e.g., polyacrylate-based, polyisobutylene-based, silicone-based pressure sensitive adhesives, synthetic rubber, acrylic, and polyisobutylene (PIB), hydrocolloid, and the like. The T-peel release force and blunt probe tack force of the adhesive may be measured by a standardized test method, such as ASTM D1876 and ASTMD2979 or other appropriate method. In some variations, the T-peel release force or blunt probe tack test value of the adhesive is configured to maintain loads of at least about 50 mPa/mm for at least about 24 hours, about 48 hours, about 72 hours, about 1 week, about 2 weeks, about 3 weeks, about 4 weeks or more. In other variations, the loads may be at least about 75 mPa/mm, about 100 mPa/mm, about 125 mPa/mm, or at least about 150 mPa/mm over the particular time period. The degree of adhesion (e.g. as measured by the T-peel release force or blunt probe tack test value) may vary depending upon the degree of strain placed onto the skin or incision site, and in some variations, these time periods may be based upon an average skin strain of about 10%, about 20%, about 30%, about 40%, or about 50% or more. In some variations, the adhesive may have a T-peel release force of at least about 150 kg/m, about 160 kg/m, about 170 kg/m, about 180 kg/m, about 190 kg/m, about 200 kg/m, about 210 kg/m, about 220 kg/m, about 230 kg/m, about 240 kg/m, about 250 kg/m, about 260 kg/m, about 270 kg/m, about 280 kg/m, about 290 kg/m, about 300 kg/m, about 310 kg/m, about 320 kg/m, about 330 kg/m, about 340 kg/m, about 350 kg/m, about 400 kg/m, about 450 kg/m, or at least about 500 kg/m or higher. In some further variations, the T-peel release force may be no greater than about 1000 kg/m, about 900 kg/m, about 800 kg/m, about 700 kg/m, about 600 kg/m, about 500 kg/m, about 400 kg/m or about 300 kg/m. The blunt probe tack test value of the adhesive may be at least about 0.50 kg, about 0.55 kg, about 0.60 kg, about 0.65 kg, about 0.70 kg or about 0.75 kg or higher, and may be no greater than about 1 kg, about 0.9 kg, about 0.8 kg, about 0.7 kg, or about 0.6 kg. The T-peel release force and blunt probe tack force may be measured by a standardized test method, such as ASTM D1876 and ASTMD2979 or other appropriate method. Other features or variations of the device are described in U.S. application Ser. No. 11/888,978, filed on Aug. 3, 2007, incorporated in its entirety herein by reference.

The release liners may comprise any of a variety of materials, including both opaque and transparent materials. The release liners may comprise Mylar or paper, or any other material with reduced adhesion to the adhesive material(s) of the device. For example, for a silicone adhesive, a fluoropolymer-treated polyester film may be used, and for an acrylic pressure sensitive adhesive, a silicone treated polyester or Mylar film or silicone treated craft paper may be used. In variations where the device has multiple separate adhesive regions, separate release liners may be provided for each region, or some regions may be covered by the same release liner.

Examples of dressings, applicators or tensioning devices that may be used in the devices kits or methods herein may include those provided in U.S. application Ser. No. 12/854,859 filed Aug. 11, 2010, the disclosure of which is already incorporated in its entirety herein by reference without limitation.

The packaging assembly, applicator and/or tensioning device may comprise a tensioning structure, and a first attachment portion configured to releasably attach to a dressing and a second attachment portion configured to releasably attach to the dressing, wherein the tensioning structure may be configured to exert a separation force between the first attachment portion and the second attachment portion to cause a strain in a dressing attached to the first and second attachment portions. An elastic dressing may be configured to releasably attach to the first and second attachment portions of a dressing and packaging assembly and may include an attachment structure or may be integral with attachment structures of a packaging device, applicator or tensioning member. The tensioning structure may also act as an applicator device or may be configured to permit a user to apply a dressing to skin of a subject.

Attachment structures of a packaging device, dressing assembly, dressing carrier, support, base, applicator, tensioning or straining device may include any structures that are used to attach or couple an applicator, tension or straining device to a dressing. A dressing may or may not have attachment features or structures. Any such attachment features may be integral with or include any of the attachment structures or corresponding structures to the attachment structures of the packaging, applicator dressing and/or tensioning device.

In some variations the assembly may comprise one or more mechanisms or elements configured to facilitate separation, release, removal or detachment of the dressing from the packaging, applicator or tensioning device, other attachment elements or other portions of the dressing assembly, including but not limited to the separation devices and methods described herein. Release elements or releasable attachment structures may include but are not limited to pockets and tabs, hook and loop mechanism, hooks, angled bars, pivoting, rolling, rocking or sliding features associated with or coupled to attachment structures, adhesives, removable adhesives, adhesive tapes or other adhesive devices, pegs, rip cords, towel bar configurations, sliding pins, friction locks, cam locks, vacuum or suction devices, snap connectors, carpet tack, press fit connections or other connections, levers, latches, locking members, spring members, for example, or other mechanisms such as cutters or rip cords or other structures or features to facilitate tearing, cutting or separation of attachment structures or elements perforated or otherwise severable structures, that permit removal of dressing from the applicator, packaging, other portions of the dressing assembly and/or attachment structures, features, elements or portions They may be self-releasing latches or spring members. They may be actuated when a pressure member is applied to a skin treatment device prior to removing the applicator. They may be manually actuated.

As noted, a packaging or applicator, tensioning device and/or straining device may be provided in some embodiments to impart a strain to a skin treatment device with an external force and/or to maintain a strain imparted to the skin treatment device. The packaging, applicator or tensioning device may be configured to pivot or rotate to tension the dressing. In some examples, the straining device may be configured to impart and/or maintain a single predetermined or pre-set strain or a plurality of predetermined or pre-set strains, or predetermined maximum or minimum amounts of strain. Features described herein with respect to a packaging assembly, applicator or tensioning device may also be used in any device that is used to strain a dressing. A packaging or applicator, tensioning or straining device that is described as being in an unstrained configuration is in a configuration in which a dressing may be unstrained or relatively less strained when attached to the packaging, applicator, tensioning or straining device. A packaging, applicator, tensioning, or straining device that is described herein as being in a strained configuration, is in a configuration in which a dressing may be strained or relatively more strained when attached to the packaging, applicator, tensioning or straining device, or with respect to an unstrained configuration, when applied to a subject's skin.

Packaging devices, applicators, tensioning devices, and corresponding attachment features may be configured to provide multi-direction strain or additional strain in an orthogonal direction to a dressing.

The packaging device, applicator, tensioning device and/or attachment structure profile may be straight, curved or otherwise varied. For example, the shape of the elements of a device may be configured to follow the shape of the area of the subject's body to which the skin treatment device is to be attached. A packaging device, tensioning device, applicator or elements thereof may be selected or configured to have a profile that has a desirable profile for a particular body location or profile where the skin treatment device is to be placed on a subject's skin. A packaging device, applicator, tensioning device or elements thereof may be selected or configured to closely match a portion of a subject's body profile. The packaging device, applicator or tensioning device and/or an element or segment thereof, may be curved, curvable, flexible, bendable, malleable, deformable, shapeable or movable to provide alternative shapes or profiles of an attached dressing. They may be relatively curved, curvable, flexible, malleable, bendable, deformable, shapeable or movable in at least one direction while being more rigid in another direction.

A variety of locking, latching, securing, attaching or detent mechanisms may be used to maintain the packaging, applicator or tensioning device in a various configurations including but not limited to unstrained, partially strained, strained configurations. A variety of locking, latching or detent mechanisms may be used to maintain a dressing in a variety of configurations including unstrained, partially strained, strained. By locking the packaging, applicator, tensioning device, or dressing in a strained position, a predetermined strain of a given dressing may be achieved. The predetermined amount of strain may be a predetermined absolute percentage of strain or level of force that is independent of the shape and/or size of the treatment site. As a further example, this absolute percentage of strain or level of force may be independent of the minimum strain or force to achieve sutureless wound closure (e.g. a relative strain or force to achieve opposition of the incision edges of a treatment site). Furthermore, the force needed to achieve wound closure is not a predetermined strain or force, since the final level of strain or force is not known until opposition of the incision edges is achieved.

Referring to FIGS. 1 to 5C, a variation of a dressing and packaging assembly 100 is illustrated. The packaging assembly 100 comprises a book-like applicator and/or tensioning device 120, a dressing assembly 110 including a dressing 130, and a release 150 configured to release the dressing 130 from the applicator and/or tensioning device 120.

The dressing 130 comprises an elastic sheet 131 with one or more adhesive regions comprising a layer of skin adhesive 135 on a first surface 135a. The adhesive used may be, for example, a suitable pressure activated adhesive (PSA), or a non-pressure sensitive adhesive.

The packaging assembly 100, applicator or tensioning device 120 and/or dressing assembly 110 may be configured to pre-strain the dressing 130 and/or permit transfer of the pre-strained dressing 130 to the skin of a subject. The applicator and/or tensioning device 120 may also provide for a convenient, expeditious or sterile transfer of an adhesive portion of the dressing 130 to a skin and/or wound site of a subject.

The device 120 comprises a cover 121 and a base 122. The dressing assembly 110 is removably coupled or anchored to the device 120 which may act as a dressing carrier or a support. The cover 121 may be generally planar and include sides 123, 124 with corresponding edges 123a, 124a along its length, and edges 121a at opposing ends. The dressing carrier or base 122 may be generally planar and include sides 125, 126 with corresponding edges 125a, 126a along its length and edges 122a at opposing ends.

According to some variations, the cover and/or base 121,122 or elements or segments thereof may be constructed to be sufficiently firm or rigid or less flexible relative to an attached dressing to support an attached dressing until it is applied to a subject as described with respect to the variations herein. Such material may comprise, for example, a plastic, e.g., polypropylene, polycarbonate, polytetrafluoroethylene (PTFE® or TEFLON®), LDPE, high-density polyethylene (HDPE), ultra high-molecular weight polyethylene (UHMWPE), polyvinyl chloride (PVC) or acrylic, nylon or a paperboard. The elements or segments may be a laminate of a material, such as a solid bleach sulfate paperboard with a layer of flexible material between layers of paperboard, for example, silicone, polyurethane, LDPE or a rubber material. The material may also be a metal as for example, ductile aluminum or stainless steel. The metal may comprise a foil, ribbon, wire or other form.

Cover 121 and base 122 are movably, hingedly or pivotably coupled at sides 123, 125. For example, a layer of material such as silicone, polyurethane, low-density polyethylene or a rubber material may be glued to each of the cover and base, flexibly attaching them together at sides 123, 125. Alternative devices and methods may be used to couple the cover 121 and base 122. For example, various composite structures or laminates may be used. Also devices may be constructed out of a single substrate that provides flexibility in some selected regions and rigidity in others, or a relative or absolute flexibility in a first direction with a relative or absolute rigidity in a second direction that may be transverse to the first direction. Although the cover 121 and base 122 depicted in FIGS. 1 to 5C have generally the same size and shape, in other examples, the cover 121 and base 122 may be different sizes and/or shapes. Cover 121 and/or base 122 may be bendable, foldable, curvable, flexible, malleable or shapeable permitting relatively more even placement on a location with a varying shape or curvature. For example, cover and base 121, 122 as illustrated are each divided into segments 127 along lengths that are bendable or movable with respect to adjacent segments, permitting flexibility of the device 120 along its length. The segments 127 may be constructed of a more rigid material that reduces flexion in a widthwise or other direction. Other configurations that vary the directions of rigidity and/or flexibility may be use. Configurations may include providing rigidity in a direction in which a dressing is strained that is sufficient to create and/or maintain a desired level of strain. The segments 127 may be coupled by a material, such as an elastomer, e.g., silicone that flexibly holds the segments together in relationship to each other. Other construction may also be used to flexibly couple segments or other elements. The material coupling or binding the cover and base 121, 122, may or may not be continuous with the material that couples the segments 127 to adjacent segments 127, and may or may not be attached to all or a portion of a side of cover and base 121, 122. The various attached structures, e.g. the segments and/or the cover and base and coupling elements may provide a structural support for the dressing carrier to be manipulated by a user. Margins between at least a portion of the structural support elements, dressing carrier or backing, and the dressing may be provided at or near edges 121a, 123a, 124a, 122a, 125a, and/or 126a, for example as described further herein. In some further embodiments, the material attaching the cover 121 and base 122 may comprise a semi-rigid structure that may be biased to an open or a closed configuration, or a configuration therebetween. In still other variations, the cover 121 and base 122 may be attached by any of a variety of articulations, including but not limited to one or more a pin-based hinge joints, rings attached to holes in the cover 121 and base 122, or ball-and-socket joints.

Figure 5A:
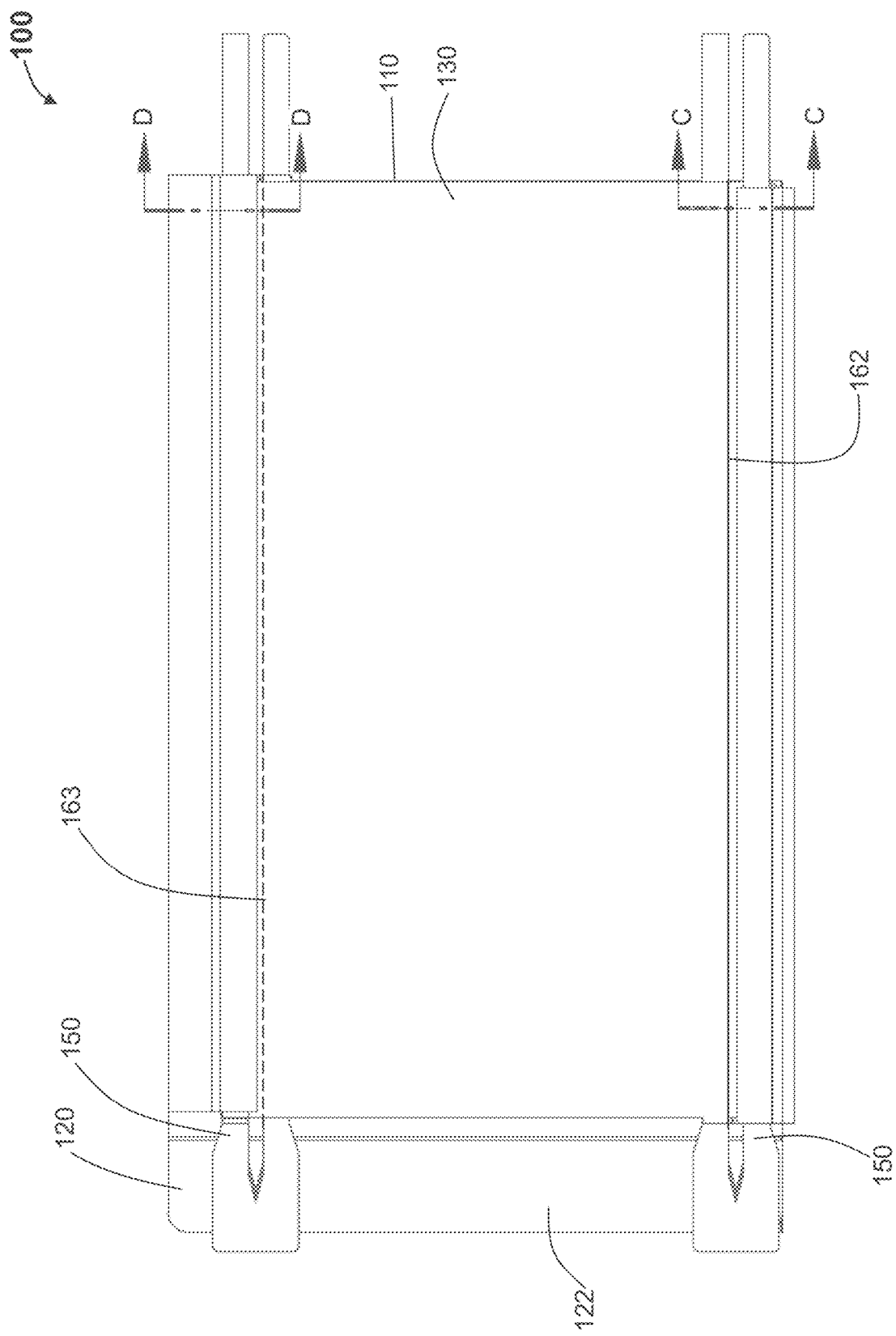
FIG. 5A is a schematic bottom view of the dressing and packaging assembly in the position illustrated in FIG. 3.

As exemplified in FIGS. 5A-5C, a variation of construction of a package is shown. Cover 121 and base 122 comprise relatively firm or rigid elements, for example battens 121a, 121b and battens 122a, 122b respectively that are attached by way of a sheet 128 of material, such as, e.g., silicone, polyurethane, low-density polyethylene or a rubber material that also flexibly couples cover and base 121, 122 at sides 123, 125. Segments 127 may have alternative shapes and construction coupling the segments 127 together. Thus, the device 120 may be constructed to bend or curve to varied extents or in multiple directions. Accordingly, a device may be constructed to be used on a specific anatomical location or with varying sizes, or may be constructed to have a shape for a particular situation or individual.

According to some variations each of the cover 121 and base 122 is constructed at least in part of a clear plastic, semi-opaque or other material that provides a window portion 159 through which a wound, incision, or other location may be visualized for accurate placement of the dressing 130. The cover 121 and base 122 may or may not comprise the same material. The elastic sheet 131 and adhesive layer 135 may also be sufficiently clear to permit visualization through them. A more opaque material may be provided on portions of the material to create boundaries of a window 159. The segments 127 may be clear or semi-opaque to provide the window for viewing, positioning, and/or centering the location of a wound or position on skin with respect to the dressing 130 or for positioning the wound within an optimal or most effective strain zone of the dressing. The boundaries or other markings may assist a user in placing the dressing 130 in an appropriate position over the wound or incision.

The dressing 130 of the dressing assembly 110 has a first side or edge 133 having a length, and a second side or edge 134 having a length. The dressing 130 is coupled to the packaging assembly 100 along the lengths of the dressing's sides 133, 134. When the device 120 is closed, the adhesive layer 135 faces away from the base 122 and is covered by a release liner 149 that is attached to the inside surface 177 of the cover 121. The dressing assembly 110 also includes an attachment sheet 141 having a first side 143 and a second side 144. The attachment sheet 141 couples the dressing 130 to the cover of the device 120 which when opened, exerts a straining force on the dressing 130 through the attachment sheet 141. According to some variations, the attachment sheet 141 is flexible while being relatively inelastic with respect to the dressing 130 and may be constructed, e.g., out of a low density polyethylene. When assembled, the attachment sheet 141 is bonded to the elastic sheet 131 of the dressing at (for example, using a combination of a silicone PSA/acrylic PSA) or near the sides 134 and 143 of the dressing 130 and attachment sheet 141 respectively. The attachment sheet 141 is coupled at its side 144 to the cover 121 at attachment points 137 defining a line or area of attachment 137a along the length of the cover 121. The dressing 130 is coupled to the second side 124 of the base 122 at a location near the first side 133 of the dressing 130. As such, the elastic sheet 131 is attached at attachment points 138 defining a line or area of attachment 138a along a length of the base 122. A number of bonding methods or adhesives may be used to attach the attachment sheet 141 to the cover 121, for example, a low surface energy PSA such as an acrylic adhesive.

Figure 2:
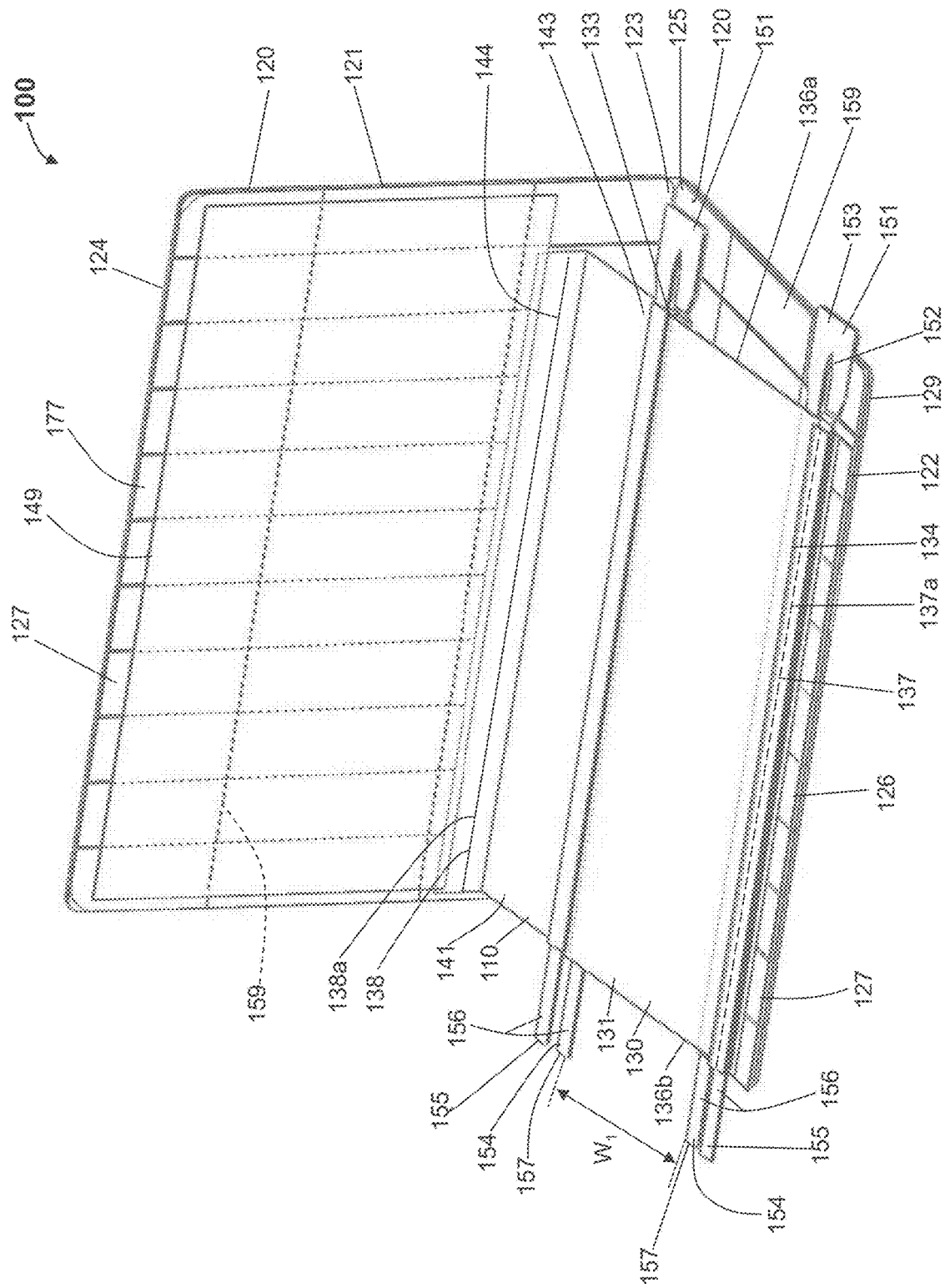
FIG. 2 is a perspective view of the dressing and packaging assembly of FIG. 1 with a cover open at about a ninety degree position from the closed position.

When the assembly 100 is in a closed configuration as illustrated in FIG. 1 and at an open 90 degree configuration as shown in FIG. 2, the elastic sheet 131 is relaxed or unstrained, with the elastic sheet 131 having an unstrained width w1. As the assembly 100 is opened to 180 degrees or up to about 360 degrees (e.g. by rotating or pivoting the cover 121 with respect to the base 122), the orthogonal distance increases between lines or areas of attachment 137a, 138a. According to some variations the assembly is opened to no less than about 180 degrees (minimum angular change) to provide for application of a dressing without interference of the assembly 100. When the device 120 is opened, it exerts a separation force between attachment regions defined by attachment lines or areas 137a, 138a or corresponding attachment areas. The force tensions the elastic sheet, creating a strain. Tensioning and imparting a strain on the dressing 130 increases the width between attachment lines or areas 137a, 138a to w2. The increase in the width, i.e., w2 minus w1, may be a percentage of w1 or a percent strain as described herein. While straining is illustrated as starting when the cover 121 is opened about 90 degrees from the base 122, the dressing 130 may be attached to the cover 121 at a number of locations or in a number of configurations that may vary the cover position or configuration at which straining begins. The edge 124a or side 124 of the cover 121 may act as a lever arm to provide a mechanical advantage, which may depend, among other things, on the distance of the point of attachment 138 of the dressing assembly 110 on the cover to the edge 124a of the cover 121 as well as the angle of the cover 121 with respect to the base 122 at which the tensioning of the dressing occurs. Additionally, the point of attachment 138 of the inelastic attachment sheet 141 to the cover 121 may determine amount of strain applied to the dressing, assuming among other things, the length of the attachment sheet 141 remains the same and the point of attachment 137 of the dressing assembly 110 to the base 122 remains the same According to one variation, the dressing 130 may be substantially fixed at one edge, (e.g. at edge 134 at the side 126 of the base 122) while not being fixed at an opposite edge (e.g., edge 133 moves when strained with respect to edge 125a of base 122). When the cover 121 is opened and the dressing 130 is strained, the width of the strained dressing may be less than the width of the base 122 and/or the cover 121 so that the area of the dressing is located over the area of the base 122 and or the cover 121, i.e. the base 122 and/or cover 121 margins outside of the area of the dressing. According to other variations the dressing may be fixed at both edges.

According to some variations, the dressing is sufficiently large with respect to the device 120 so that when applied to the skin, there is relatively less interference by the device 120. According to one example, the width of the strained portion of the dressing may be about 10 mm, about 20 mm, about 30 mm, about 40 mm, or about 50 mm Other strained dimensions may be used. According other variations, the distance between each of edges 133, 134 of the dressing 130 and the edges 125a, 126a of the base 122 respectively (and/or the edges 123a, 124a of the cover 121) is no greater than about 10 mm, 15 mm or 20 mm. According to some variations, the distance between the edges 136a, 136b of the dressing and the edges 122a of the base is no greater than about 10 mm, about 15 mm or about 20 mm.

Figure 3:
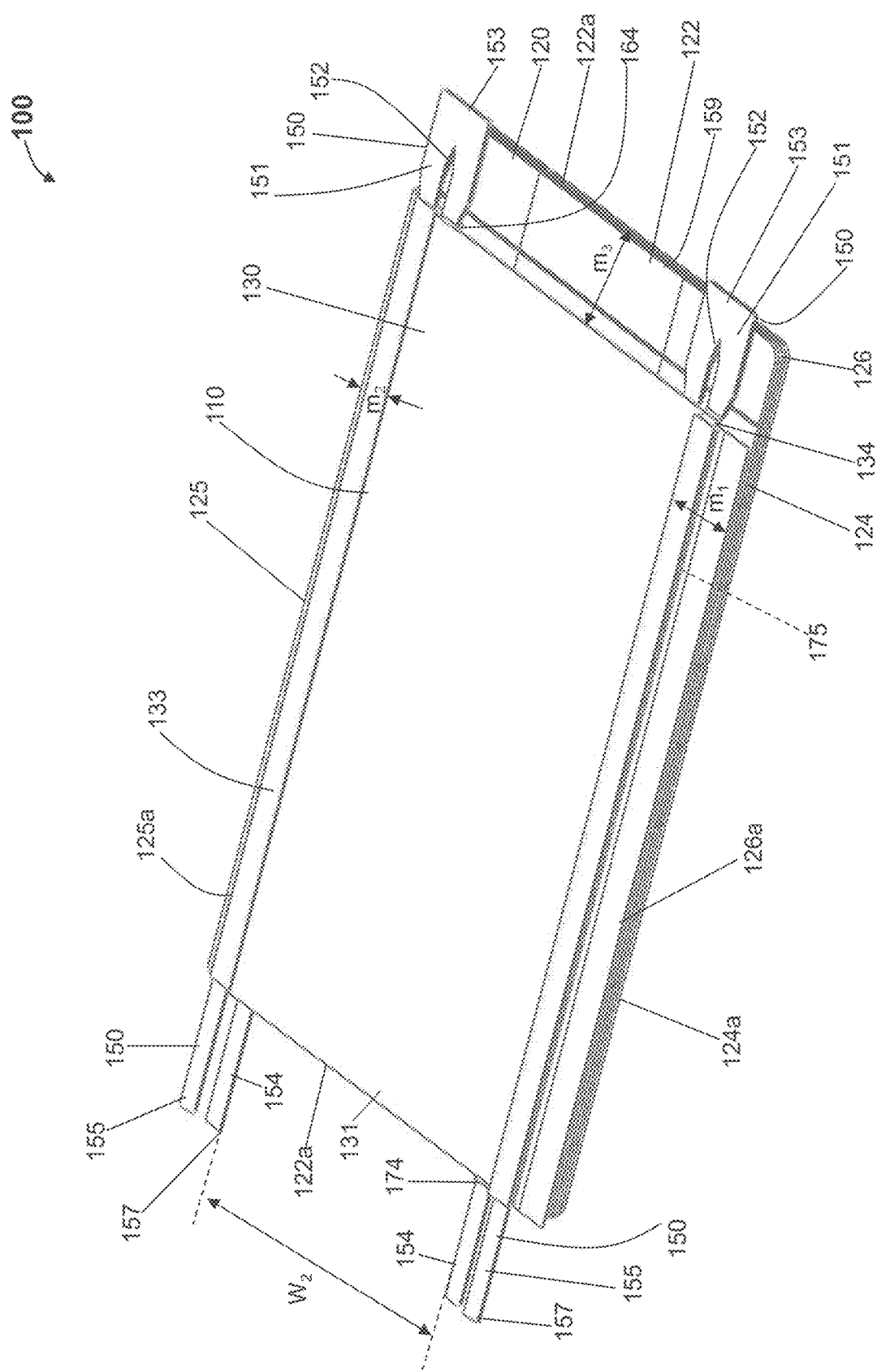
FIG. 3 is a bottom perspective view of the dressing and packaging assembly of FIG. 1 with a cover open at about a 360 degree configuration from the closed position.
Figure 4:
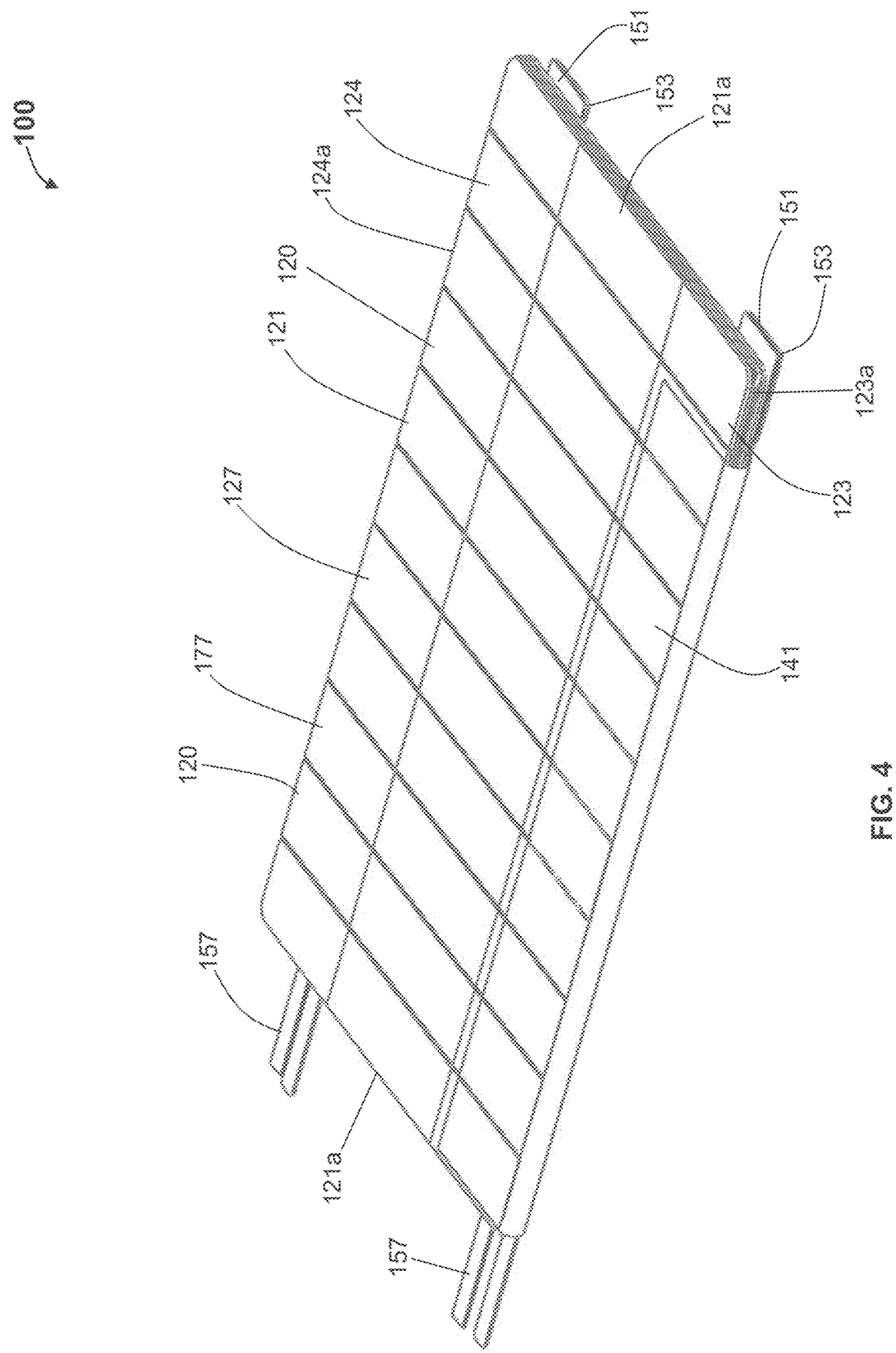
FIG. 4 is a top perspective view of the dressing and packaging assembly of FIG. 1 with a cover open at about a 360 degree configuration from the closed position.

According to some variations, edges 133, 134, 136a, 136b of the dressing 130 are at least about 1.0 mm inward of at least a portion of the edges 125a, 126a, and/or 122a of the base 122 so that the edges 125a, 126a, and/or 122a of the base 122 may be gripped by a user with a reduced likelihood of touching the dressing 130 or the adhesive layer 135. According to some variations, the ends 136a, 136b of the dressing 130 have a margin of at least about 1.0 mm inward of the ends 122a of the base 122. According to some variations the sides 133, 134 and ends 136a, 136b of the dressing 130 have a margin of about 10 mm from the sides 125, 126 and ends 122a of the base respectively. According to some variations the sides 133, 134 and ends 136a, 136b of the dressing 130 have a margin of about 15 mm from the sides 125, 126 and ends 122a of the base respectively. Each of the margins between sides 133,134 or ends 136a, 136b of the dressing 130 and sides 125, 125, and ends 122a of the base 122 may be different. As illustrated in FIG. 3, for example, margins m1 and m2 are about no less than 3 mm and margin m3 is about 15 mm Similar margins may be provided between the dressing 130 and the edges 121a, 123a, and/or 124a of the cover 121, for example if the edges of the cover 121 are used alternatively or additionally to grasp the device 120 or manipulate the dressing 130. Then, once the cover 121 is opened and the adhesive layer 135 is exposed, the adhesive side of the dressing 130 may be placed on a skin or wound site using the device 120. As shown in FIGS. 3 and 4 the cover 121 and base 122 may be rotated an additional amount, with respect to each other, e.g., up to approximately 360 degrees from the closed configuration prior to applying the dressing 130. A locking mechanism may optionally be provided to lock or secure the device in an open, partially opened or closed position. In some examples, the locking mechanism may comprise magnets, hook-and-look attachment structures, snaps, latches, clips and the like.

Figure 6:
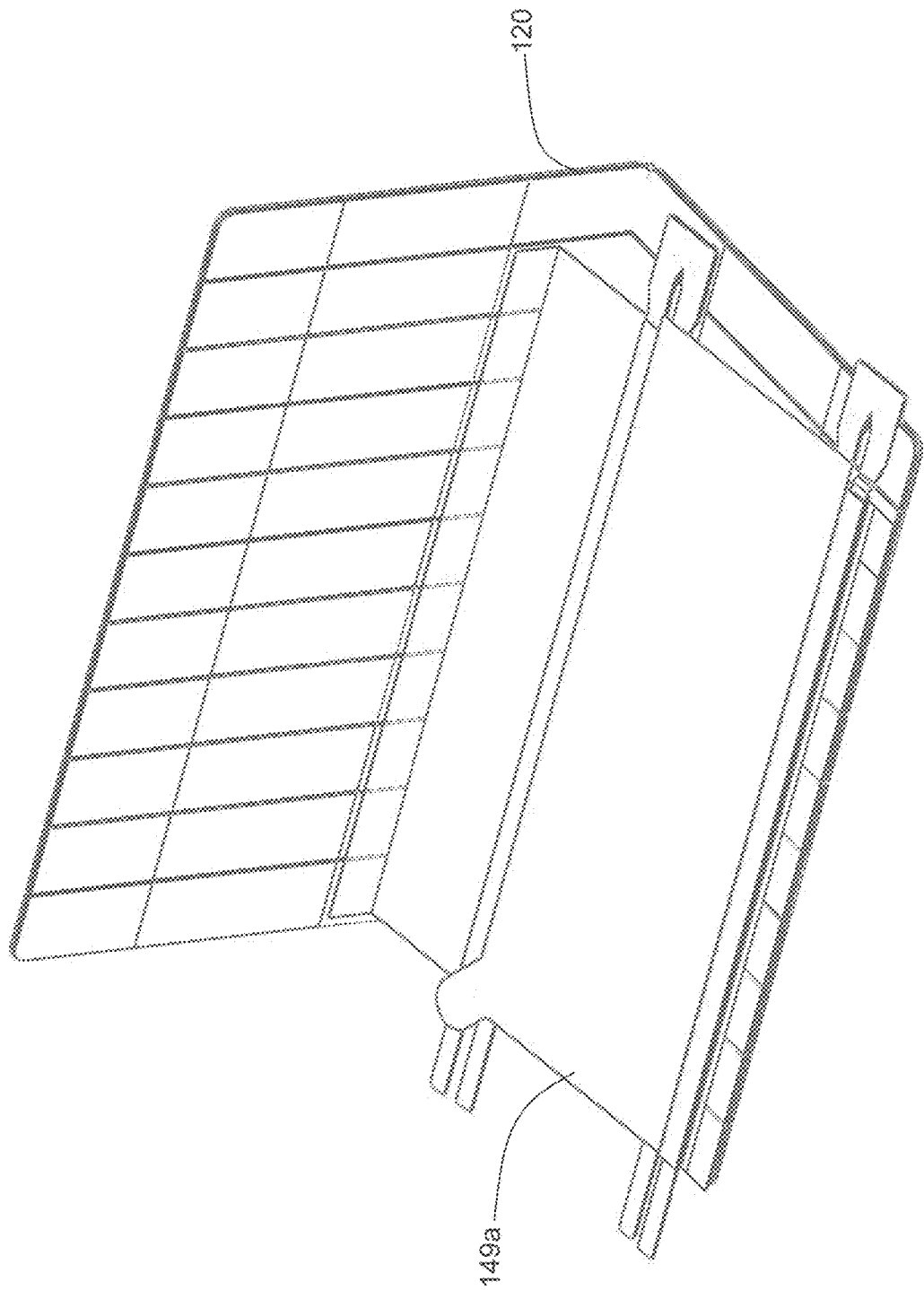
FIG. 6 illustrates a variation of a dressing and packaging assembly.

The adhesive layer 135 of the elastic sheet 131 is protected by a release liner 149 before the applicator or tensioning device 120 is opened. The release liner 149 is attached or glued to the inside surface 177 of the cover 121 so that when the cover 121 is opened as shown in FIG. 2, and is separated from the base 122 (prior to straining the elastic sheet 131), the release liner 149 is pulled away from the elastic sheet 131 exposing the adhesive layer 135. Alternatively, as shown in FIG. 6, a release liner 149a may be provided on the adhesive layer 135 that is not attached to the cover 121. When the device 120 is opened, and prior to straining the dressing 130, the release liner 149a may be manually removed from the elastic sheet 131 to expose the adhesive layer 135.

After the dressing 130 is strained, and the liner 149 or 149a is released, the dressing 130 may be applied to a desired location on a subject's skin. The window 159 may be used to visualize proper placement. The user may apply pressure to the back side 129 of the device 120 to activate the adhesive on the elastic sheet 131 and/or to apply compression to a wound. Alternatively, if the cover 121 is rotated to 360 degrees, pressure may be applied to the inside 177 of the cover 121. Once applied to a subject, the elastic sheet 131 may be released from the packaging, applicator or tensioning device 120 using a release structure or mechanism 150.

The release mechanism 150 may comprise cutters 151 each positioned on opposite sides 133, 134 of the elastic sheet 131. Each cutter 151 comprises a blade 152 on one end 153 with legs 154, 155 extending to opposing pull tab or tabs 156 on an opposite end 157. The blade 152 comprises a sharp surface that may be generally v-shaped or otherwise shaped. The blade may be constructed, e.g., of stainless steel, ceramic or hard plastic. The blade 152 and the pull tabs 156 each extend proud of the ends 136a, 136b of elastic sheet 131, respectively and ends 122a of the base 122. Cutters 151 are attached to the dressing assembly 110 in a manner that defines general cutting paths 162, 163 (depicted best in FIG. 5A) along which the blades 152 are pulled by tabs 156 to cut the dressing assembly 110 to release the dressing 130. In some variations, the dressing may be scored, perforated or otherwise configured to facilitate separation by the release mechanism.

As best shown in FIGS. 5B and 5C, tubes 164, 165 for receiving and guiding legs 154, 155 respectively of a cutter 151, are positioned along the side 133 of the elastic sheet 131. The tubes 164, 165 may be positioned so that the cutting path 162 is between the tube 164 and the tube 165. The tube 165 is coupled, e.g., glued to the adhesive surface 135 of the elastic sheet 131 at a location closer to the side 133 than the cutting path 162. The tube 164 is coupled to the back surface 139 of the elastic sheet 131 by way of the attachment sheet 141, which is also coupled to the elastic sheet 131 at a location closer to the side 133 than the cutting path 162. The tube 164 is coupled to a free end 145 of the attachment sheet 141 that extends inward of the cutting path 162 with respect to the side 133. Thus, the tube 164 may be positioned inside of the cutting path 162 without being attached to the elastic sheet 131 inside of the cutting path 162. This allows the dressing 130 to be released from the remainder of the packaging assembly 100 including the cutter 151 with tube 164 and attachment sheet 141. A protective member 170 is attached, e.g. glued to the top of tube 165. The protective member 170 includes a ledge 171 that extends over the cutting path 162 so that when the adhesive layer 135 is positioned on the skin of a subject and the cutter 151 is actuated, the skin is protected from the blade 152.

Tubes 174, 175 for receiving and guiding legs 154, 155 respectively are positioned along the side 134 of the elastic sheet 131. The tubes 174, 175 are positioned so that the cutting path 163 is between the tube 174 and the tube 175. The tube 175 is coupled, e.g., glued to the adhesive surface 135 of the elastic sheet 131 at a location closer to the side 134 of elastic sheet 131 than the cutting path 163. The tube 174 is coupled to the back surface 139 of the elastic sheet 131 by way of the extender sheet 146. The tube 174 is coupled to a free end 147 of the extender sheet 146 that extends inward of the cutting path 163 with respect to the side. Tube 174 is also coupled to the elastic sheet 131 at a location closer to the side 134 than the cutting path 163. Thus the tube 174 may be positioned inside of the cutting path 163 without being attached to the elastic sheet 131 inside of the cutting path 163. This allows the dressing 130 to be released from the remainder of the packaging assembly 100 including the cutter 151 with tube 175 and extender sheet 146. A protective member 170 is attached, e.g., glued to the top of tube 175. The protective member 170 includes a ledge 171 that extends over the cutting path 163 so that when the adhesive layer 135 is positioned on the skin of a subject and the cutter 151 is actuated, the skin is protected from the blade 152.

The inside of the tubes 164, 165, 174, 175 may be coated with a lubricious material, e.g. with Kapton tape. The guiding legs 154, 155 may be constructed of a low friction material such as, e.g., HDPE or UHMWPE, so the legs 154, 155 may readily slide in the tubes 164, 165, 174, 175 to permit smooth cutting of the dressing 130 from the remainder of the packaging assembly 100.

When the dressing 130 is strained and the adhesive 135 is exposed, the dressing 130 may be applied with the adhesive side 135 towards the skin of a subject. The side 133 of the elastic sheet may then be released from the applicator by pulling the tabs 146 to draw the blade 152 across cutting path 162. Also, the side 134 of the elastic sheet may then be released from the applicator by pulling the tabs 146 to draw the blade 152 across cutting path 163. Thus the elastic sheet 131 is released from the packaging 100 (including the release 150).

Figure 7:
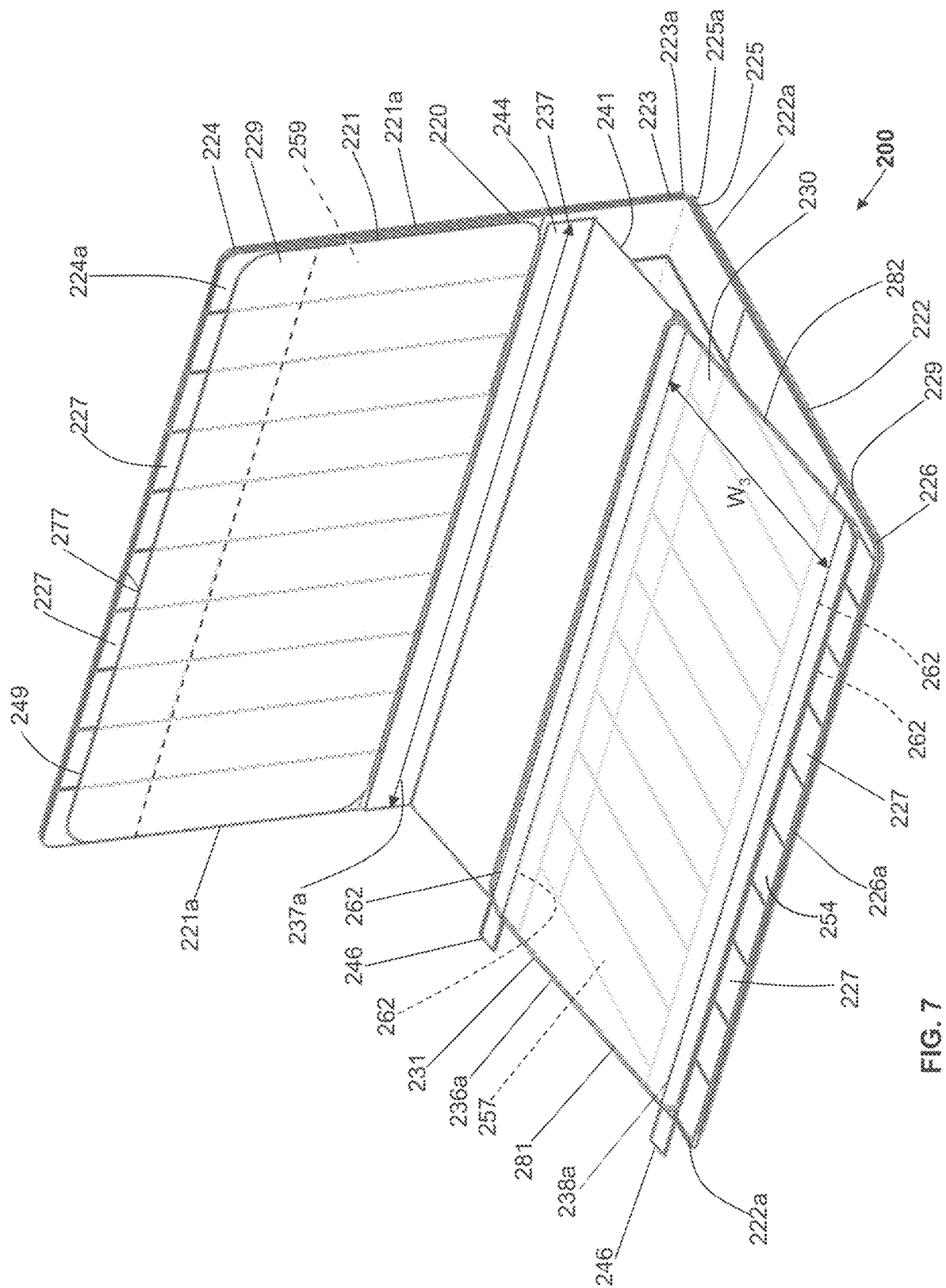
FIG. 7 is a perspective view of a dressing and packaging assembly with a cover in an open position 90 degrees from a closed position.
Figure 8C:
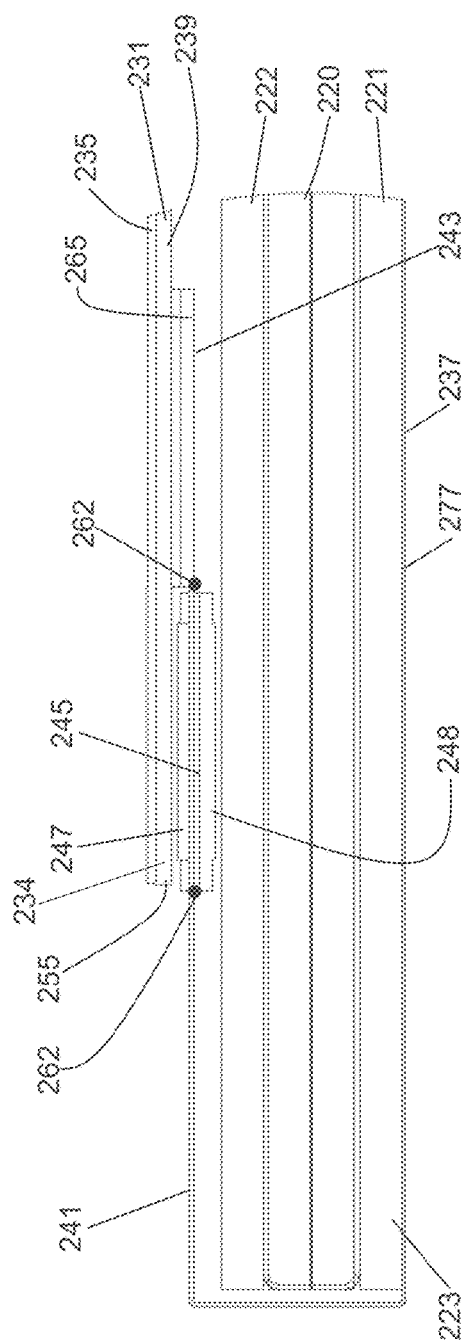
FIG. 8C is an expanded view of section 8C of FIG. 8A.
Figure 9:
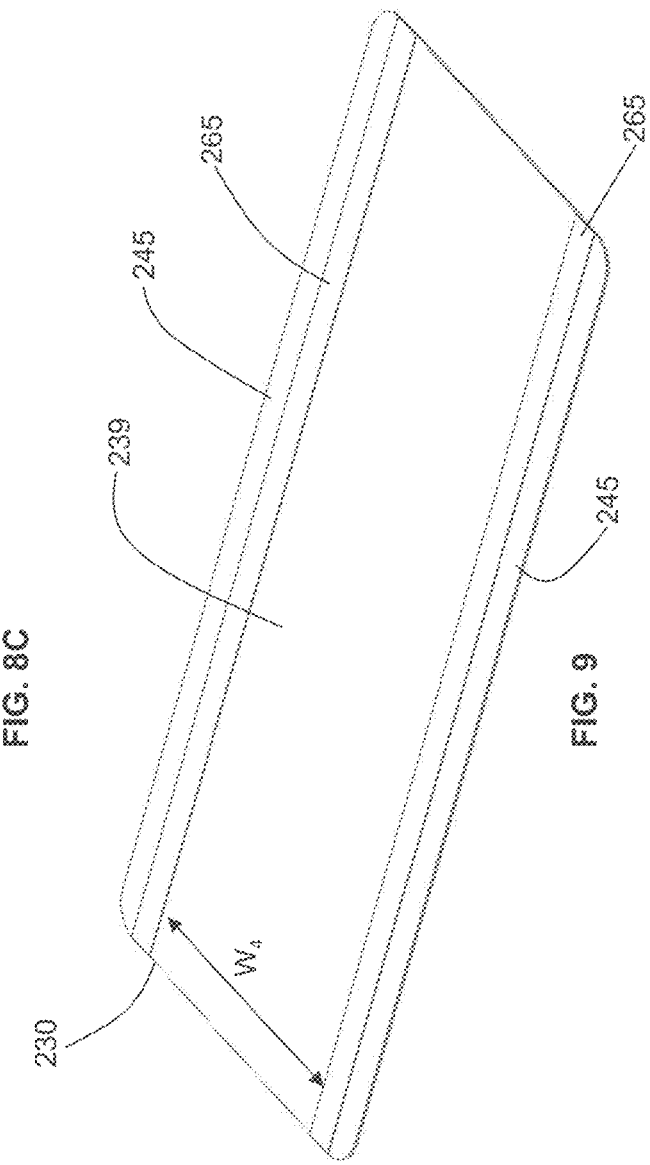
FIG. 9 is a top perspective view of the dressing and packaging assembly of FIG. 7 after release.
Figure 10:
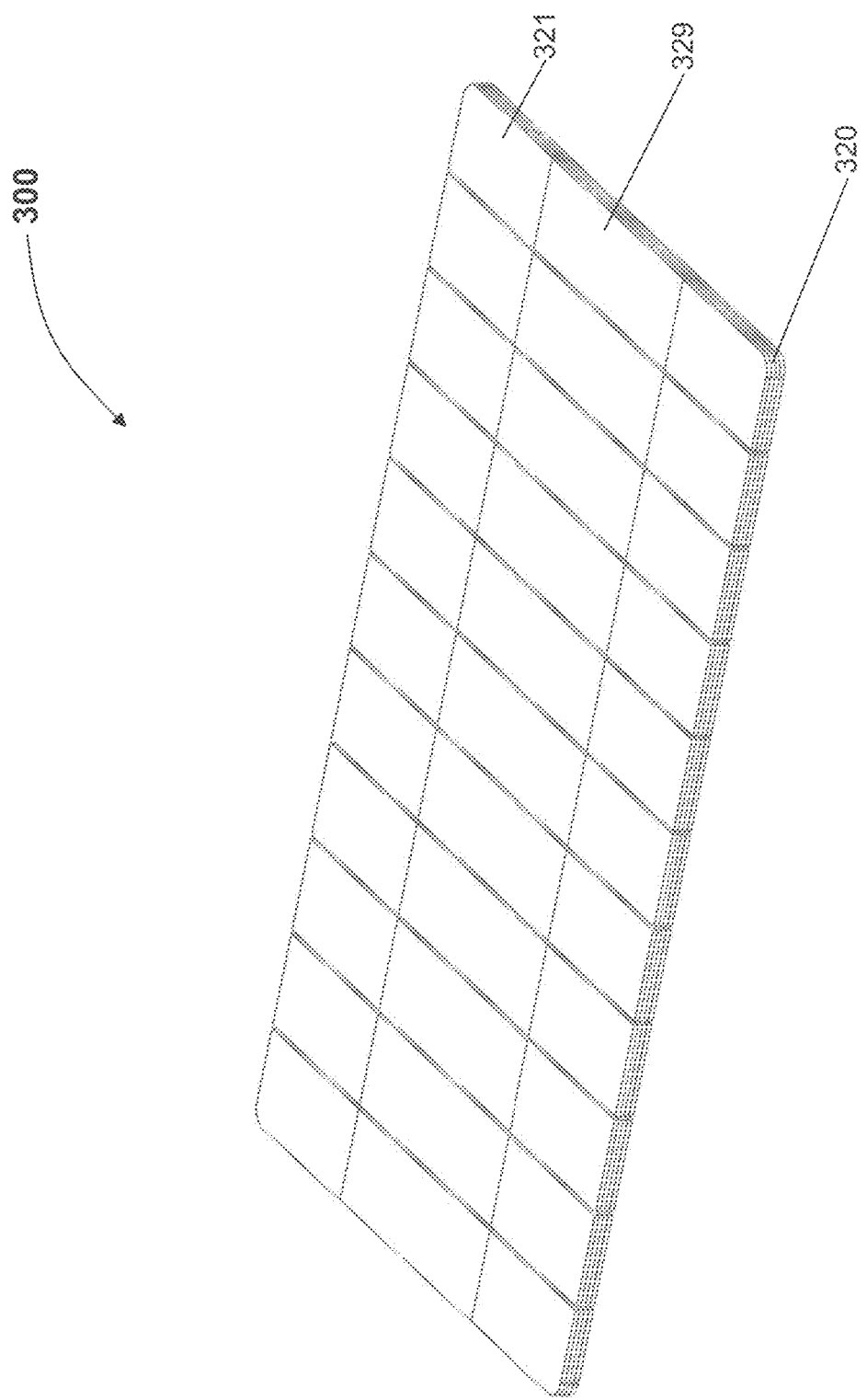
FIG. 10 is a perspective view of another example of a dressing and packaging assembly in a closed configuration
Figure 11:
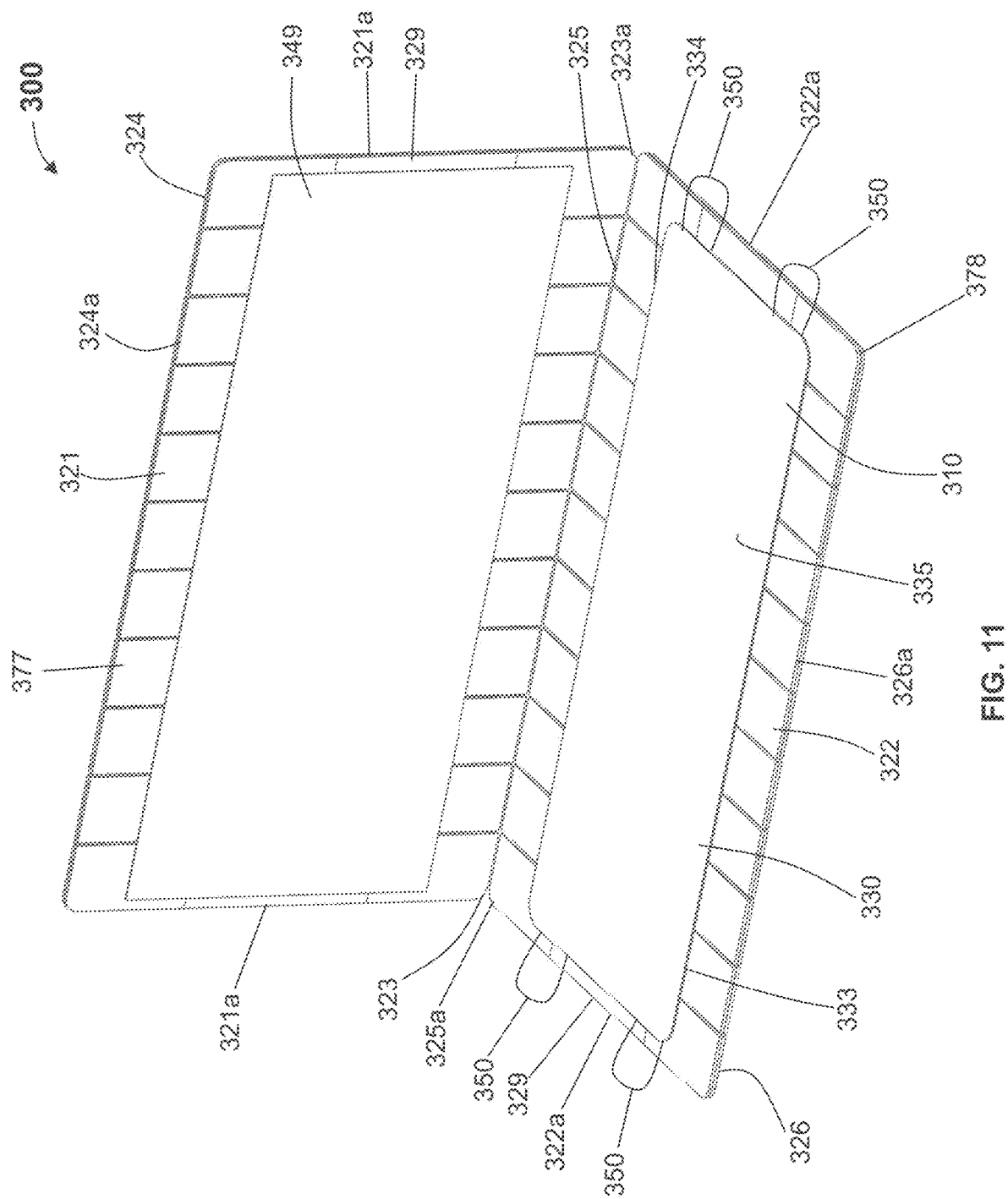
FIG. 11 is a perspective view of the dressing and packaging assembly of FIG. 10 with a cover in approximately 90 degree configuration from the closed configuration.
Figure 12A:
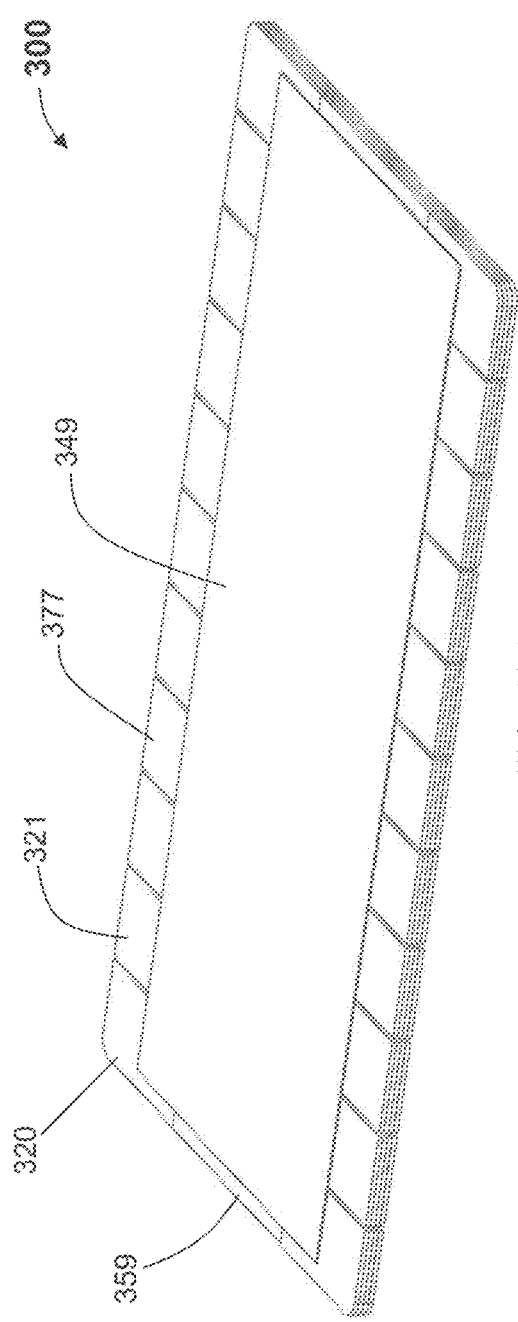
FIG. 12A is a top perspective view of the dressing and packaging assembly of FIG. 10 with a cover in approximately a 360 degree configuration from the closed configuration.
Figure 12B:
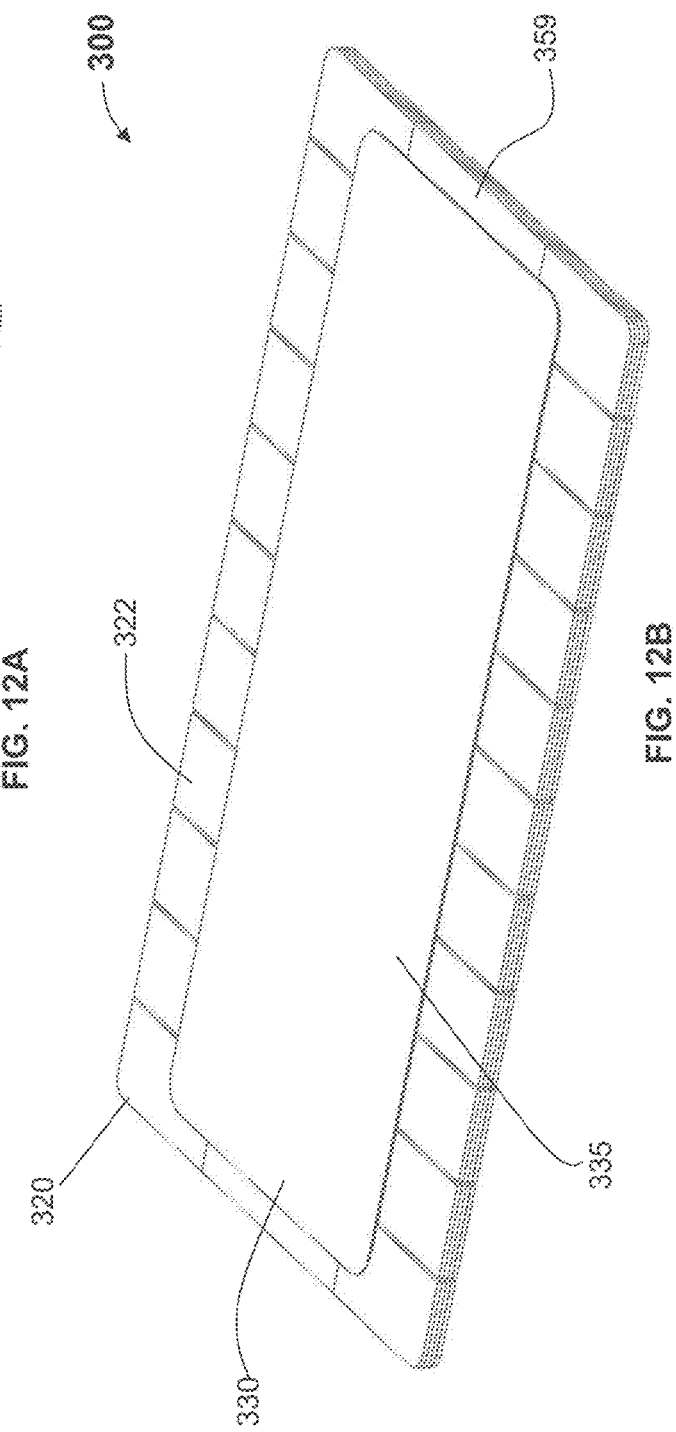
FIG. 12B is a bottom perspective view of the dressing and packaging assembly of FIG. 10 with a cover in approximately a 360 degree configuration from the closed configuration.

Referring to FIGS. 7 to 9, another variation of a dressing and packaging assembly 200 is illustrated. The packaging assembly 200 comprises an applicator and/or tensioning device 220 and a dressing assembly 210 including a dressing 230. The dressing 230 comprises an elastic sheet 231 with one or more adhesive regions comprising a layer of skin adhesive 235. The adhesive used may be, for example, a suitable pressure activated adhesive (PSA), or a non-pressure sensitive adhesive.

The packaging assembly 200, applicator or tensioning device 220, and/or dressing assembly 210 may be configured to pre-strain the dressing 230 and/or permit transfer of the pre-strained dressing 230 to the skin of a subject. The applicator or tensioning device 220 may also provide for a convenient sterile transfer of an adhesive portion of the dressing to a skin and/or wound site of a subject.

The device 220 may comprise a cover 221 and a base 222. The dressing assembly 210 is removably coupled or anchored to the device 220, and may serve as a dressing carrier. The cover 221 may be generally planar and include sides 223, 224 with corresponding edges 223a and 224a defining its length and edges 221a at opposing ends. The base 222 may be generally planar and include sides 225, 226 with corresponding edges 225a and 226a defining its length and edges 222a at opposing ends.

According to some variations, the cover and/or base 221,222 or elements or segments thereof may be constructed to be sufficiently firm or rigid or less flexible relative to an attached dressing to support an attached dressing until it is applied to a subject as described with respect to the variations herein. Such material may comprise, for example, a plastic, e.g., polypropylene, polycarbonate, PTFE, LDPE, HDPE, UHMWPE, PVC or acrylic, nylon or a paperboard. The elements or segments may be a laminate of a material, such as a solid bleach sulfate paperboard with a layer of flexible material between layers of paperboard, for example, silicone, polyurethane, low-density polyethylene or a rubber material, The material may also be a metal as for example, ductile aluminum or stainless steel. The metal may comprise a foil, ribbon, wire or other form. The other variations as described for application or tensioning device 100 may be applied to device 200 also.

The cover and base 221 and 222 may be movably, pivotably, bendably or hingedly coupled at sides 223, 225 in a manner similar to that described with respect to cover and base 121, 122 herein and may be constructed in a manner similar to cover and base 121, 122 herein, among other things, with segments 227 similar to segments 127 and dressing 230 attached to device 220 and strained by device in a similar manner as dressing 130 is attached to device 120.

The various attached structures, e.g. the segments and/or the cover and base and coupling elements may provide a structural support for the dressing carrier to be manipulated by a user. Margins between at least a portion of the structural support elements, dressing carrier or backing and the strained or unstrained dressing may be provided at or near edges 221a, 223a, 224a, 222a, 225a, and/or 226a, such as, for example, margins m1, m2, m3 shown in FIG. 3 herein.

According to some variations, each of the cover 221 and base 222 is constructed at least in part of a clear plastic, semi-opaque or other material that provides a window portion 259 through which a wound, incision or other location may be visualized for accurate placement of the dressing 230. The cover 221 and base 222 may or may not comprise the same material. The elastic sheet 231 and adhesive layer 235 may also be sufficiently clear to permit visualization through them. A more opaque material may be provided on portions of the material to create boundaries of a window. Segments 227 may be clear or semi-opaque to provide a window for viewing, positioning, and/or centering the location of a wound or position on skin with respect to the dressing 230 or for positioning the wound within an optimal or most effective strain zone of the dressing. The boundaries or other markings may assist a user in placing the dressing in an appropriate position over the wound or incision.

The dressing assembly 210 also includes an attachment sheet 241, attachment sheet 251, and a dressing release structure or mechanism 250 comprising pull tabs 246 as described in more detail herein. The dressing 230 of the dressing assembly 210 has a first side 233 having a length, and a second side 234 having a length. When the device 220 is closed, the adhesive layer 235 faces away from the base 222 and is covered by a release liner 249 that is attached to the inside surface 277 of the cover 221.

The attachment sheet 241 has a first side 243 and a second side 244. The attachment sheet 241 couples the dressing 230 to the cover 221 of the device 220 near the second side 234 of the dressing 230. The cover 221, when opened, exerts a straining force on the dressing 230 through the attachment sheet 241. The attachment sheet 241 is coupled at its side 244 to the cover 221 at attachment points 237, which may be provided as an attachment line or area 237a, for example, by bonding with a low surface energy PSA such as an acrylic adhesive. When assembled, the attachment sheet 241 is bonded to the elastic sheet 231 of the dressing 230 at section 265 of attachment sheet 241 at or near the side 243 of the attachment sheet 241, for example, using a combination of a silicone PSA/acrylic PSA. The attachment sheet 251 has a first side 253 and a second side 254. The attachment sheet 251 couples the dressing 230 to the base 222 of the device 220 near the first side 233 of the dressing 230. The attachment sheet 251 is coupled at its side 254 to the base 222 at attachment points 238 defining the attachment line or area 238a, for example, by bonding with a low surface energy PSA, such as an acrylic adhesive. When assembled, the attachment sheet 251 is bonded to the elastic sheet 231 of the dressing at section 265 of attachment sheet 251 at or near the side 253 of the attachment sheet 251, for example, using a combination of a silicone PSA/acrylic PSA.

Dressing 230 has unattached portions or edges 255 at its sides 233, 234 where the elastic sheet 231 is free from the attachment sheets 241, 251 respectively. Accordingly, the dressing 230 is not strained at unattached portions 255. The pull tabs 246 are each coupled to ends 281, 282 of the device 220. Each pull tab 246 comprises a top section 247 and bottom section 248. The bottom sections 248 are attached to the base 222 or cover 221 as illustrated while top sections 247 are adjacent but unattached to the dressing 230.

According to some variations, the attachment sheets 241, 245 are flexible while being relatively inelastic with respect to the dressing 230 and may be constructed, e.g., out of a low density polyethylene. The attachment sheets 241, 245 may be manufactured to be tearable along the material length while providing tensile strength in other directions, in particular in the tensioning direction of the material of the attachment sheet 241 (direction in which dressing is tensioned, stressed or strained). An example of such material is an LDPE polymer which is produced by an extrusion process that creates a directionally biased grain whereby the material is tearable with the direction of the grain, but has a relative resistance to tearing in the direction transverse to the grain. The pull tab 246 may start a tear at a notch in the attachment sheet 241 or 251 that is to be completed along lines 262. The attachment sheets 241, 251 may additionally or alternatively comprise a material such as an LDPE with perforations formed along tear lines 262.

Similar to assembly 100 herein, when the assembly 200 is in a closed configuration and at an open 90 degree configuration as shown in FIG. 7, the elastic sheet 231 is relaxed or unstrained, with the elastic sheet 231 having an unstrained width w3. As the assembly 200 is opened to 180 degrees or up to 360 degrees (e.g. by rotating or pivoting the cover 221 with respect to the base 222), the orthogonal distance increases between lines or areas of attachment 237a, 238a. When the device 220 is opened, it exerts a separation force between attachment regions defined by attachment lines or areas 237a, 238b or corresponding attachment areas. The force tensions the elastic sheet 231 creating a strain. Tensioning and imparting a strain on the dressing 230 increases the width between attachment lines or areas 237a, 238a to width w4. The increase in the width (i.e. width w4 minus width w3) may be a percentage of w3 or a percent strain as described herein. While straining is illustrated as starting when the cover 221 is opened about 90 degrees from the base 222. The dressing 230 may be attached to the cover 221 at a number of locations or in a number of configurations that may vary at which position or configuration the cover 222 may be when the straining begins.

As shown in FIGS. 8A to 8C, the cover 221 and base 222 may be rotated an additional amount, with respect to each other, e.g., up to approximately 360 degrees from the closed configuration prior to applying the dressing 230. According to some variations the assembly is opened to no less than about 180 degrees (minimum angular change) to provide for application of the dressing without interference from the assembly.

Then, once the cover 221 is opened and the adhesive layer 235 is exposed, the adhesive side of the dressing 230 may be place on a skin or wound site using the device 220. The cover 221 and base 222 may be rotated an additional amount, with respect to each other, e.g., up to approximately 360 degrees from the closed configuration prior to applying the dressing 230. The orientation of the cover 221 at which the dressing 230 begins to strain may be varied, e.g. by varying the attachment location of the dressing assembly 210 to the cover 221. A locking mechanism may optionally be provided to lock or secure the device in an open, partially opened or closed position. In some examples, the locking mechanism may comprise magnets, hook-and-loop attachment structures, snaps, latches, clips and the like.

The adhesive layer 235 of the elastic sheet 231 is protected by a release liner 249 before the applicator and tensioning device 220 is opened. The release liner 249 is attached to the inside surface 277 of the cover 221 so that when the cover 221 is opened and is separated from the base 222, (prior to straining the elastic sheet 231) the release liner 249 is pulled away from the elastic sheet 231 exposing the adhesive layer 235 prior. Alternatively, as shown in FIG. 6, a release liner 149a may be provided on the adhesive layer 235 that is not attached to the cover 221. When the device 220 is opened, but prior to straining, the release liner 149a may be manually removed from the elastic sheet 231 to expose the adhesive layer 235.

After the liner 249 or 149a is released and the dressing 231 is strained, the dressing 230 may be applied to a desired location on a subject's skin. The window may be used to visualize proper placement. The user may apply pressure to the back side 229 of the device 220 to activate the adhesive on the dressing 231 and/or to apply compression to a wound. If the cover 221 is rotated to 360 degrees, pressure may be applied to the inside 277 of the cover 221. Once applied to a subject, the dressing 230 may be released from applicator or tensioning device 220 using the release mechanism 250.

The pull tabs 246 of the release mechanism 250 each extend proud of the end 236a of elastic sheet 231. Each release pull tab 246 is attached to the dressing assembly 110 in a manner that defines tear paths 262 along which the tabs 246 are pulled to separate the dressing 230 from the device. Notches or perforations may be made in the attachment sheets 241, 251 that facilitate tearing along paths 262.

The dressing 230 is applied to a subject. The dressing 230 may then be released from the device 220 by pulling the tabs 246 to draw the tabs 246 across paths 262 of the attachment sheets 241, 251. The sections 245 of the attachment sheets 241, 251 that bonded to the pull tabs 246 are thereby separated from the attachment sheets thereby separating the sections 265 of the attachment sheets that are attached to the dressing 230 are from the remainder of the attachment sheets 241 and 251 that are attached to the cover 221 and base 222 respectively. Thus, the dressing 230 is released from the remainder of the packaging 100 as shown in FIG. 9. Sections 265 of the attachment sheets 241, 251 may remain on the back surface 239 of the silicone sheet 231 as shown in FIG. 9. Unattached sections 245 of the elastic dressing 230 are unstrained and may be free from the adhesive of the adhesive layer 235 (or may have a reduced amount of adhesive thereon). Thus less stress occurs at the unattached sides or edges defined by sections 245.

Referring to FIGS. 10 to 12B, a dressing and packaging assembly 300 is illustrated. The packaging assembly 300 comprises a packaging device applicator 320 and a dressing assembly 310 including a dressing 330.

The packaging device or applicator 320 is configured to permit transfer of the dressing 330 to the skin of a subject and may also provide for a convenient, expeditious or sterile transfer of an adhesive portion of the skin treatment device to a skin and/or wound site of a subject.

The packaging device or applicator 320 comprises a cover 321 and a bottom element, dressing carrier or base 322, to which dressing assembly 310 is removably coupled or anchored. The cover 321 may be generally planar and include sides 323, 324 with corresponding edges 323a, 324a defining its length and edges 321a at opposing ends. The base 322 may be generally planar and include side 325, 326 with corresponding edges 325a, 326a defining its length and edges 322a at opposing ends.

According to some variations, the cover 321 and base 322 are constructed in part of a relatively inflexible material, e.g., with respect to an attached dressing 330. Such material may comprise, for example, a plastic, paperboard or a laminate of a material, or metal as described herein with reference to cover 121 and base 122. The cover or base may be constructed in a manner as described, for example, with respect to the various applicator, tensioning devices or dressing carriers shown in FIGS. 1 to 22B herein. The cover 321 and base 322 may or may not comprise the same material.

Cover 321 and base 322 may be movably, pivotably, bendably or hingedly coupled at sides 323, 325 and otherwise constructed in a manner similar to that described herein with respect to cover 121 and base 122. The packaging device or applicator 320 may include a window portion 359 through which a wound, incision, or other location may be visualized for accurate placement of the dressing 330 in a manner similar to that described herein with respect to the use of windows 159, 259.

The assembly 300 is constructed including a dressing assembly 310 with a skin dressing device 330. The dressing assembly 310 also includes a dressing release structure or mechanism 350 which may be a release device such as various release and removal structures described herein with reference to FIGS. 1 to 22B. The dressing 330 may comprise a variety of dressing materials, including but not limited to elastic bandages, gauze type bandages, hydrocolloids. The various structures, e.g. the segments and/or the cover and base and coupling elements may provide a structural support for the dressing carrier to be manipulated by a user. Margins between at least a portion of the structural support elements, dressing carrier or backing and the dressing may be provided at or near edges 321a, 323a, 324a, 322a, 325a, and/or 326a, for example as described herein.

When assembled with the packaging device or applicator 320, the dressing 330 is coupled to the base. A length of the dressing 330 adjacent its first side 333 is bonded to a length of the base 322 adjacent its side 324 and outside of release 350. Also a length of the dressing 330 adjacent its second side 334 is coupled to a length of the base 322 adjacent its side 325 and outside of release 350. An attachment sheet similar to sheets 141, 146 or 241, 251 may be used to attach sides 333, 334 of dressing 330 to the base 322. The adhesive layer 335 faces away from the cover 321 and base 322 when the applicator 320 is opened.

According to variation, the dressing 330 is sufficient large with respect to the device 320 so that when applied to the skin, there is relatively less interference by the device 320. According to one example, the width of the strained portion of the dressing may be about 20 mm, about 30 mm, about 40 mm, or about 50 mm. According other variations, the distance between each of edges 333a, 334a of the dressing 330 and the edges 325a, 326a of the base 322 respectively (and/or the edges 323a, 324a of the cover 321) is no greater than about 10 mm, 15 mm or 20 mm. According to variations the distance between the edges 336a, 336b of the dressing and the edges 322a of the base is no greater than about 10 mm, about 15 mm or about 20 mm.

According to some variations, edges 333, 334, 336a, 336b of the dressing 330 are at least about 3 mm inward of at least a portion of the edges 325a, 326a, and/or 322a of the base 322 so that the edges 325a, 326a, and/or 322a of the base 322 may be gripped by a user with a reduced likelihood of touching the dressing 330 or the adhesive layer 335. According to some variations, the ends 336a, 336b of the dressing 130 have a margin of at least about 3 mm inward of the ends 322a of the base 322. According to some variations the sides 333, 334 and ends 336a, 336b of the dressing 330 have a margin of about 10 mm from the sides 325, 326 and ends 322a of the base respectively. According to some variations the sides 333, 334 and ends 336a, 336b of the dressing 330 have a margin of about 15 mm from the sides 325, 326 and ends 322a of the base respectively. Each of the margins between edges 333,334 or ends 336a, 336b of the dressing 330 and sides 325, 325, and ends 322a of the base 322 may be different. As illustrated in FIG. 3, for example, margins m1 and m2 are about no less than 3 mm and margin m3 is about 15 mm Similar margins may be provided between the dressing 330 and the edges 322a, 325a, and/or 326a of the base 322, Also similar margins may be provided between the dressing 330 and the edges 321a, 323a, and/or 324a of the cover 321, for example if the edges of the cover 321 are used alternatively or additionally to grasp the device 320 or manipulate the dressing 330.

The adhesive layer 335 on the dressing 330 may be protected by a release liner 349 before the packaging device or applicator 320 is opened. The release liner 349 may be attached to the inside surface 377 of cover 321 so that when the cover 321 is opened or is separated from the base 322, the release liner 349 is pulled away from the dressing 330 exposing the adhesive layer 335. The release liner 349 may also be a protective liner that protects or covers the dressing prior to application. For example, the liner may cover a dressing to which a substance or medicament or other agent is applied. One or more hemostatic or coagulative agents may be applied to, or otherwise integrated with dressing to help reduce bleeding. Potential agents include chitosan, calcium-loaded zeolite, microfibrillar collagen, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g. II, VII, VII, X, XIII, Von Willebrand factor), procoagulants (e.g. propyl gallate), antifibrinolytics (e.g. epsilon aminocaproic acid), and the like. In some variations, the agents may be freeze-dried and integrated into the dressing and activated upon contact with blood or other fluid. In some further variations, an activating agent may be applied to the dressing or the treatment site before the dressing is used on the subject. In still other examples, the hemostatic agent may be applied separately and directly to the wound before application of the dressing, or after application to the dressing via a catheter or tube. The devices may also comprise one or more other agents that may be any suitable agent that may be useful in aiding in some aspect of the wound healing process. For example, the active agent may be a pharmaceutical compound, a protein (e.g., a growth factor), a vitamin (e.g., vitamin E), or combinations thereof. Of course, the devices may comprise more than one medicament or agents, and the devices may deliver one or more medicaments or agents. An example of such medicament may include, but is not limited to various antibiotics (including but not limited to cephalosporins, bactitracin, polyxyxin B sulfate, neomycin, polysporin), antiseptics (such as iodine solutions, silver sulfadiazine, chlorhexidine), antifungals (such as nystatin), antiproliferative agents (sirolimus, tacrolimus, zotarolimus, biolimus, paclitaxel), grow factors (such as VEGF) and other treatments (e.g. botulism toxin). The cover 321 may be pulled away or separated in a number of manners. The cover 321 may be opened like a cover of a book. Similar to devices 120 and 220, 420, 520, 620, 720, 820, 920,1020 herein, the elements 321, 322 may be rotated sufficiently to separate the release liner 349 and up to approximately 360 degrees allowing the exposed adhesive side 335 of the dressing 330 to be place on a skin or wound site using the packaging device or applicator 320. According to some variations the assembly 300 is opened to no less than about 180 degrees (minimum angular change) to provide for application of the dressing without interference of the assembly 300. Alternatively, for example, the cover 321 may be attached to the base 322 by an adhesive and may be peeled off of the dressing 330 or the base 322 to which the dressing 330 is coupled. The cover 321 itself may be a removable, or separable release liner that may be peeled from the base 322. Alternatively, as shown in FIG. 6, a release liner 149a may be provided on the adhesive layer 335 that is not attached to the cover 321. When the device is opened, the release liner 149a may be manually removed from the dressing 330 to expose the adhesive layer 335. In such case, the cover 321 may be omitted. After the device 300 is opened to position shown in FIGS. 11 or 12A and 12B, the dressing 330 may be applied to a desired location on a subject's skin. The window 359 may be used to visualize proper placement. A locking mechanism may optionally be provided to lock or secure the device in an open, partially open, or closed position. In some examples, the locking mechanism may comprise magnets, hook-and-look attachment structures, snaps, latches, clips and the like as well as adhesives, or other adhesive structures. A compressive force may be applied to the back side 378 of base 322 or inside 377 of cover if rotated approximately 360 degrees. Once applied to a subject, the dressing 330 may be released from packaging device or applicator 320 using a release mechanism 350. The release mechanism 350 may include a cutting element or a perforated element as described for example with respect to devices 150 and 250 herein. The release mechanism may further include one more release elements described herein and show in FIGS. 1 to 22B.

Figure 13:
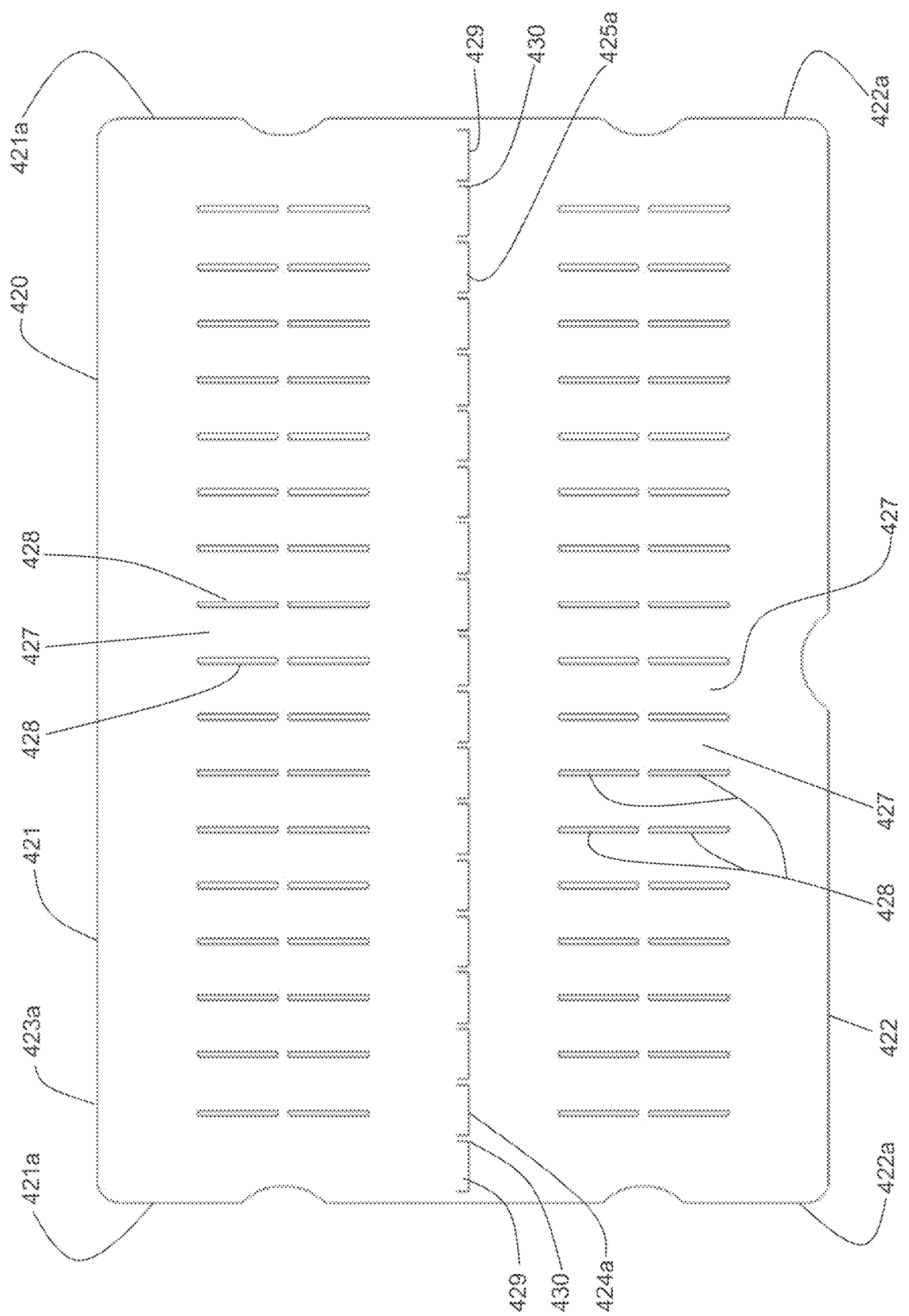
FIG. 13 is a top view of a packaging device in an open configuration.

FIG. 13 illustrates an alternative packaging or applicator 420 that may be used in any of the embodiments herein including device elements or features that may be substituted for device elements or features of devices 120, 220 or 320, 520, 620, 720,820,920, 1020, 1120, 1220. FIG. 13 illustrates a cover 421 and a dressing carrier or base 422 that are constructed of a single substrate out of a material such as nylon and/or polyethylene or a metal. The device 420 may be manufactured from a single mold and/or may have portions cut out of the substrate, slots, grooves, scoring or other openings or variations in thickness of the substrate at different locations. The cover 421 and base 422 each comprise slots 428 that form elements such as segments 427. The slots 428 permit flexion of the device 420 allowing it to conform to a subject's body contours where an attached dressing is to be applied. Cover 421 and base 422 are coupled to each other by way of connection features 429 that are formed in the substrate. The cover 421 and base 422 are hingedly or pivotably moveable with respect to each other by virtue of slots 430 that are formed adjacent connection features 429, to permit flexion or movement of the connector features 429 and thus the cover 421 and base 422 with respect to each other. As mentioned with respect to device 100, in other variations, slots 430 may comprise grooves or other structures providing a reduced thickness relative to the cover 421 and base 422. The device 420 may include a release mechanism as described with respect to FIGS. 1A-22B herein. The device 420 may be used in the same manner as the devices described with reference to FIGS. 1A to 22B herein and may attach a dressing in the same manner as described with respect to devices described with reference to FIGS. 1A to 22B herein.

The various structures, e.g. the segments and/or the cover and base and coupling elements, slots and grooves may provide a structural support as well as flexibility for the dressing carrier to be manipulated by a user. Margins between at least a portion of the structural support elements, dressing carrier or backing and an attached dressing may be provided at or near edges 421a, 423a, 424a, 422a, 425a, and/or 426a, for example as described further herein.

FIG. 14 illustrates an alternative packaging or applicator device 520 that may be used in any of the devices described herein with reference to FIGS. 1A to 22B. A cover portion 521 and a dressing carrier or base portion 522 may be constructed of a laminate structure 530. A first layer 531 of the laminate structure 530 comprises a paperboard or other support material such as a plastic material or metal having slots 528 formed widthwise across each of the cover 521 and base 522. The slots 528 form segments 527 that permit flexion of segments 527 of the device 520 allowing it to conform to a subject's body contours where an attached dressing is to be applied. The first layer 531 further comprises lengthwise slot 529 between the cover 521 and base 522 formed in the first layer 531. The first layer 531 further comprises tabs 540 with openings that are used in assembly of the device 520 and are removed after assembly so that the cover 521 and base 522 are separated by slot 529 and are no longer connected by the first layer 531. The second layer 532 of the laminate comprises an adhesive material such as a PSA acrylic, rubber or silicone adhesive. The second layer 532 may or may not be about 0.001 to 0.006 thick. A flexible strip 534 of material is positioned along the length of the device 520 over the slot 529 and connecting the cover 521 and base 522. The cover 521 and base 522 are flexibly and hingedly or pivotably coupled and moveable with respect to each other by way of the strip 534 of material over the slot 529 to permit flexion or movement of the cover 521 and base 522 with respect to each other. The flexible strip 534 is attached with an adhesive 535 to a third layer 533 that comprises a thin material such as paper or plastic that may have generally a similar outline as the first layer 531 and that holds the structure of the device 520, including segments 527, together.

The device 520 may include a release mechanism, dressing attachment and may be used in the same manner devices and assemblies as described with respect to FIGS. 1A-22B herein.

The various structures, e.g. the segments, adhesive structures, laminate layers and/or the cover and base and coupling elements, slots and grooves may provide structural support as well as flexibility for the dressing carrier, to facilitate manipulation by a user. Margins between at least a portion of the structural support elements, dressing carrier or backing and an attached dressing may be provided at or near edges 521a, 523a, 524a, 522a, 525a, and/or 526a, for example as described further herein.

Referring to FIGS. 15A to 15J, a variation of a dressing and packaging assembly 600 is illustrated. The packaging assembly 600 comprises an applicator and/or tensioning device 620 and a dressing assembly 610 including a dressing 630. The dressing 630 comprises an elastic sheet 631, with one or more adhesive regions comprising a layer of skin adhesive such as described herein.

The features in FIGS. 15A to 15J may be used in any of the variations herein including device elements or features that may being substituted for device elements or features of devices and assemblies shown in FIGS. 1A to 22B.

The packaging assembly 600 applicator, tensioning device 620 and/or dressing assembly 610 may be configured to pre-strain the dressing 630 and/or permit transfer of the pre-strained dressing 630 to the skin of a subject. The applicator or tensioning device 620 may also provide for a convenient sterile transfer of an adhesive portion of the dressing to a skin and/or wound site of a subject.

The device 620 comprises a cover 621 and a base 622. The dressing assembly 610 is removably coupled or anchored to the device 620 which may act as a dressing carrier. The cover 621 may be generally planar and include sides 623, 624 with corresponding edges 623a and 624b defining its length and edges 621a at opposing ends. The base 622 may be generally planar and include sides 625, 626 with corresponding edges 625a and 626a defining its length and edges 622a at opposing ends.

According to some variations, the cover 621 and/or base 622 or elements or segments thereof may be constructed to be sufficiently firm or rigid or less flexible relative to an attached dressing to support an attached dressing until it is applied to a subject as described with respect to the variations herein. The materials and construction of the applicator or tensioning device 620, dressing 630 and packaging 600 may be of similar to the packaging assemblies and/or dressings described in variations herein and shown in FIGS. 1A to 22B.

The cover 621 and base and 622 may be movably, pivotably, bendably or hingedly coupled at sides 623, 624. For example, a layer of material 627 such as silicone, polyurethane, low-density polyethylene or a rubber material may be glued to each of the cover and base, flexibly attaching them together at sides 623, 625. The device 620 may be constructed in a manner similar to that described with respect to other devices herein and shown in FIGS. 1A to 22B and may be constructed in a similar manner as described herein including but not limited to with respect to materials, segmentation, strength and flexibility, visualization, straining mechanisms, and release liners.

The dressing assembly 610 also includes an attachment sheet 641, attachment sheet 651. The attachment sheet 641 has a first side 643 that is attached to the second side 634 of the dressing by way of an adhesive structure 670 such as polyimide film or tape (e.g. KAPTON® by DuPont™) or a peelable adhesive. Adhesive structures herein may include but are not limited to KAPTON® tape or peelable adhesive configured to provide low skin trauma after repeated skin contact or a soft skin adhesive, made of material such as silicone adhesive, silicone gel, or acrylic adhesive. The adhesive structure or KAPTON® tape also comprises a material that is able to adhere to the attachment sheets to impart strain to the dressing when the attachment sheets are separated from each other, while being peelable from a selected dressing material.

As shown in FIG. 15J, the attachment sheet 641 and side 634 of the dressing may be attached on same side 671 of the adhesive structure 670 with the attachment sheet 641 overlapping but unattached to the dressing 631.

The attachment sheet 641 has a second side 644 that is coupled to the cover 621 of the device 620 for example, by bonding with a low surface energy PSA, such as an acrylic adhesive. Attachment sheet 641 may also have a score or perforation 681 between its attachment to the adhesive structure 670 and its attachment to the cover 621. After the dressing has been strained, the perforation 681 is located at the seam between the cover 621 and the base 622, or over the inside surface of the cover 621.

The attachment sheet 651 may be coupled at its side 654 to the back side 698 of the base 622 for example, by bonding with a low surface energy PSA, such as an acrylic adhesive. The side 653 of attachment sheet 651 may be attached to the side 633 of the dressing by way of an adhesive structure 680 such as KAPTON® tape or a peelable adhesive, and in a manner similar to the adhesive structure 670 that attaches the side 654 of the dressing 630 to the attachment sheet 641. The attachment sheet 651 may include a pull tab 688 that is located on the back side 698 of the base adjacent and inside of the attachment zone 655 of the attachment sheet 651 to the back of the base 652.

The cover 621, when opened, exerts a straining force on the dressing 630 through the attachment sheet 641.

According to some variations, the attachment sheets 641, 651 are flexible while being relatively inelastic with respect to the dressing 630 and may be constructed, e.g., out of a low density polyethylene. The attachment sheets 641, 651 may be manufactured to be tearable along the material length while providing tensile strength in other directions, in particular in the tensioning direction of the material of the attachment sheet 641 (direction in which dressing is tensioned, stressed or strained). An example of such material is an LDPE polymer which is produced by an extrusion process that creates an anisotropic or directionally biased grain whereby the material is tearable with the direction of the grain, but has a relative resistance to tearing in the direction transverse to the grain.

Figure 15A:
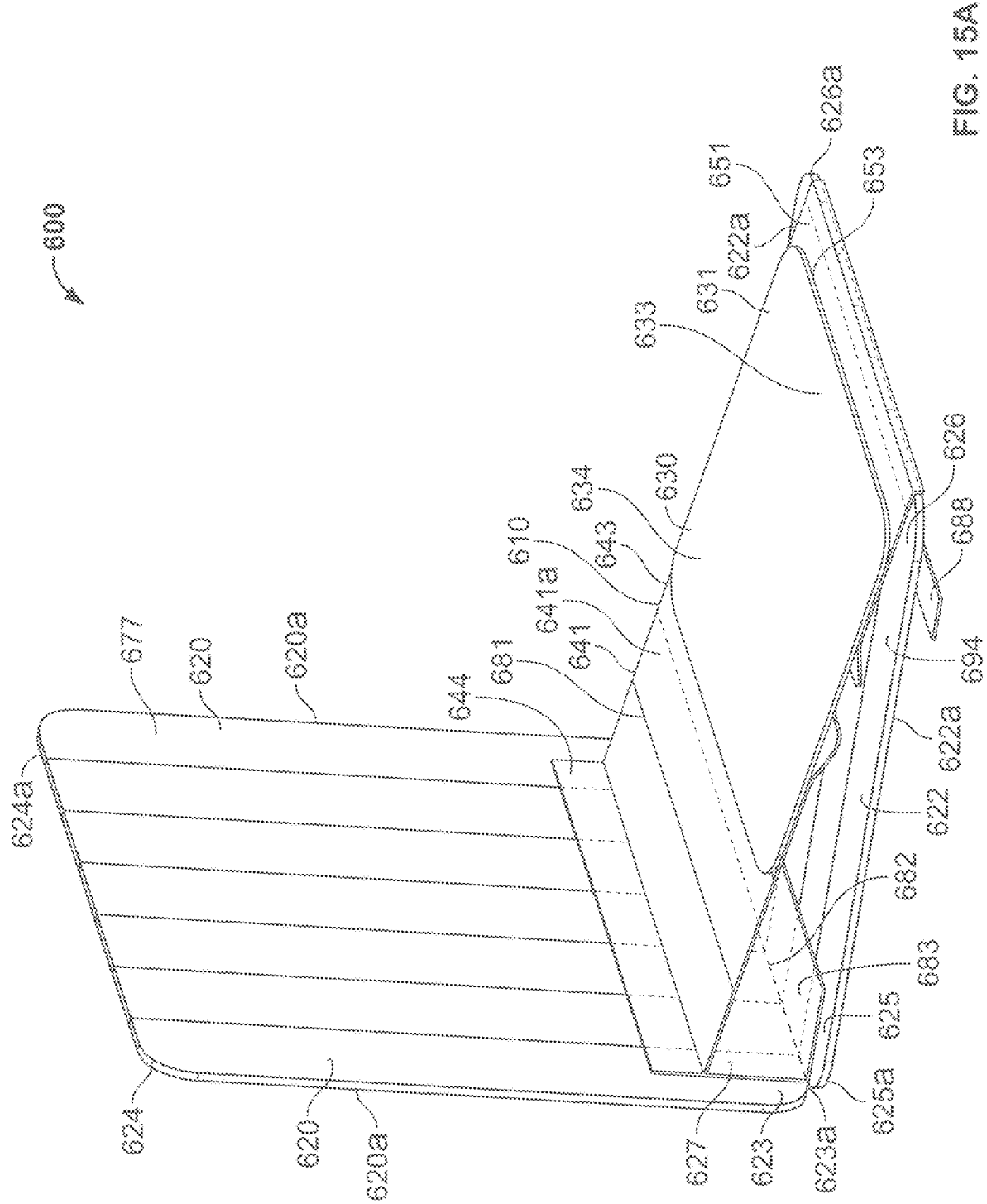
FIG. 15A is a perspective view of a variation of dressing and packaging assembly in an unstrained configuration.

FIG. 15A shows the assembly 600 in an unstrained configuration. An adhesive tape 683 is exposed on the inside surface 694 of the base 622. A skin adhesive layer on the elastic sheet 631 of the dressing 630 may be protected by a release liner similar to release liner 149a herein before the applicator or tensioning device 620 is opened FIG. 15B shows the assembly 600 in an opened and strained configuration. As shown in FIG. 15B, when strained, the perforation 681 on the attachment sheet is aligned with the edges 623a and 625a of the cover 621 and base 622, respectively. A portion 641a of the attachment sheet 641 interfaces with the adhesive tape 683 attaching portion 641a to the base 622 and holding the dressing 630 in the strained configuration. A release liner 645 is attached to the underside of the attachment sheet 641 between the attachment to the cover 621 and the perforation 681. The liner 645 prevents the portion of the attachment sheet 641 that interfaces the cover 621 from adhering to the adhesive tape 683.

The cover 621 and base 622 may be separable from each other by way of, for example, a perforation 682 in the layer 627 that couples the cover 621 to the base 622 and by separation of the sheet 641 along perforation 681. FIG. 15C shows the assembly 600 with the cover 621 separated from the base 622. The strained dressing 630 may be applied to a subject's skin using the base 622 as an applicator.

FIG. 15D illustrates the back side 698 of the base 622 in a position of applying the dressing 630 toward the skin of a subject. As shown, the edge 654 of attachment sheet 651 may be wrapped around from the inside 694 of the base 622 to the back side 698 where it is attached. A tear strip may be attached to the attachment sheet 651 between the attached edge and an unattached middle section. The pull tab 688 or tear strip may be pulled to detach the base 622 from the remainder of the dressing assembly as shown in FIG. 15E. After the tab 688 is pulled, an unattached portion 651a of the attachment sheet 651 is freed from the base 622. After the base is removed, the remaining portions of the attachment sheets 641, 651 may be removed by peeling the KAPTON® tape off of the dressing 630. FIG. 15F shows the dressing 630 after removal of the remainder of the dressing assembly.

FIGS. 15G to 15I illustrate a configuration of the dressing assembly 610 as the KAPTON® tape or adhesive structures 670, 680 and attachment sheets 641, 651 are removed from the dressing 630. FIGS. 15G and 15I show the orientation of the KAPTON® tape or adhesive structures 670, 680 as they are peeled in a direction from inside the dressing 630 towards the sides 633, 634 of the dressing 630, or in a direction of dressing strain. FIG. 15H shows the first structure 670 peeled away from the inside of the dressing across the side 633 of the dressing. FIG. 15I shows the first adhesive structure 670 removed from the dressing 630. The second adhesive structure 680 may be removed in a similar manner.

Figure 16A:
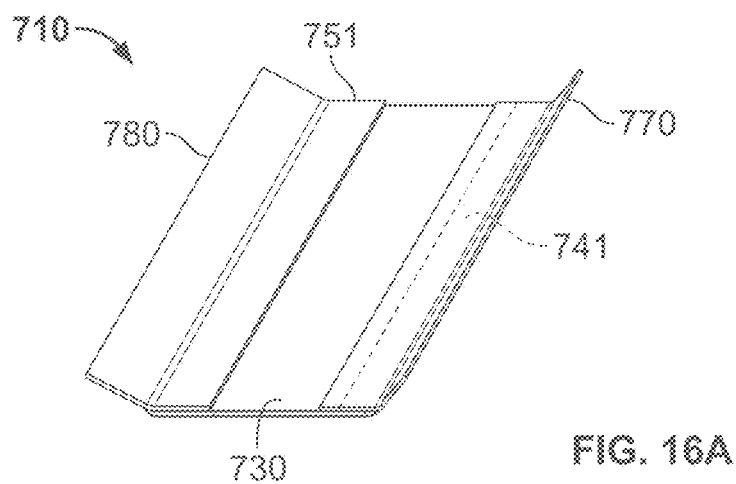
FIG. 16A is a perspective view of a variation of a dressing assembly with removable attachment sheets.
Figure 16B:
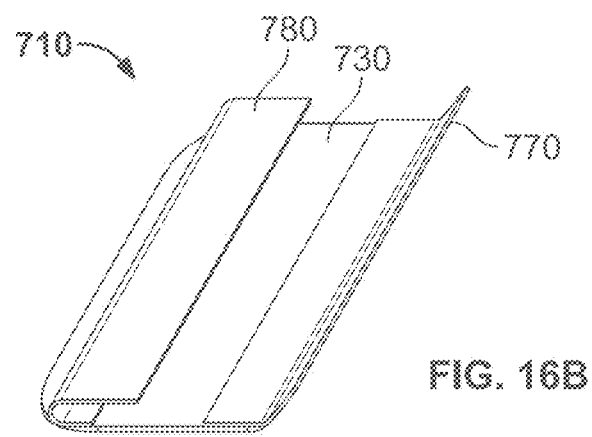
FIG. 16B is a perspective view of the dressing assembly of FIG. 16A with a peeled removable attachment sheet.
Figure 16C:
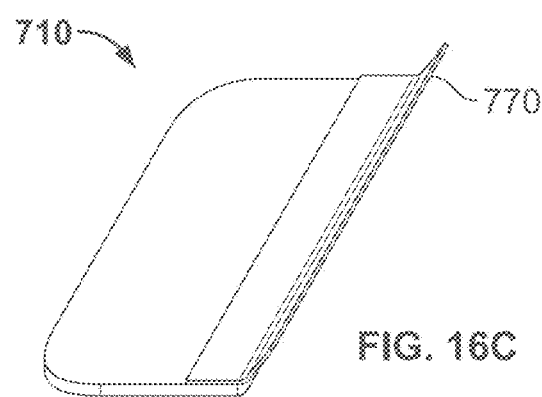
FIG. 16C is a perspective view of the dressing assembly of FIG. 16A with a removed attachment sheet.
Figure 16D:
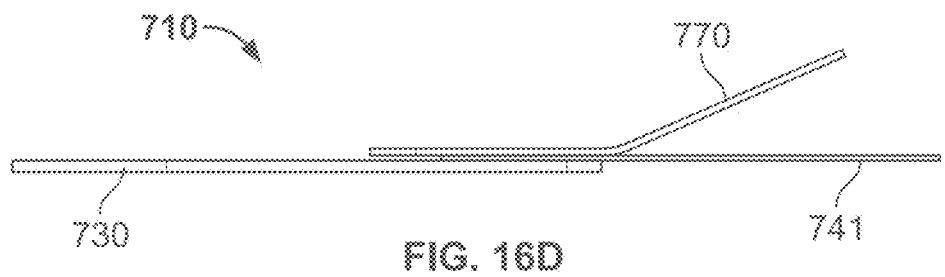
FIG. 16D is a cross section of the dressing assembly with attachment sheets of FIG. 16A

FIGS. 16A to 16D illustrate an alternative dressing assembly 710 in a configuration in which a dressing assembly 710 is separated from the applicator or tensioning device in a manner similar to that described with respect to FIGS. 15A to 15J. FIG. 16A illustrates a first adhesive structure 770 and a second adhesive structure 780, each comprising KAPTON® tape or a peelable adhesive structure used to attach attachment sheets 741, 751 to the dressing 730, As shown in FIG. 16A the unattached ends of the adhesive structures 770, 780 are oriented away from the dressing 730. As shown in FIG. 16B, the second adhesive structure 780 is peeled inwardly and in FIG. 16C, is removed.

Figure 17A:
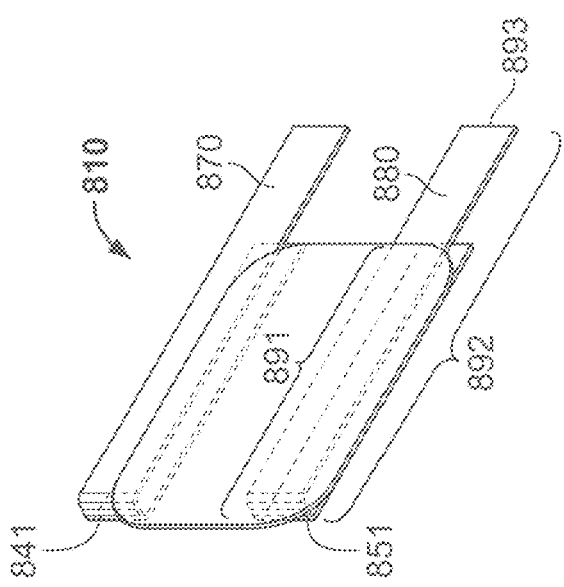
FIG. 17A is a perspective view of a variation of a dressing assembly with removable attachment sheets.
Figure 17B:
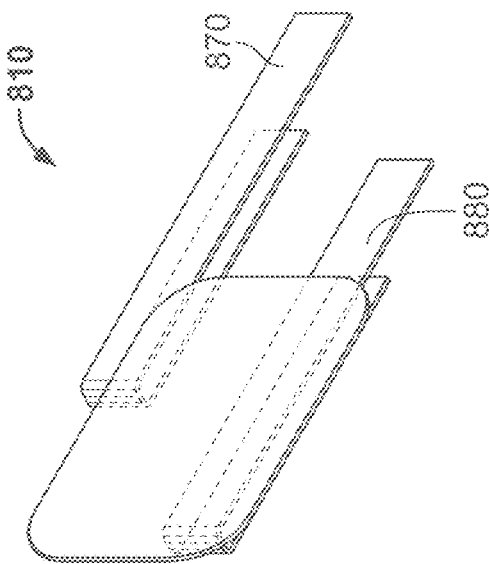
FIG. 17B is a perspective view of the dressing assembly of FIG. 17A with a peeled removable attachment sheet.
Figure 17C:
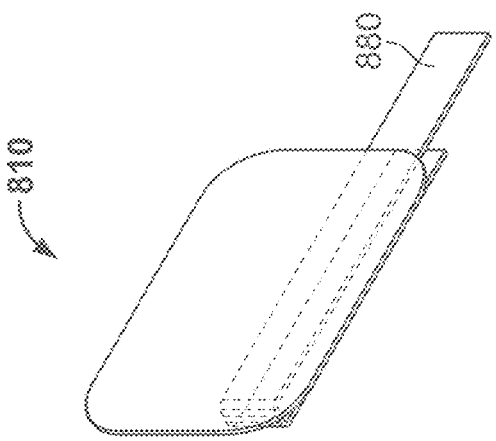
FIG. 17C is a perspective view of the dressing assembly of FIG. 17A with a removed attachment sheet.
Figure 17D:
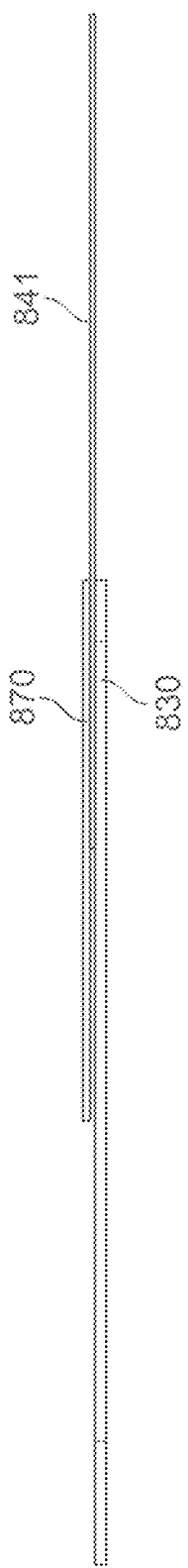
FIG. 17D is a cross section of the dressing assembly with attachment sheets of FIG. 17A.

FIGS. 17A to 17D illustrate an alternative dressing assembly configuration in which a dressing assembly 810 is separated from the applicator or tensioning device in a manner similar to that described with respect to FIGS. 15A to 15J. FIG. 17D illustrates a first adhesive structure 870 and a second adhesive structure 880, each comprising KAPTON® tape or a peelable adhesive structure used to attach attachment sheets 841, 851 respectively to the dressing 830. As shown in FIGS. 17A and 17D, the adhesive structures 870, 880 are attached to the dressing 830 with adhered length 891. An additional length 892 is wrapped 180 degrees about the adhered length 891. The additional length 892 has an end 893 that extends proud of the dressing 830 for easy access and removal. As shown in FIG. 17B, the first adhesive structure 870 may be pulled using the end 893, in a direction that is in part perpendicular to the direction of strain, to remove the attachment structures 841, 851 and adhesive structure 870 from the dressing 830 as further shown in FIG. 17C.

FIGS. 18A to 18J illustrate a variation of a dressing and packaging assembly 900. The packaging assembly 900 comprises an applicator and/or tensioning device 920 and a dressing assembly 910 including a dressing 930. The device 920 comprises a cover 921 and a base 922. The dressing assembly 910 is removably coupled or anchored to the device 920 which may act as a dressing carrier. The cover 921 may be generally planar and include sides 923, 924 with corresponding edges 923a and 924a defining its length and edges 921a at opposing ends. The base 922 may be generally planar and include sides 925, 926 with corresponding edges 925a and 926a defining its length and edges 922a at opposing ends.

The dressing assembly 910 also includes an attachment sheet 941 and attachment sheet 951. The attachment sheet 941 has a first side 943 that is attached to the second side 934 of the dressing by way of an adhesive structure 970 such as KAPTON® tape or a peelable adhesive. Adhesive structures herein may include but are not limited to KAPTON® tape or peelable adhesive configured to provide low skin trauma after repeated skin contact or a soft skin adhesive, made of material such as silicone adhesive, silicone gel, or acrylic adhesive. The adhesive structure or KAPTON® tape also comprises a material that is able to adhere to the attachment sheets to impart strain to the dressing when the attachment sheets are separated from each other, while being peelable from a selected dressing material.

Figure 18A:
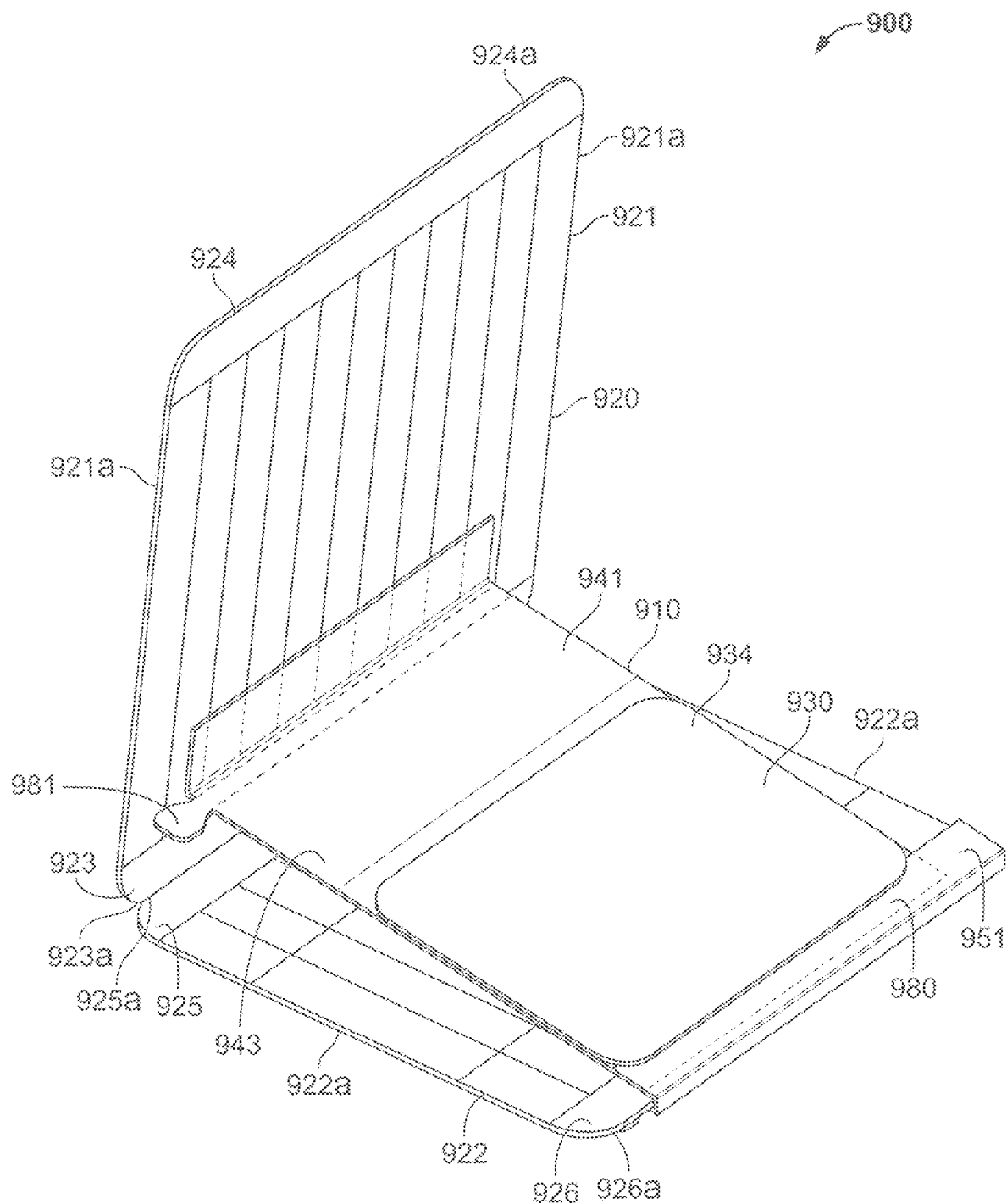
FIG. 18A is a perspective view of a variation of dressing and packaging assembly in an unstrained configuration.
Figure 18B:
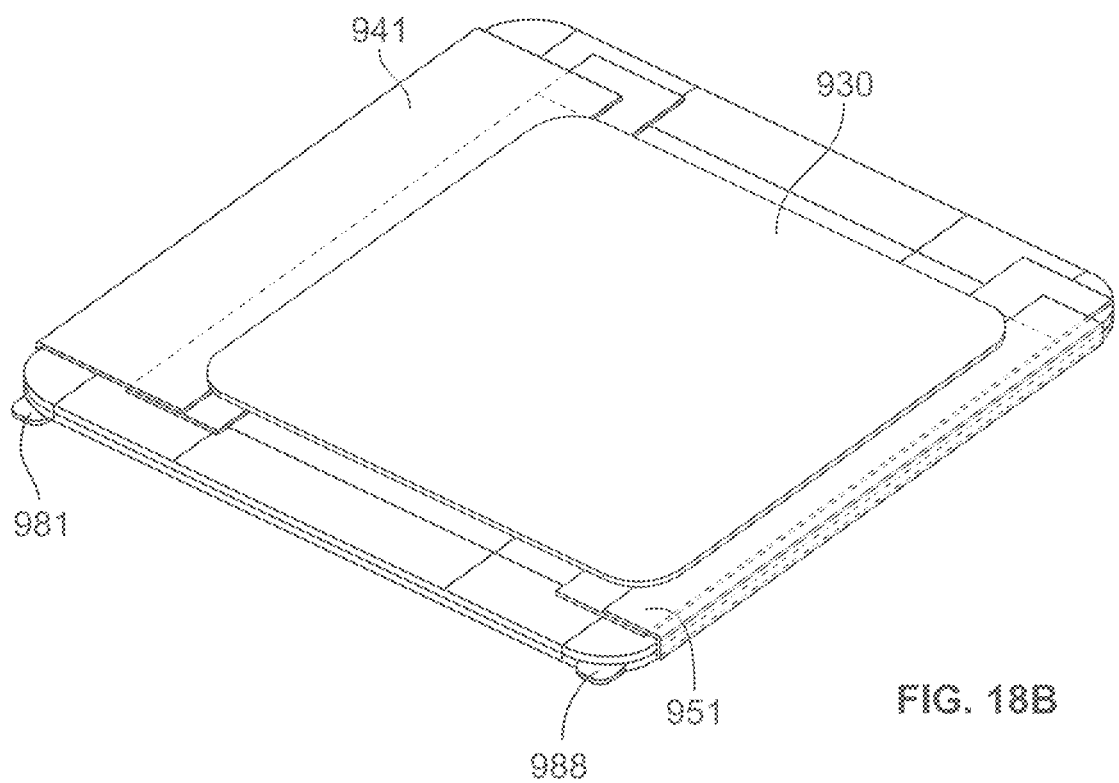
FIG. 18B is a top perspective view of the device of FIG. 18A in a strained and folded configuration.
Figure 18C:
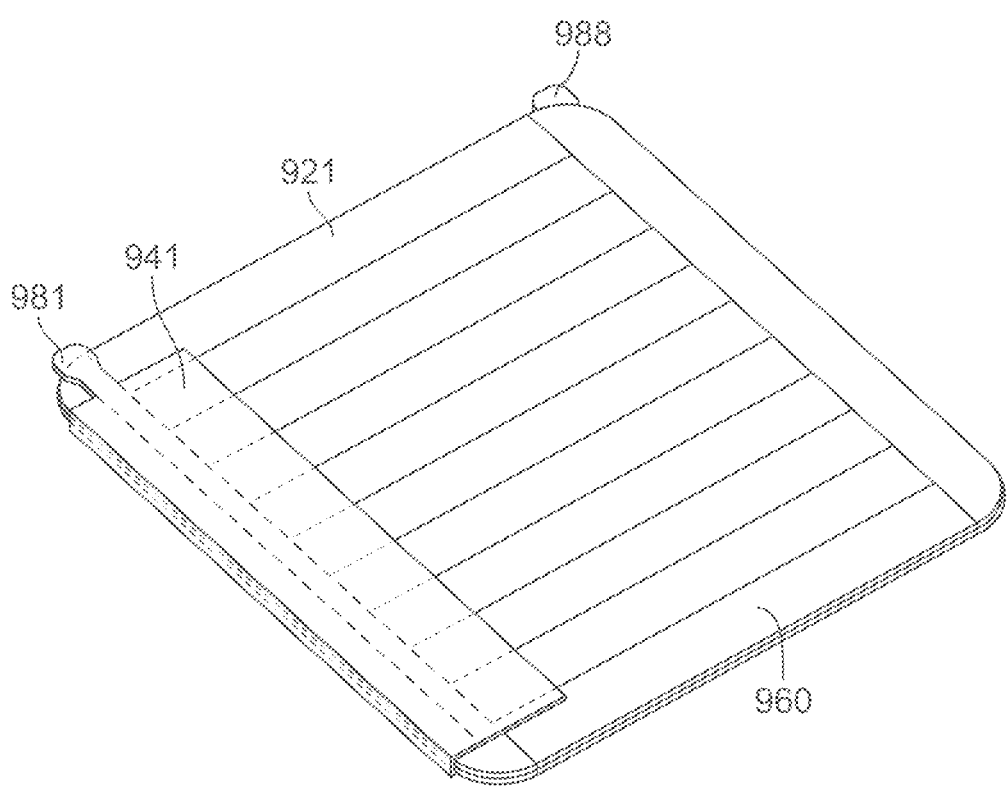
FIG. 18C is a perspective view of the bottom side the device in the strained and folded configuration of FIG. 18B.
Figure 18D:
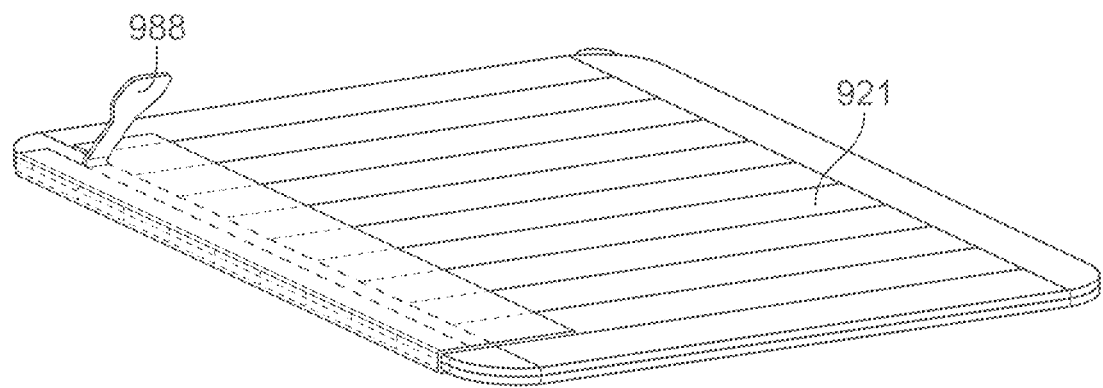
FIG. 18D is a top perspective view of the device of FIG. 18A in a strained and folded configuration while detaching an attachment sheet.
Figure 18E:
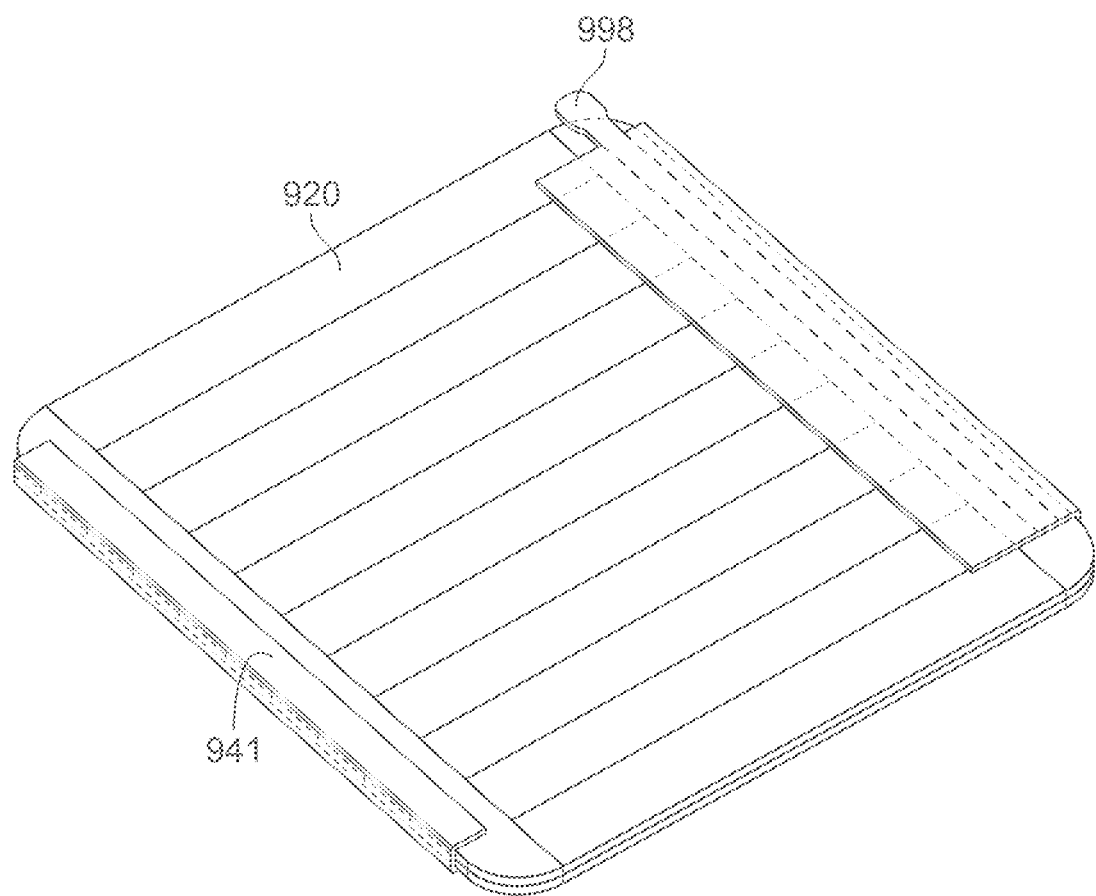
FIG. 18E is a top perspective view of the device of FIG. 18A with a first side of the dressing assembly detached from the carrier and the cover removed.
Figure 18F:
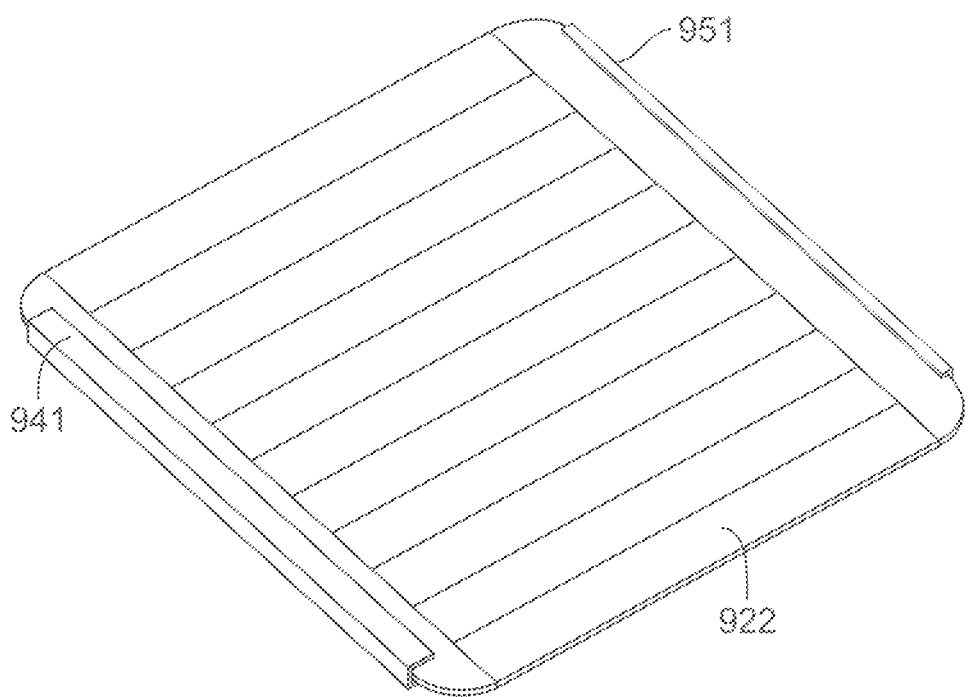
FIG. 18F is a top perspective of the device of FIG. 18A with the dressing assembly detached from the carrier.
Figure 18G:
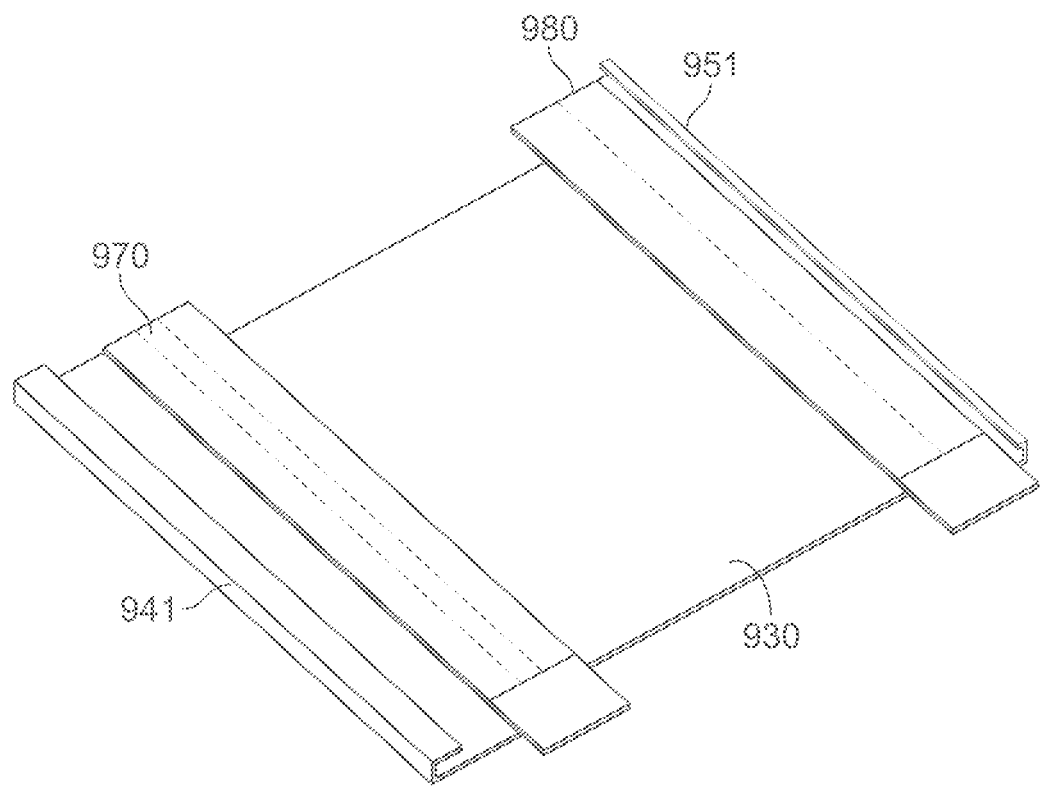
FIG. 18G is a top perspective view of the device of FIG. 18A with the carrier detached and removed.
Figure 18H:
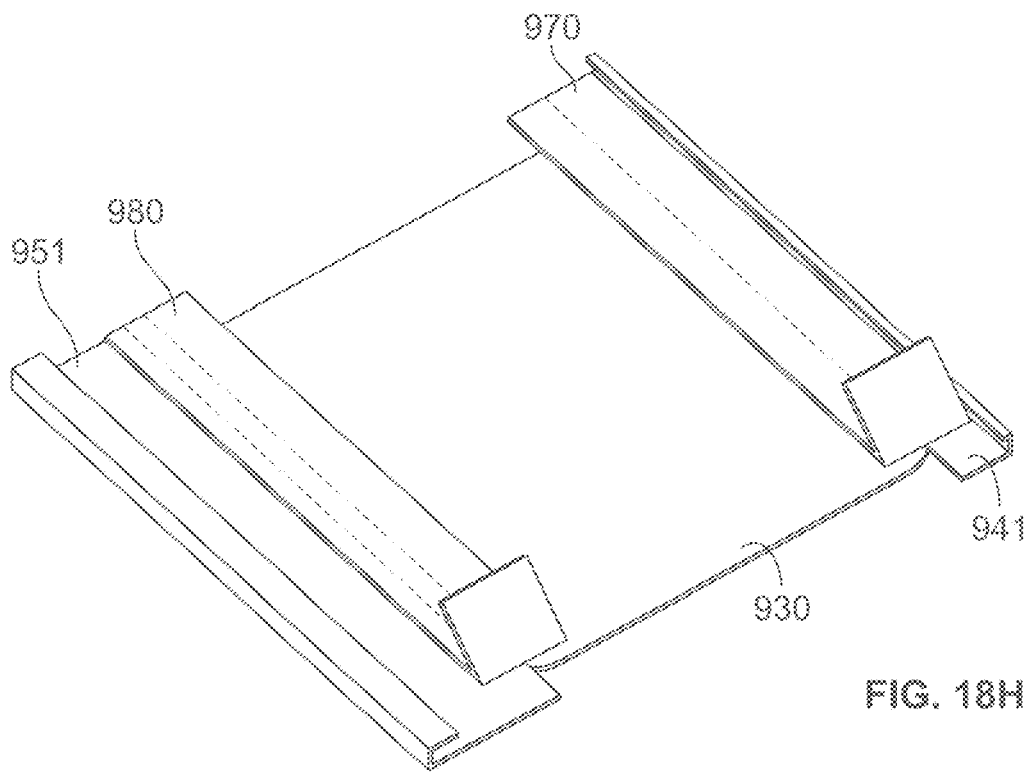
FIG. 18H is a perspective view of the device of FIG. 18A with the dressing being separated from the attachment sheets.
Figure 18I:
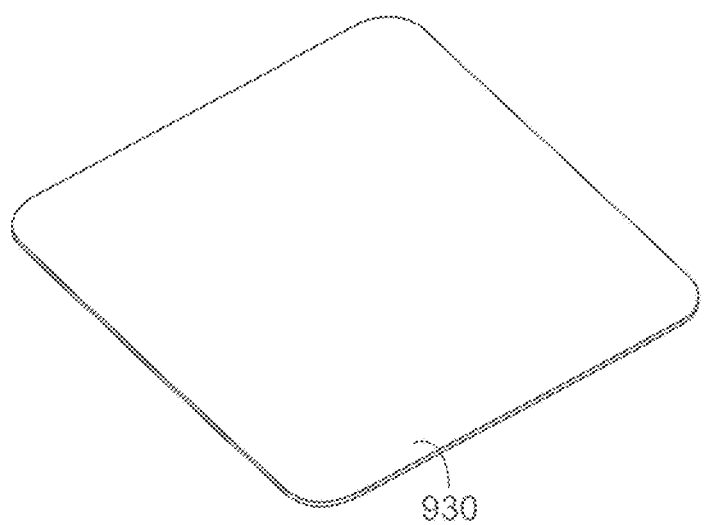
FIG. 18I is a perspective view of the device of FIG. 18A with the dressing separated from the attachment sheets.
Figure 18J:
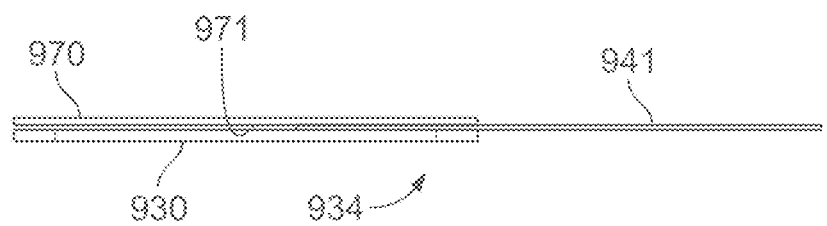
FIG. 18J is a side view of the dressing depicted in FIG. 18G.

As shown in FIG. 18J, the attachment sheet 941 and side 934 of the dressing are attached on same side 971 of the adhesive structure 970 with the attachment sheet 941 overlapping but unattached to the dressing 931. The attachment sheet 941 has a second side 944 that is coupled to the cover 921 of the device 920 for example, by bonding with a low surface energy PSA such as an acrylic adhesive. Attachment sheet 941 may also have a pull tab 981 in an unattached region between the attachment to the adhesive structure 970 and attachment to the cover 921. After the dressing has been strained, the perforation pull tab 981 is located at the inside surface 960 of the cover 921 or alternatively at the seam between the cover 921 and the base 922.

The attachment sheet 951 is coupled at its side 954 to the back side 998 of the base 922 for example, by bonding with a low surface energy PSA such as an acrylic adhesive. The side 953 of attachment sheet 951 is attached to the side 933 of the dressing 930 by way of an adhesive structure 980 such as KAPTON® tape or a peelable adhesive, and in a manner similar to the adhesive structure 970 that attaches the side 944 of the dressing 930 to the attachment sheet 941. The attachment sheet 951 may include a pull tab 988 that is located on the back side 998 of the base adjacent and inside of the attachment zone 955 of the attachment sheet 951 to the back of the base 952.

According to some variations, the attachment sheets 941, 951 are flexible while being relatively inelastic with respect to the dressing 930 and may be constructed, e.g., out of a LDPE. The attachment sheets 941, 951 may be manufactured to be tearable along the material length while providing tensile strength in other directions, in particular in the tensioning direction of the material of the attachment sheet 941 (direction in which dressing is tensioned, stressed or strained). An example of such material is an LDPE polymer which is produced by an extrusion process that creates an anisotropic or directionally biased grain whereby the material is tearable with the direction of the grain, but has a relative resistance to tearing in the direction transverse to the grain.

The cover 921, when opened, exerts a straining force on the dressing 930 through the attachment sheet 941. FIG. 18A shows the assembly 900 in an unstrained configuration, while FIG. 18B shows the assembly 900 in an opened and strained configuration which may be applied to the skin. As shown in FIG. 18C, when strained, the tab 981 on the attachment sheet 941 is located over the inner surface of the cover 921 (folded back and exposed) and is accessible to a user. After applying the dressing 930, the cover 921 and base 922 may be removed.

The cover 921 and base 922 are separable from each when the tab 988 is pulled. FIG. 18C shows the assembly with the cover positioned with the dressing face down for example as it would be when applied to the skin of a subject. As shown in FIG. 18D the tab 988 is pulled to release the cover 921 from the remaining dressing assembly 910. As shown in FIG. 18E the cover 921 is removed from the remainder of the device 920, exposing the second pull tab 998. As shown in FIG. 18F, the second pulled tab 998 has released the base 922 from the dressing assembly 910 with attachment sheets 941, 951 unattached to the base 922. As shown in FIG. 18G, the base 922 is removed ant the remainder of the attachment sheets 941, 951 and the adhesive structures 970, 980 may be peeled away from the dressing 930 as shown if FIG. 18H with the dressing remaining on the skin in a configuration as shown in FIG. 18I.

Figure 19A:
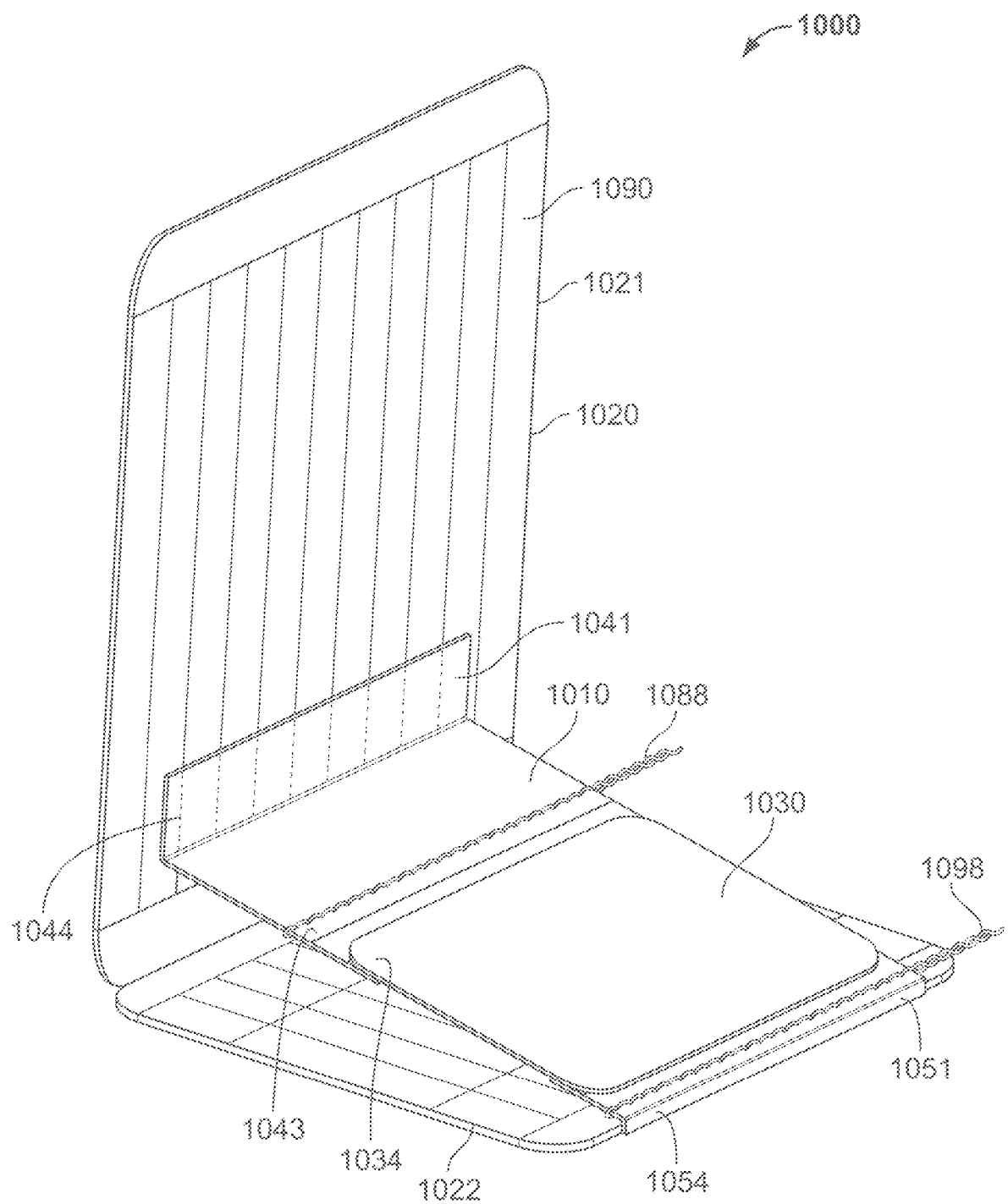
FIG. 19A is a perspective view of a variation of a dressing and packing assembly device.

Referring to FIGS. 19A through 19D, a variation of a dressing and packaging assembly 1000 is illustrated. The packaging assembly 1000 comprises an applicator and/or tensioning device 1020 and a dressing assembly 1010 including a dressing 1030. FIG. 19A shows the dressing assembly 1010 coupled to the applicator or tensioning device 1020. The tensioning member or applicator 1020 may be constructed in a similar manner as the tensioning and applicators described herein and shown in FIGS. 1A to 22B.

The device 1020 comprises a cover 1021 and a base 1022. The dressing assembly 1010 is removably coupled or anchored to the device 1020 which may act as a dressing carrier. The dressing assembly may be attached to a tensioning member or applicator in a manner similar to the assemblies described herein. The dressing assembly 1010 includes an attachment sheet 1041 and attachment sheet 1051. The attachment sheet 1041 has a first side 1043 that is attached to the second side 1034 of the dressing 1030 by way of an adhesive structure 1070 such described with reference to adhesive structures 970, 980. The attachment sheet 1041 has a second side 1044 that is coupled to the cover 1021 of the device 1020 for example, by bonding with a low surface energy PSA such as an acrylic adhesive. Attachment sheet 1041 also has a ripcord 1088 stitched along its length at an unattached portion of the attachment sheet 1041, between its attachment to the adhesive structure 1070 and attachment to the cover 1021. Various types of stitches may be used including but not limited to a chainstitch or a lockstitch. After the dressing has been strained, the ripcord 1088 is located at the exposed inner side 1090 of the cover 1021 or alternatively at the seam between the cover 1021 and the base 1022.

The attachment sheet 1051 is coupled at its side 1054 to the back side of the base 1022 for example, by bonding with a low surface energy PSA such as an acrylic adhesive. The side 1053 of attachment sheet 1051 is attached to the side 1033 of the dressing by way of an adhesive structure 1080 such as KAPTON® tape or a peelable adhesive, and in a manner similar to the adhesive structure 1070 that attaches the side 1034 of the dressing 1030 to the attachment sheet 1041. The attachment sheet 1051 includes a ripcord 1098 that is located between attachment to the adhesive structure 1090 and attachment to the back of the base. The ends of the ripcords 1088, 1098 extend out of the tensioning member 1020 for easy accessibility.

Figure 19B:
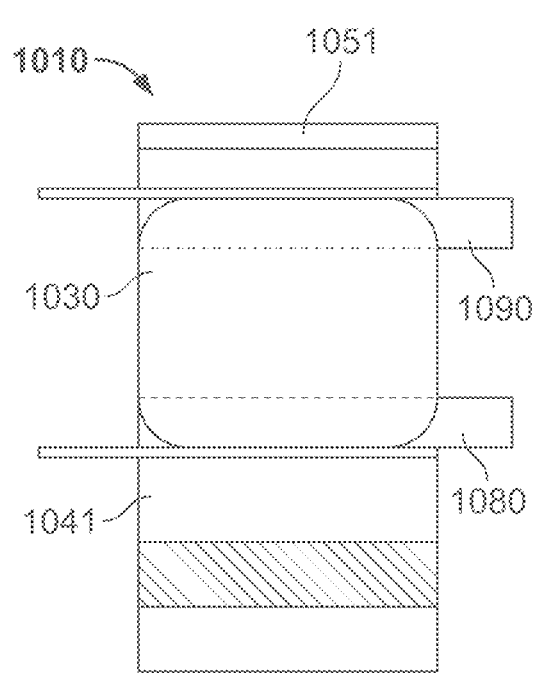
FIG. 19B is a top view of an unstrained configuration of a dressing assembly of FIG. 19A
Figure 19C:
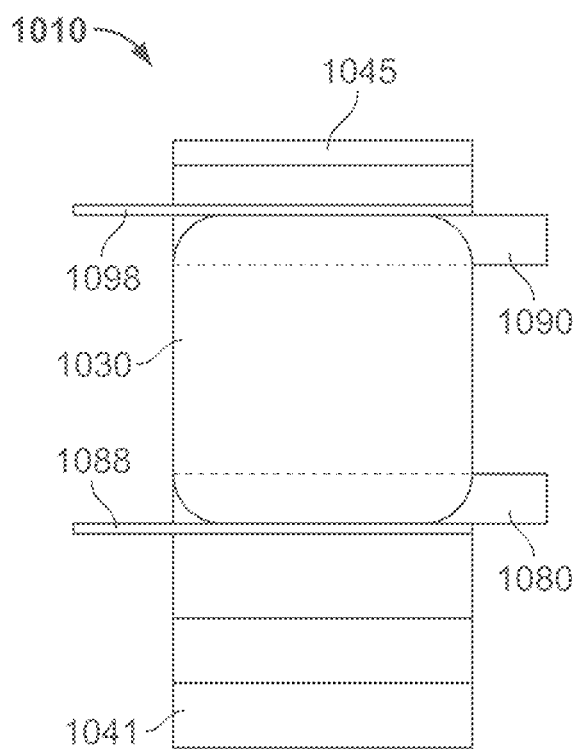
FIG. 19C is a top view of a strained and attached configuration of the dressing assembly of FIG. 19B.

FIGS. 19A and 19B illustrate the dressing assembly 1010 in an unstrained configuration. The cover 1021, when opened, exerts a straining force on the dressing 1030 through the attachment sheet 1041. FIG. 19C illustrates the dressing assembly 1010 in a strained configuration.

Figure 19D:
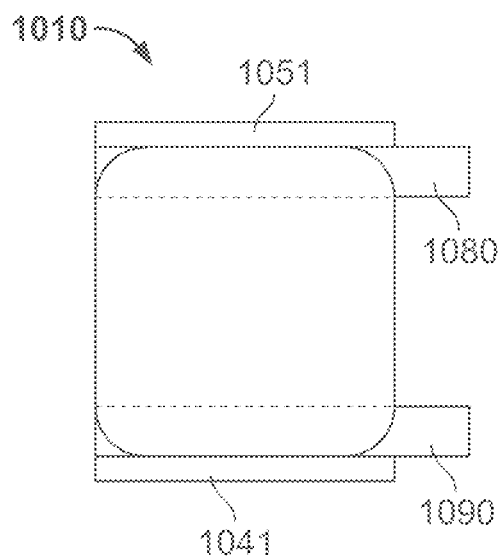
FIG. 19D is a top view of a strained and detached configuration of the dressing assembly of FIG. 19B.
Figure 19E:
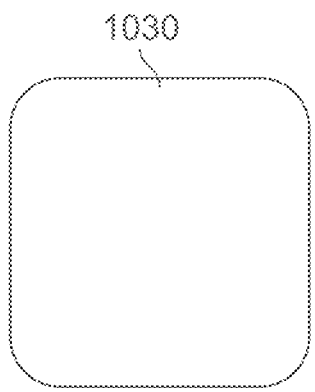
FIG. 19E is a top view of a dressing of FIG. 19B.

After the dressing is strained and applied, the ripcords 1088, 1098 are pulled to separate the portion of the attachment sheets 1041, 1051 attached to the tensioning device 1020 from the portions of the attachment sheets 1041, 1051 attached to the dressing 1030. The applicator or tensioning device 1020 may then be removed as shown in FIG. 19D. The adhesive structures 1080, 1090 may then be peeled away to remove the remaining portion of the dressing assembly 1010 and attachment sheets 1041, 1051, from the dressing as shown in FIG. 19E.

Figure 20A:
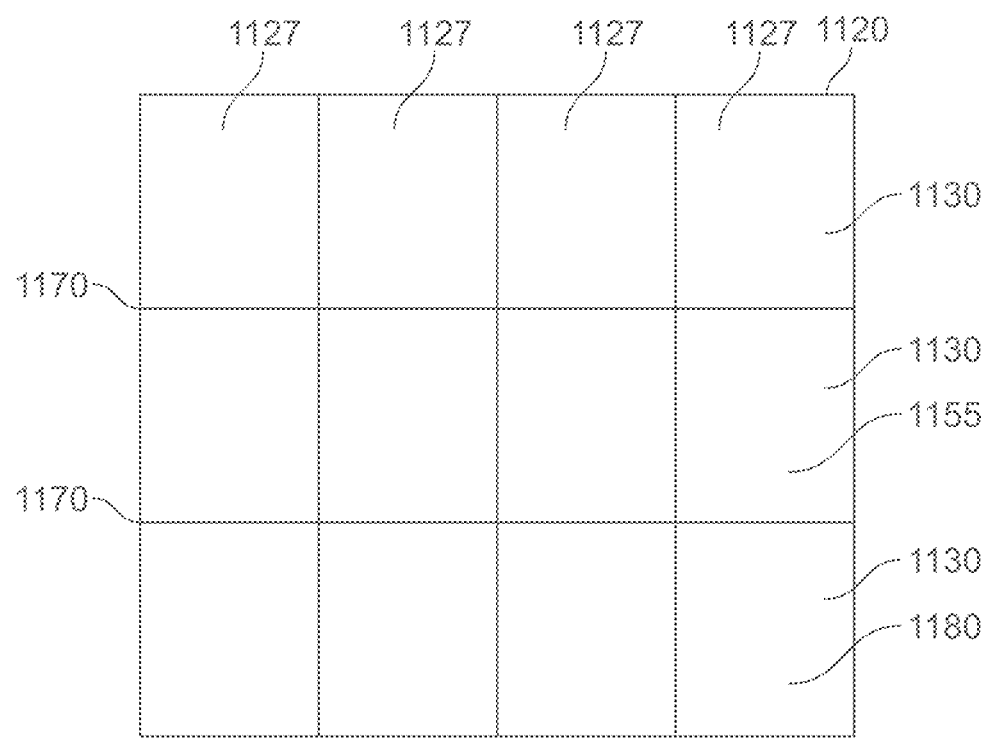
FIG. 20A is a top view of a variation of a dressing carrier, support, base tensioning device or applicator.
Figure 20B:
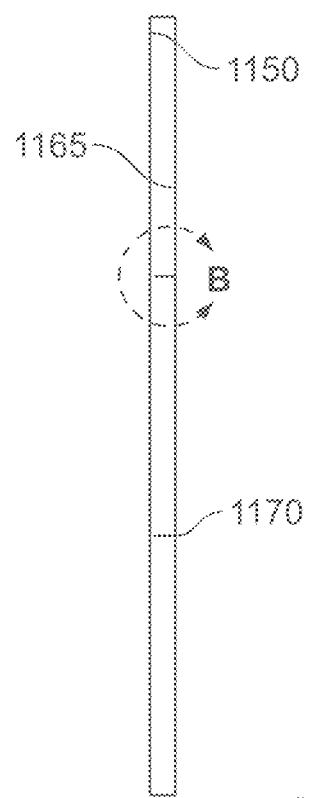
FIG. 20B is a side view of the dressing carrier, support, base tensioning device or applicator of FIG. 20A in a first configuration.
Figure 20C:
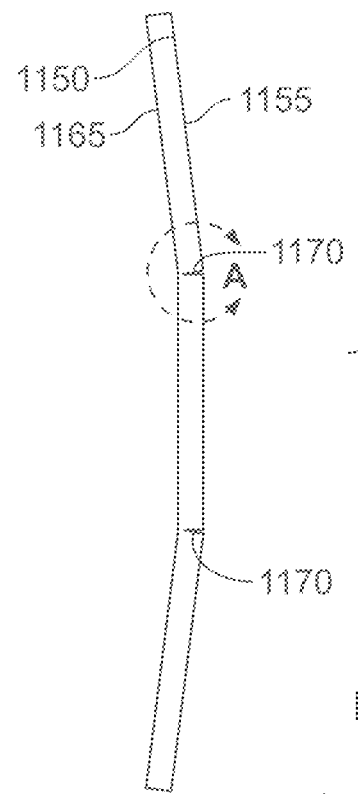
FIG. 20C is a side view of the dressing carrier, support, base tensioning device or applicator of FIG. 20A in a second configuration.
Figure 21A:
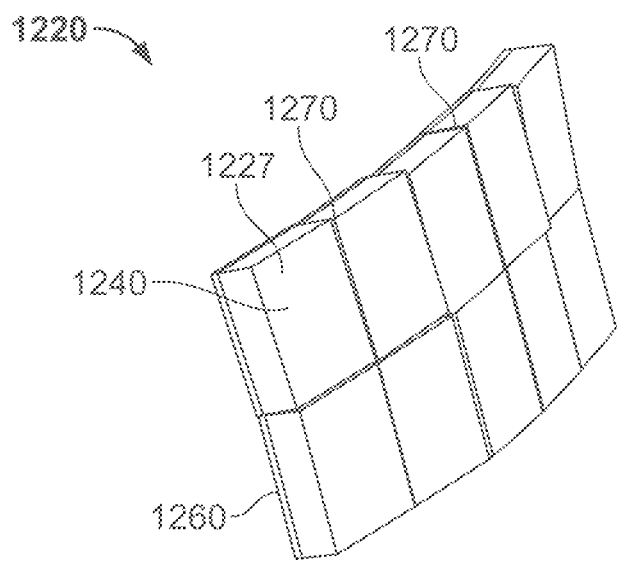
FIG. 21A is a perspective view of a variation of a dressing carrier, support, base tensioning device or applicator
Figure 21B:
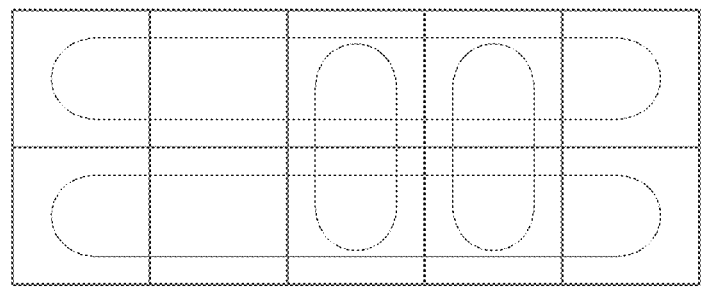
FIG. 21B is a top view of the dressing carrier, support, base tensioning device or applicator of FIG. 21A.
Figure 21C:
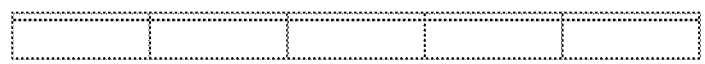
FIG. 21C is a side view of dressing carrier, support, base tensioning device or applicator of FIG. 21A.
Figure 21D:
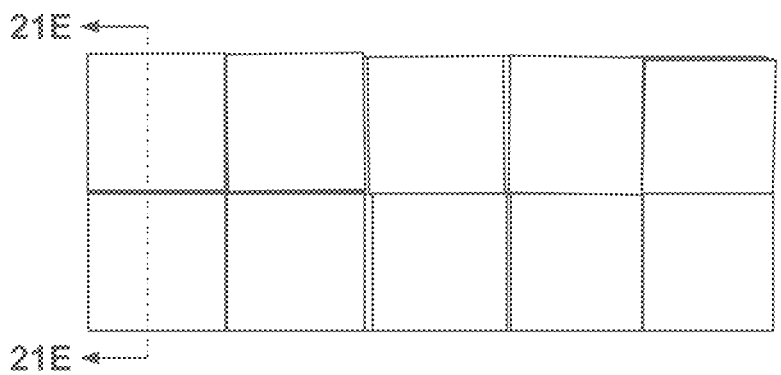
FIG. 21D is a top view of the dressing carrier, support, base tensioning device or applicator of FIG. 21A in a flexed configuration.
Figure 21E:
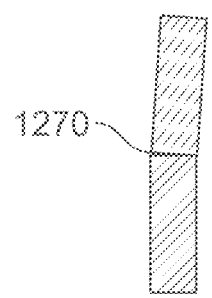
FIG. 21E is a cross-section of FIG. 21D along the lines A-A

Referring to FIGS. 20A to 20C, a variation is shown of a dressing carrier, tensioning device or applicator 1120. The device 1120 comprises a plurality of segments 1130 formed by scoring a substrate 1150 on one side 1155 of a planar surface. The scores 1170 may be formed in one or more directions or having one or more shapes, curved or straight. Additionally the scores may be formed on both sides permitting both convex and concave shaping of a device. As illustrated, the scores 1170 permit shaping of the device or an attached dressing. The scores 1170 as illustrated are formed on a first side 1155 of a planar surface of the device while the second side 1165 is not scored. When a force is applied to the second side 1165, the substrate bends. When a force is applied to the first side 1155, the substrate 1150 the device does not flex at the scores 1170. The remaining substrate at the scores 1170 may act as flexion limiter while the scores 1170 act as a flex element.

When a convex dressing shape is desired for a concave surface, the dressing may be attached on the first side 1155 so that when the substrate is bent, the dressing forms a convex shape to match a concave contour where the device is to be applied. When a concave dressing shape is desired for a convex body contour, the dressing may be positioned on the second side 1165 of the substrate 1150. So that when the substrate is bent, the dressing forms a concave shape to match a convex body contour where the device is to be applied. Various dressing backings may be provided for different body locations or contours.

According to variations, the score may be orthogonal or have orthogonal components with respect to the segments 1127 of the carrier, applicator or tensioning device. The segments 1127 may be similar to segments shown in FIGS. 1A to 22B.

Referring to FIGS. 21A to 21D, a variation is shown of a dressing carrier, tensioning device or applicator 1220. The device 1220 comprises a plurality of foam cells 1240 coupled by and adhesive backing 1260. The foam cells 1240 form a plurality of segments 1227 that permit flexing in multiple directions so that the device conforms to a curvature, profile or shape of a subject where the dressing is to be applied. The foam may be sufficiently thick to generally provide added column strength for straining a dressing. i.e. a resistance to bending. A backing or support may be provided for straining a dressing, for example constructed of a material with an elastic modulus and appropriate thickness that will, at minimum, counteract the force created by straining the dressing. The dressing strain may be fixed, for example, using an adhesive on the back of a portion of the dressing assembly or attachment sheet. After the dressing is fixed, the backing or support may be removed permitting increased manipulation of the shape of the strained dressing to conform to a greater degree to the shape of the patient's body contours where the dressing is to be applied.

As illustrated, the separations 1270 between the foam sections permit shaping of the device. The separations 1270 as illustrated are formed on a first side 1255 of a planar surface of the device while the second side 1265 is not scored. When a force is applied to the first side 1255, the substrate bends. When a force is applied to the second side 1265, the substrate 1250 the device does not flex at the separations. The remaining substrate at the separations may act as flexion limiter while the scores act as a flex element.

When a convex dressing shape is desired for a concave surface, the dressing may be attached on the first side 1255 so that when the substrate is bent, the dressing forms a convex shape to match a concave contour where the device is to be applied. When a concave dressing shape is desired for a convex body contour, the dressing may be positioned on the second side 1265 of the substrate 1250. So that when the substrate is bent, the dressing forms a concave shape to match a convex body contour where the device is to be applied. Various dressing backings may be provided for different body locations or contours.

Figure 22B:
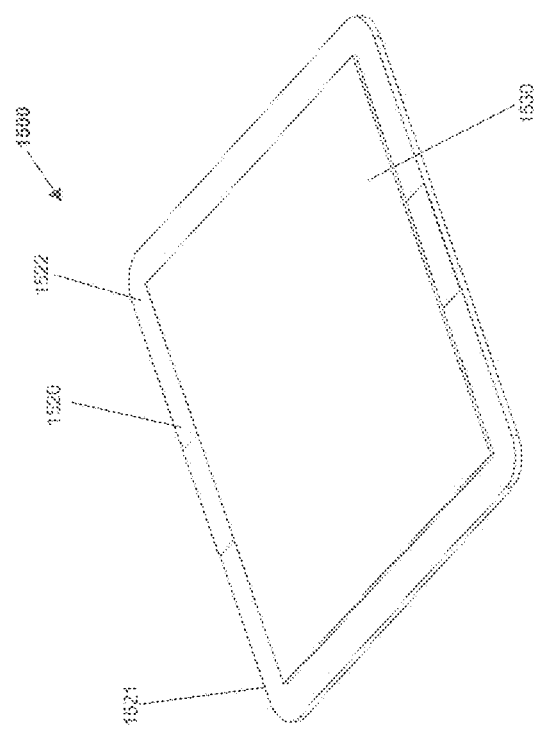
FIG. 22B is a perspective view of a variation of a dressing and packaging device in a strained configuration.
Figure 22A:
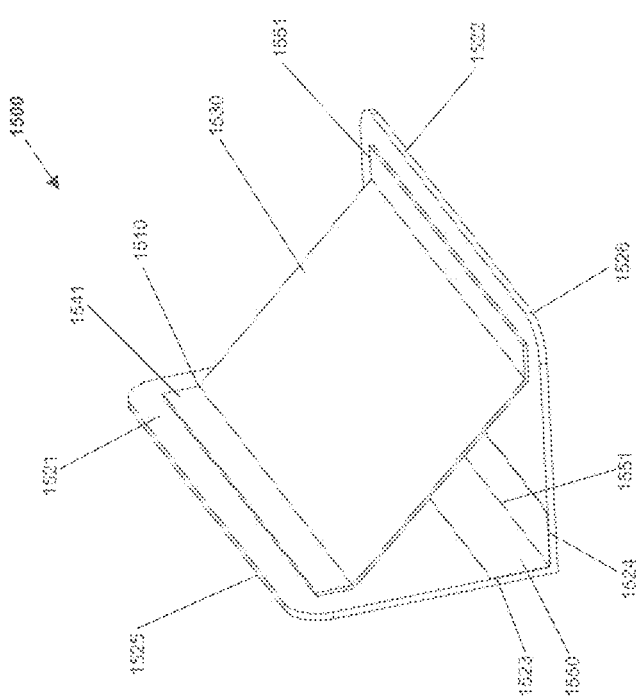
FIG. 22A is a perspective view of a variation of a dressing and packaging assembly in an unstrained configuration.

Referring to FIGS. 22A and 22B, a variation of a dressing and packaging assembly 1500 is illustrated. The packaging assembly 1500 comprises an applicator and/or tensioning device 1520 and a dressing assembly 1510 including a dressing 1530. The packaging assembly 1500, applicator or tensioning device 1520, and/or dressing assembly 1510 may be configured to pre-strain the dressing 1530 and/or permit transfer of the pre-strained dressing 1530 to the skin of a subject.

The device 1520 may comprise a cover 1521 and a base 1522. The dressing assembly 1510 is removably coupled or anchored to the device 1520, and may serve as a dressing carrier. The cover 1521 and base 1522 are movably, pivotably, bendably or hingedly coupled at sides 1523, 1524 and may be constructed in a manner similar to that described with respect to covers and bases described in FIGS. 1A to 22B. Attachment regions 1541, 1551 of the dressing assembly 1510 are attached near free sides 1525, 1526 of cover 1521, 1522 respectively, for example by way of a peelable adhesive or removable adhesive structures. However an attachment sheet or attachment structure described with respect FIGS. 1A to 22B herein may be used. The attachment regions 1541, 1551 and or positioning of the dressing 1530 on the device 1520, may be symmetric with respect to a line defined by attachment of sides 1523, 1524 of the cover 1521 and base 1522 respectively. As shown in FIG. 22B, the dressing 1530 is strained with the cover 1521 and base 1522 are opened. The dressing 1530 may then be applied to the skin of a subject and the device 1520 may be peeled away from the dressing 1530. In addition or alternatively, the cover 1521 and base 1522 may be separated by way of a perforation formed in the substrate of the device 1520 or a perforation 1551 formed in an attachment structure 1550 such as a tape or layer of material that attaches sides 1523 and 1524 of the cover 1521 and base 1522 respectively.

In some variations, the device 1520 may optionally comprise an adhesive coating or adhesive tape on the cover 1521 and/or base 1522 which may adhere to the dressing 1530 when the dressing 1530 is tensioned and the dressing comes in further contact with the cover 1521 and base 1522. In some variations, the adhesive is configured to maintain the dressing 1530 in a tensioned state and/or against the cover 1521 and/or base 1522. The adhesive coating or adhesive tape may be located along the side regions 1523, 1524 of the cover 1521 and/or base 1522, but many also be provided adjacent to the attachment regions 1541, 1551. Release liners may also be provided to reduce inadvertent adhesion of the dressing or other structures to the adhesive until activation of the device 1520 is desired.

According to variations the various assemblies or devices described herein may provide a temporary wound dressing that may be applied before a wound is closed. The assembly may be configured to apply a dressing to a wound and to use the packaging or applicator to apply pressure to the wound before removing or separating the applicator, tensioning device or dressing carrier, base or support from the dressing. According to this variation which may be provided with any of the embodiments described below, the packaging or applicator has sufficient rigidity to distribute a relatively even or firm force to a wound by applying pressure to the packaging or applicator when and/or after the dressing is applied to a wound. According to a variation, such dressing may include a coagulation agent or other agent or medicament, for example as described herein. According to another variation, margins as described herein, are provided on such a device between a dressing and edges used to manipulate the device.

The assemblies or devices described herein may also form a dressing support structure. For example, the dressing support structure may comprise of a plurality of segments of the base structures. The dressing support structure may comprise at least 3 segments that extend at least from a first side of the dressing to a second side of the dressing. The dressing support structure may comprise a plurality of segments such as segments described in FIGS. 1A to 22B that are coupled or formed together. The plurality of segments of a cover described herein may also provide support to a dressing when the cover is folded over 360 degrees with respect to the corresponding base structure.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

The invention claimed is:

1. A skin treatment device, comprising:
a prestrained elastic sheet;
an attachment sheet;
a release element; and
a strain maintaining support structure;
wherein the prestrained elastic sheet is coupled to the strain maintaining support structure in a configuration having a predetermined amount of strain;
wherein the prestrained elastic sheet is coupled to the strain maintaining support with the attachment sheet; and
wherein the release element is configured to release the elastic sheet from the strain maintaining support structure.

2. The skin treatment device of claim 1, wherein the release element comprises a pull tab.

3. The skin treatment device of claim 1, wherein the release element comprises at least one notch in the attachment sheet.

4. The skin treatment device of claim 1, wherein the release element comprises a perforation in the attachment sheet.

5. The skin treatment device of claim 1, wherein the release element comprises a cutter.

6. The skin treatment device of claim 1, wherein the attachment sheet comprises a directionally biased grain tearable in a predetermined direction.

7. The skin treatment device of claim 1, wherein the attachment sheet is adhered to the elastic sheet.

8. The skin treatment device of claim 1, wherein the strain maintaining support structure is more rigid than the elastic sheet.

9. A skin treatment device comprising:
a prestrained elastic sheet comprising a first side and a second side;
a first attachment sheet;
a second attachment sheet;
a release mechanism; and
a strain maintaining support structure;
wherein the prestrained elastic sheet is coupled to the strain maintaining support structure in a configuration having a predetermined amount of strain; and
wherein the prestrained elastic sheet is coupled to the strain maintaining support structure at the first side with the first attachment sheet and the prestrained elastic sheet is coupled to the strain maintaining support structure at the second side with the second attachment sheet.

10. The skin treatment device of claim 9, wherein the release mechanism is configured to release the elastic sheet from the strain maintaining support structure.

11. The skin treatment device of claim 9, wherein the release mechanism comprises a pull tab.

12. The skin treatment device of claim 9, wherein the release mechanism comprises a least one notch in the attachment sheet.

13. The skin treatment device of claim 9, wherein the release mechanism comprises a perforation in the attachment sheet.

14. The skin treatment device of claim 9, wherein the release mechanism comprises a cutter.

15. The skin treatment device of claim 9, wherein the first attachment sheet comprises a directionally biased grain tearable along a line parallel to the first side of the elastic sheet; and wherein the second attachment sheet comprises a directionally biased grain tearable along a line parallel to the second side of the elastic sheet.

16. The skin treatment device of claim 9, wherein the first attachment sheet is adhered to the first side of the elastic sheet and wherein the second attachment sheet is adhered to the second side of the elastic sheet.

17. The skin treatment device of claim 9, wherein the first attachment sheet is adhered to the strain maintaining support structure.

18. The skin treatment device of claim 9, wherein the strain maintaining support structure is more rigid than the elastic sheet.

19. The skin treatment device of claim 9, wherein the strain maintaining support structure comprises a plurality of less flexible regions and a plurality of more flexible regions that permit flexing of the strain maintaining support structure at the more flexible regions.

20. A skin treatment device, comprising:
a prestrained elastic sheet;
an attachment sheet;
a release element; and
a strain maintaining support structure;
wherein the prestrained elastic sheet is coupled to the strain maintaining support structure in a configuration having a predetermined amount of strain;
wherein the prestrained elastic sheet is coupled to the strain maintaining support with the attachment sheet; and
wherein the attachment sheet is adhered to the strain maintaining support structure.

21. The skin treatment device of claim 20, wherein the release element is configured to release the elastic sheet from the strain maintaining support structure.

22. The skin treatment device of claim 21, wherein the release element comprises at least one notch in the attachment sheet.

23. The skin treatment device of claim 21, wherein the release element comprises a perforation in the attachment sheet.

24. The skin treatment device of claim 20, wherein the release element comprises a pull tab.

25. The skin treatment device of claim 20, wherein the release element comprises a cutter.

26. The skin treatment device of claim 20, wherein the attachment sheet comprises a directionally biased grain tearable in a predetermined direction.

27. The skin treatment device of claim 20, wherein the attachment sheet is adhered to the elastic sheet.

28. The skin treatment device of claim 20, wherein the strain maintaining support structure is more rigid than the elastic sheet.

29. The skin treatment device of claim 20, wherein the strain maintaining support structure comprises a plurality of less flexible regions and a plurality of more flexible regions that permit flexing of the strain maintain structure at the more flexible regions.

30. A skin treatment device, comprising:
a prestrained elastic sheet;
an attachment sheet;
a release element; and
a strain maintaining support structure;
wherein the prestrained elastic sheet is coupled to the strain maintaining support structure in a configuration having a predetermined amount of strain;
wherein the prestrained elastic sheet is coupled to the strain maintaining support with the attachment sheet; and
wherein the strain maintaining support structure comprises a plurality of less flexible regions and a plurality of more flexible regions that permit flexing of the strain maintain structure at the more flexible regions.

31. The skin treatment device of claim 30 wherein the release element is configured to release the elastic sheet from the strain maintaining support structure.

32. The skin treatment device of claim 31, wherein the release element comprises a pull tab.

33. The skin treatment device of claim 31, wherein the release element comprises at least one notch in the attachment sheet.

34. The skin treatment device of claim 31, wherein the release element comprises a perforation in the attachment sheet.

35. The skin treatment device of claim 30, wherein the release element comprises a cutter.

36. The skin treatment device of claim 30, wherein the attachment sheet comprises a directionally biased grain tearable in a predetermined direction.

37. The skin treatment device of claim 30, wherein the attachment sheet is adhered to the elastic sheet.

38. The skin treatment device of claim 30, wherein the attachment sheet is adhered to the strain maintaining support structure.

39. The skin treatment device of claim 30, wherein the strain maintaining support structure is more rigid than the elastic sheet.

* * * * *